(12) United States Patent
Genung et al.

(10) Patent No.: US 11,459,324 B2
(45) Date of Patent: Oct. 4, 2022

(54) O-GLYCOPROTEIN-2-ACETAMIDO-2-DEOXY-3-D-GLYCOPYRANOSIDASE INHIBITORS

(71) Applicant: BIOGEN MA INC., Cambridge, MA (US)

(72) Inventors: Nathan Genung, Cambridge, MA (US); Kevin M. Guckian, Cambridge, MA (US); Jeffrey Vessels, Cambridge, MA (US); Lei Zhang, Cambridge, MA (US); Ryan Gianatassio, Cambridge, MA (US); Edward Yin Shiang Lin, Cambridge, MA (US); Zhili Xin, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 73 days.

(21) Appl. No.: 16/978,550

(22) PCT Filed: Mar. 13, 2019

(86) PCT No.: PCT/US2019/021995
§ 371 (c)(1),
(2) Date: Sep. 4, 2020

(87) PCT Pub. No.: WO2019/178191
PCT Pub. Date: Sep. 19, 2019

(65) Prior Publication Data
US 2021/0040080 A1    Feb. 11, 2021

Related U.S. Application Data

(60) Provisional application No. 62/699,443, filed on Jul. 17, 2018, provisional application No. 62/690,536, filed on Jun. 27, 2018, provisional application No. 62/264,932, filed on Mar. 14, 2018.

(51) Int. Cl.
C07D 417/14    (2006.01)
C07D 417/06    (2006.01)
C07D 471/04    (2006.01)

(52) U.S. Cl.
CPC ......... *C07D 417/14* (2013.01); *C07D 417/06* (2013.01); *C07D 471/04* (2013.01)

(58) Field of Classification Search
None
See application file for complete search history.

(56) References Cited

U.S. PATENT DOCUMENTS 9,340,510 B2 * 5/2016 Roth .................... C07D 215/16

FOREIGN PATENT DOCUMENTS

| WO | 2011/143495 A1 | 11/2011 | |
|---|---|---|---|
| WO | 2014/159234 A1 | 10/2014 | |
| WO | WO-2014159234 A1 * | 10/2014 | ........... A61K 31/496 |
| WO | 2017/106254 A1 | 6/2017 | |
| WO | 2018/109198 A1 | 6/2018 | |
| WO | 2018/109202 A1 | 6/2018 | |
| WO | 2018/154133 A1 | 8/2018 | |

OTHER PUBLICATIONS

International Search Report and Written Opinion for Application No. PCT/Us2019/021995, dated May 14, 2019, 10 pages.

* cited by examiner

*Primary Examiner* — Heidi Reese
(74) *Attorney, Agent, or Firm* — McCarter & English, LLP; Steven G. Davis; Xin Zhang

(57) ABSTRACT

Described herein are compounds represented by formula (I") or a pharmaceutically acceptable salt thereof, pharmaceutical compositions comprising the same and methods of preparing and using the same. The variables Ar, $R^a$, $R^b$, m, n, $Y^1$, $Y^2$, $R^3$ and $R^4$ are defined herein.

21 Claims, No Drawings

O-GLYCOPROTEIN-2-ACETAMIDO-2-DEOXY-3-D-GLYCOPYRANOSIDASE INHIBITORS

CROSS REFERENCE TO RELATED APPLICATIONS

This application is a 35 U.S.C. § 371 national stage filing of International Application No. PCT/US2019/021995, filed on Mar. 13, 2019, which in turn claims the benefit of U.S. Provisional Patent Application No. 62/699,443, filed Jul. 17, 2018; U.S. Provisional Patent Application No. 62/690,536, filed on Jun. 27, 2018; and U.S. Provisional Patent Application No. 62/642,932, filed Mar. 14, 2018; each of which are incorporated herein by reference in its entirety.

BACKGROUND

A wide range of cellular proteins, both nuclear and cytoplasmic, are post-translationally modified by the addition of the monosaccharide 2-acetamido-2-deoxy-R-D-glucopyranoside (β-N-acetyl glucosamine) which is attached via an O-glycosidic linkage. This monosaccharide is generally referred to as β-linked N-acetylglucosamine or O-GcNAc. The enzyme responsible for post-translationally linking β-N-acetylglucosamine (GlcNAc) to specific serine and threonine residues of numerous nucleocytoplasmic proteins is O-GcNAc transferase (OGTase). A second enzyme, known as O-glycoprotein-2-acetamido-2-deoxy-3-D-glucopyranosidase or O-GlcNAcase or OGA, removes this post-translational modification to liberate proteins, making the O-GcNAc-modification a dynamic cycle occurring several times during the lifetime of a protein.

O-GlcNAc-modified proteins regulate a wide range of vital cellular functions including, e.g., transcription, proteasomal degradation and cellular signaling. O-GlcNAc is also found on many structural proteins, including the cytoskeletal protein "tau" which is responsible for stabilizing a key cellular network of microtubules that is essential for distributing proteins and nutrients within neurons. Importantly, tau has been clearly implicated in the etiology of several diseases including tauopathies, Alzheimer's disease, Parkinson's disease, dementia and cancer.

It is well established that Alzheimer's disease and a number of related tauopathies including Progressive Supranuclear Palsy (PSP) and amyotrophic lateral sclerosis (ALS) are characterized, in part, by the development of neurofibrillary tangles (NFTs). These NFTs are aggregates of paired helical filaments (PHFs) and are composed of an abnormal form of tau. In AD patients, tau becomes hyperphosphorylated, thereby disrupting its normal function, forming PHFs and ultimately aggregating to form NFTs.

Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups.

It has recently emerged that increases in phosphorylation levels result in decreased O-GlcNAc levels and conversely, increased O-GlcNAc levels correlate with decreased phosphorylation levels. It has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase, which prevents hyperphosphorylation of tau by preventing removal of O-GlcNac from tau, should compensate for the age-related impairment of glucose metabolism within the brains of health individuals as well as patients suffering from Alzheimer's disease or related neurodegenerative diseases.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

In view of foregoing technical challenge, and given the potential for regulation of O-GlcNAcase for treatment of AD, tauopathies and other neurological diseases, there remains a need for development of potent and selective O-GlcNAcase inhibitors.

SUMMARY

Described herein are compounds that are useful treating various diseases, disorders and medical conditions, including but not limited to those associated with proteins that are modified by O-GlcNAcase.

A first embodiment of a compound of the present invention is represented by the following structural formula:

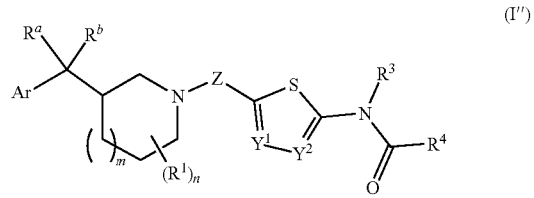

(I'')

or a pharmaceutically acceptable salt thereof, wherein:
Ar is an optionally substituted 5- to 10-membered heteroaryl, an optionally substituted phenyl or an optionally substituted phenyl fused to an optionally substituted non-aromatic 5- to 6-membered heterocycle;
$Y^1$ and $Y^2$ are each $CR^c$ or N, wherein at least one of Y or $Y^2$ is N;
Z is $CR^2R^2$, $C(=O)$, $(CR^2R^2)_2$, $CH_2C(=O)$, or $C(=O)CH_2$;
$R^a$, $R^b$ and $R^c$ are each independently —H, halo, $C_1$-$C_4$ alkyl, $C_1$-$C_4$ haloalkyl, or $C_1$-$C_4$ alkoxy, or $R^a$ and $R^b$ taken together with their intervening carbon atom form a $C_3$-$C_6$ cycloalkyl;
m is 0 or 1;
n is 0 or an integer from 1 to 7;
when n is other than 0, $R^1$, for each occurrence, is independently halo, $C_1$-$C_4$ alkyl, $C_1$-$C_4$ haloalkyl, $C_1$-$C_4$ alkoxy or $C_1$-$C_4$ haloalkoxy;
$R^2$, for each occurrence, is independently —H, halo, $C_1$-$C_4$ alkyl, $C_1$-$C_4$ haloalkyl, $C_3$-$C_{10}$cycloalkyl, or $C_3$-$C_{10}$ halocycloalkyl;
or alternatively two $R^2$ together with the carbon atom to which they are attached form a $C_3$-$C_{10}$ cycloalkyl;
$R^3$ is —H or $C_1$-$C_4$ alkyl; and
$R^4$ is —H, $C_1$-$C_4$ alkyl, $C_1$-$C_4$ haloalkyl, or $C_3$-$C_6$ cycloalkyl;

or alternatively $R^3$ and $R^4$ taken together with their intervening atoms form an optionally substituted 5- to 7-membered heterocyclyl.

Provided is a pharmaceutical composition comprising at least one compound described herein, or a pharmaceutically acceptable salt thereof, and at least one pharmaceutically acceptable excipient.

Also provided is a method of treating a subject with a disease or condition selected from a neurodegenerative disease, a tauopathy, diabetes, cancer and stress, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of inhibiting O-GlcNAcase in a subject in need thereof, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of treating a disease or condition characterized by hyperphosphorylation of tau in the brain, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

DETAILED DESCRIPTION

Described herein are compounds that are useful treating various diseases, disorders and medical conditions, including but not limited to those associated with proteins that are modified by O-GlcNAcase.

In a first embodiment, a compound of the present invention is represented by the following structural formula:

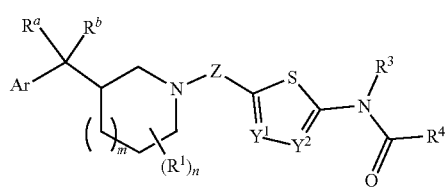

(I'')

or a pharmaceutically acceptable salt thereof, wherein the variables are as defined in the summary above.

In a second embodiment, a compound of the present invention is represented by the following structural formula:

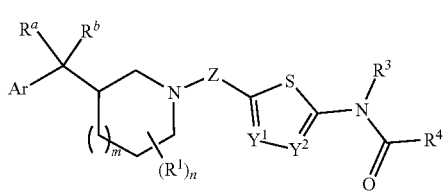

(I)

or a pharmaceutically acceptable salt thereof, wherein $R^a$, $R^b$ and $R^c$ are each independently —H, halo, $C_1$-$C_4$ alkyl, or $C_1$-$C_4$ haloalkyl, or $R^a$ and $R^b$ taken together with their intervening carbon atom form a $C_3$-$C_6$ cycloalkyl; wherein the remaining variables are as defined in the first embodiment.

In a third embodiment, a compound of the invention is represented by the following structural formulas:

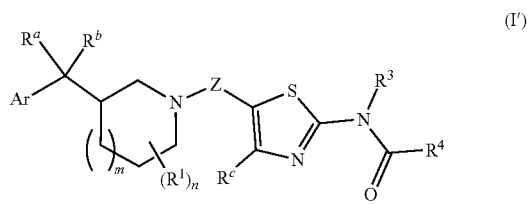

(I')

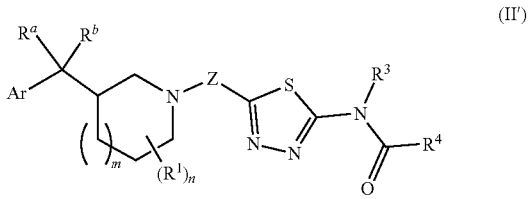

(II')

or a pharmaceutically acceptable salt thereof; wherein the variables are as defined in the first or second embodiments.

In a fourth embodiment, a compound of the invention is represented by the following structural formulas:

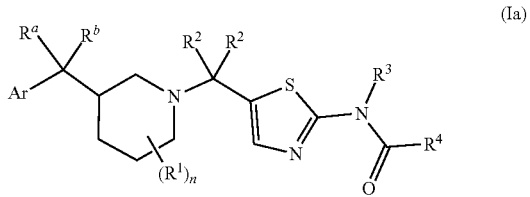

(Ia)

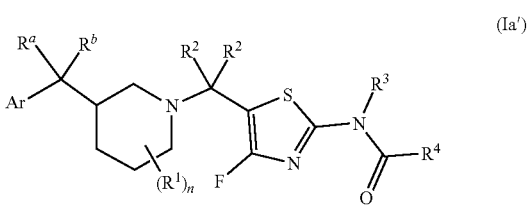

(Ia')

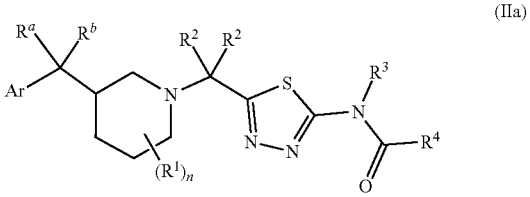

(IIa)

or a pharmaceutically acceptable salt thereof; wherein $R^a$ and $R^b$ are each independently —H or $C_1$-$C_4$ alkyl; $R^2$, for each occurrence, is independently —H, halo, $C_1$-$C_4$ alkyl; and the remaining variables are as defined in the first, second, or third embodiments.

In a fifth embodiment, a compound of the invention is represented by the following structural formulas:

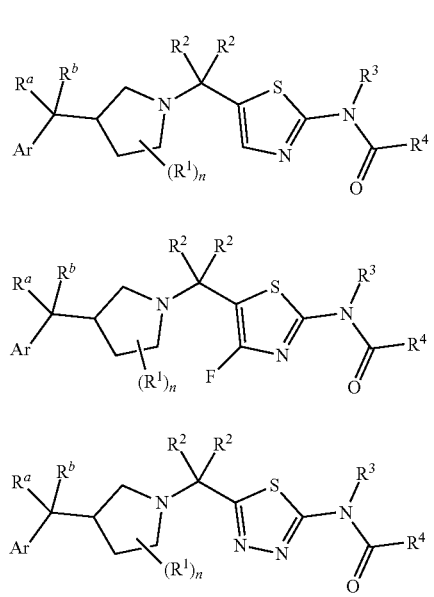

(Ib)

(Ib′)

(IIb)

or a pharmaceutically acceptable salt thereof; wherein $R^2$, for each occurrence, is independently —H, halo, $C_1$-$C_4$ alkyl; and the remaining variables are as defined in the first, second, or third embodiments.

In a sixth embodiment, a compound of the invention is represented by the following structural formulas:

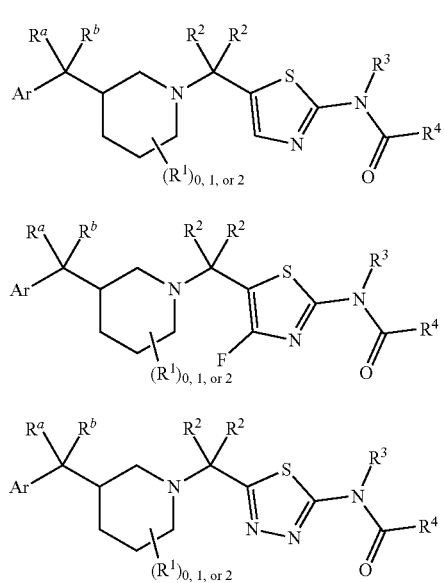

(Ia1)

(Ia1′)

(IIa1)

or a pharmaceutically acceptable salt thereof; wherein $R^a$ and $R^b$ are each independently —H or methyl; $R^1$ is halo, $C_1$-$C_4$ alkyl or $C_1$-$C_4$ haloalkyl; $R^2$, for each occurrence, is independently —H or $C_1$-$C_4$ alkyl; and the remaining variables are as defined in the first, second, third, or fourth embodiments.

In a seventh embodiment, a compound of the invention is represented by the following structural formulas:

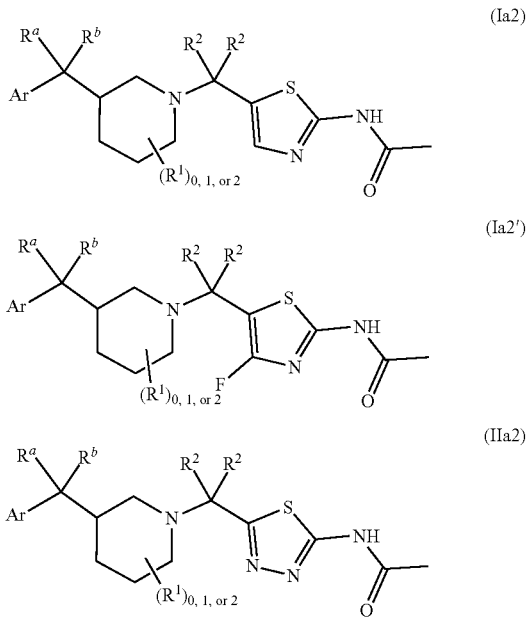

(Ia2)

(Ia2′)

(IIa2)

or a pharmaceutically acceptable salt thereof; wherein $R^a$ and $R^b$ are each independently —H or methyl; $R^2$, for each occurrence, is independently —H or methyl; $R^1$ is —F or methyl; and the remaining variables are as defined in the first, second, third, fourth or sixth embodiments.

In an eighth embodiment, a compound of the invention is represented by the following structural formulas:

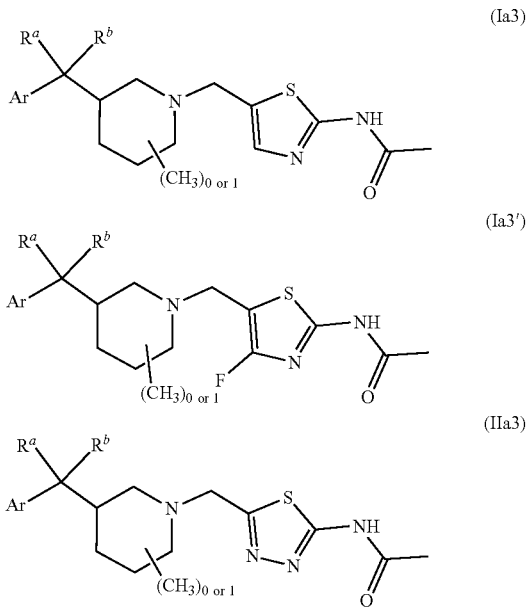

(Ia3)

(Ia3′)

(IIa3)

or a pharmaceutically acceptable salt thereof; wherein Ar is as defined in the first, second, third, fourth, sixth, or seventh embodiments.

In a ninth embodiment, a compound of the invention is represented by the following structural formulas:

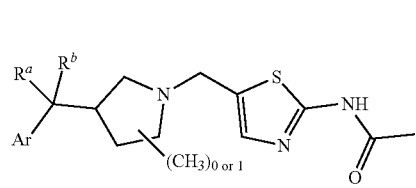
(Ib1)

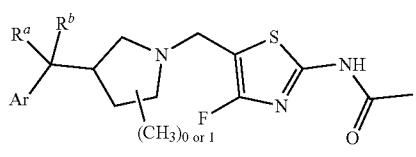
(Ib1')

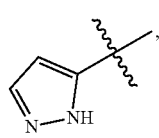 [SMILES: *c1ccn[nH]1]
(IIb1)

or a pharmaceutically acceptable salt thereof; wherein Ar is as defined in the first, second, third, or fifth embodiments.

In a tenth embodiment, in a compound of the invention in accordance to the first, second, third, fourth, fifth, sixth, seventh, eighth, or ninth embodiments, or a pharmaceutically acceptable salt thereof, Ar is optionally substituted pyrazolyl, optionally substituted imidazolyl, optionally substituted thiazolyl, optionally substituted phenyl, optionally substituted pyridinyl, optionally substituted pyrimidinyl, optionally substituted pyrazinyl, optionally substituted imidazo[1,2-a]pyridinyl, optionally substituted thieno[2,3-d]pyrimidinyl, or optionally substituted thieno[3,2-d]pyrimidinyl. In a compound of the invention in accordance to the first, second, third, fourth, fifth, sixth, seventh, eighth, or ninth embodiments, or a pharmaceutically acceptable salt thereof, Ar is optionally substituted oxadiazolyl, optionally substituted 1,2,3-triazol-1-yl, optionally substituted triazolo[4,3-a]pyridin-3-yl, or optionally substituted 1H-benzo[d]imidazol-1-yl.

In an eleventh embodiment, in a compound of the invention in accordance to the first, second, third, fourth, fifth, sixth, seventh, eighth, ninth, or tenth embodiments, or a pharmaceutically acceptable salt thereof, Ar is optionally substituted optionally substituted

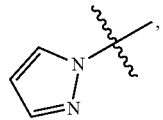 [SMILES: *n1cccn1], optionally substituted

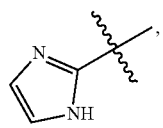 [SMILES: *c1ncc[nH]1], optionally substituted

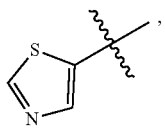 [SMILES: *c1cncs1], optionally substituted

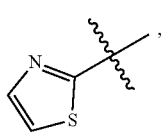 [SMILES: *c1nccs1], optionally substituted

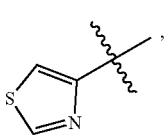, optionally substituted

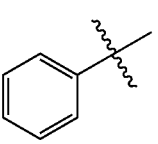, optionally substituted

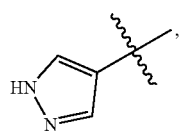, optionally substituted

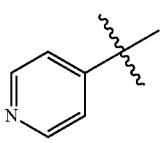, optionally substituted

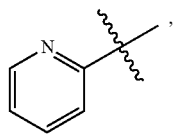 [SMILES: *c1ccccn1], optionally substituted

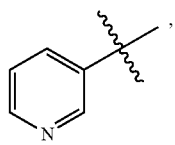 [SMILES: *c1cccnc1], optionally substituted

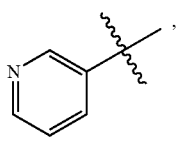 [SMILES: *c1cccnc1], optionally substituted

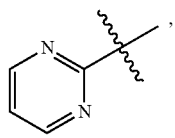 [SMILES: *c1ncccn1], optionally substituted

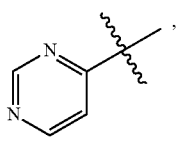 [SMILES: *c1ccncn1], optionally substituted

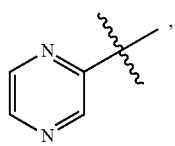 [SMILES: *c1cnccn1], optionally substituted

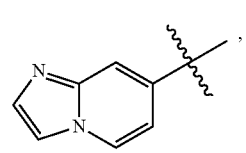 [SMILES: *c1ccn2ccnc2c1], or optionally substituted

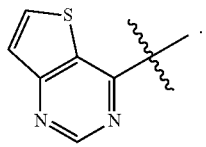 [SMILES: *c1ncnc2ccsc12].

In a compound of the invention in accordance to the first, second, third, fourth, fifth, sixth, seventh, eighth, ninth, or tenth embodiments, or a pharmaceutically acceptable salt thereof, Ar is optionally substituted

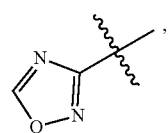 [SMILES: *c1ncon1], optionally substituted

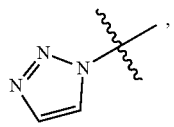 [SMILES: *n1ccnn1], optionally substituted

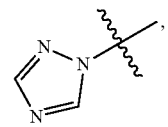 [SMILES: *n1cncn1], optionally substituted

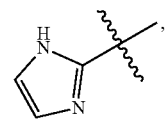 [SMILES: *c1ncc[nH]1], optionally substituted

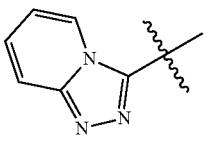, or optionally substituted

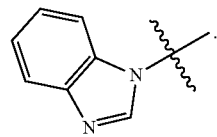 [SMILES: *n1cnc2ccccc21]

In a twelfth embodiment, in a compound of the invention in accordance to the first, second, third, fourth, fifth, sixth, seventh, eighth, ninth, tenth, or eleventh embodiments, or a pharmaceutically acceptable salt thereof, Ar is optionally substituted

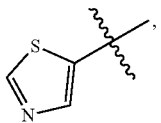 [SMILES: *c1cncs1]

optionally substituted

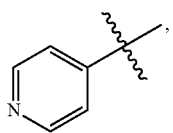 [SMILES: *c1ccncc1]

optionally substitute

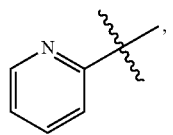

optionally substitute

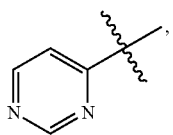

optionally substituted

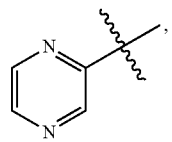 [SMILES: *c1cnccn1]

optionally substituted

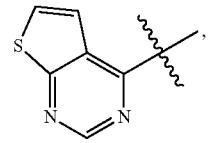 [SMILES: *c1ncnc2sccc12]

or optionally substituted

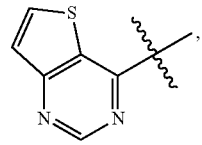 [SMILES: *c1ncnc2ccsc12]

In a compound of the invention in accordance to the first, second, third, fourth, fifth, sixth, seventh, eighth, ninth, tenth, or eleventh embodiments, or a pharmaceutically acceptable salt thereof, Ar is optionally substituted

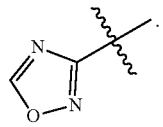

In a thirteenth embodiment, in a compound of the invention in accordance to the first, second, third, fourth, fifth, sixth, seventh, eighth, ninth, tenth, eleventh, or twelfth embodiments, or a pharmaceutically acceptable salt thereof, Ar is optionally substituted with one or more groups selected from $C_1$-$C_4$ alkyl, $C_1$-$C_4$ haloalkyl, $C_3$-$C_6$ cycloalkyl, halo, —CN, —$NO_2$, —$OR^z$, —$NR^xR^y$, —$S(O)_iR^x$, —$NR^xS(O)_i$ $R^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$ (=O)$R^y$, —C(=S)$NR^xR^y$, —$NR^xC$(=S)$R^y$, —$NR^x$(C=O) $OR^y$, —O(C=O)$NR^xR^y$, —NR(C=S)$OR^y$, —O(C=S) $NR^xR^y$, —$NR^x$(C=O)$NR^xR^y$, —$NR^x$(C=S)$NR^xR^y$, —C(=S)$R^x$, —C(=O)$R^x$, phenyl and monocyclic heteroaryl;

wherein
the $C_1$-$C_4$ alkyl group substituent on Ar is optionally substituted with —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^x$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O) $OR^y$, —O(C=O)$NR^xR^y$, —$NR^x$(C=S)$OR^y$, —O(C=S)$NR^xR^y$, —$NR^x$(C=O)$NR^xR^y$, —NR (C=S)$NR^xR^y$, —C(=S)$R^x$, and —C(=O)$R^y$,
$C_3$-$C_6$ cycloalkyl (optionally substituted with one or more groups selected from —$CH_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy);

the C$_3$-C$_6$ cycloalkyl, phenyl and monocyclic heteroaryl group substituent on Ar are optionally and independently substituted with C$_1$-C$_4$alkyl, C$_1$-C$_4$haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR(C=O)OR$^y$, —O(C=O)NR$^x$R$^y$, —NR$^x$(C=S)OR$^y$, —O(C=S)NR$^x$R$^y$, —NR(C=O)NR$^x$R$^y$, —NR$^x$(C=S)NR$^x$R$^y$, —C(=S)R$^x$, and —C(=O)R$^x$;

each R$^x$ and each R$^y$ is independently —H, C$_1$-C$_4$ alkyl, or C$_3$-C$_8$ cycloalkyl; wherein the C$_1$-C$_4$ alkyl or C$_3$-C$_8$ cycloalkyl represented by R$^x$ or R$^y$ is optionally substituted with one or more substituents selected from halo, hydroxyl, C$_3$-C$_6$ cycloalkyl and phenyl (optionally substituted with one or more groups selected from —CH$_3$, halomethyl, halo, methoxy or halomethoxy);

R$^z$ is —H, C$_1$-C$_4$ alkyl, or C$_3$-C$_8$ cycloalkyl; wherein the C$_1$-C$_4$ alkyl or C$_3$-C$_8$ cycloalkyl group represented by R$^z$ is optionally substituted with one or more substituents selected from halo, hydroxyl, C$_3$-C$_6$ cycloalkyl and phenyl (optionally substituted with one or more groups selected from —CH$_3$, halomethyl, halo, methoxy and halomethoxy); and i is 0, 1, or 2.

In a fourteenth embodiment, in a compound of the invention in accordance to the first, second, third, fourth, fifth, sixth, seventh, eighth, ninth, tenth, eleventh, twelfth, or thirteenth embodiments, or a pharmaceutically acceptable salt thereof, Ar is optionally substituted with one with one or more groups selected from C$_1$-C$_4$ alkyl, C$_1$-C$_4$haloalkyl, C$_3$-C$_6$ cycloalkyl, halo, —CN, —OR$^z$, —NR$^x$R$^y$, —C(=O)NR$^x$R$^y$, —C(=S)NR$^x$R$^y$, —O(C=O)NR$^x$R$^y$, —O(C=S)NR$^x$R$^y$, —C(=O)OR$^x$, —NR$^x$C(=O)R$^y$ phenyl, —C(=O)R$^x$, and optionally substituted monocyclic heteroaryl.

In a fifteenth embodiment, in a compound of the invention in accordance to the first, second, third, fourth, fifth, sixth, seventh, eighth, ninth, tenth, eleventh, twelfth, thirteenth, or fourteenth embodiments, or a pharmaceutically acceptable salt thereof, Ar is optionally substituted with one with one or more groups selected from C$_1$-C$_4$ alkyl, C$_1$-C$_4$ haloalkyl, C$_3$-C$_6$ cycloalkyl, halo, —OR$^z$, —C(=O)R$^x$, and monocyclic heteroaryl optionally substituted with C$_1$-C$_4$ alkyl, C$_1$-C$_4$haloalkyl, halo.

In a sixteenth embodiment, in a compound of the invention in accordance to the first, second, third, fourth, fifth, sixth, seventh, eighth, ninth, tenth, eleventh, twelfth, thirteenth, fourteenth, or fifteenth embodiments, or a pharmaceutically acceptable salt thereof, Ar is optionally substituted with one with one or more groups selected from —CH$_3$, —CH$_2$CH$_3$, halomethyl, cyclopentyl, cyclobutyl, halo, —OR$^z$, —C(=O)R$^x$, and a 5- or 6-membered monocyclic heteroaryl containing one or two heteroatoms selected from S and N and optionally substituted with C$_1$-C$_4$ alkyl; wherein R$^x$ is —H or C$_1$-C$_4$ alkyl; and wherein R is optionally substituted C$_1$-C$_4$ alkyl.

In a seventeenth embodiment, in a compound of the invention in accordance to the first, second, third, fourth, fifth, sixth, seventh, eighth, ninth, tenth, eleventh, twelfth, thirteenth, fourteenth, fifteenth, or sixteenth embodiment, or a pharmaceutically acceptable salt thereof, Ar is optionally substituted with one with one or more groups selected from —CH$_3$, —CH$_2$CH$_3$, —CHF$_2$, —CF$_3$, cyclopentyl, cyclobutyl, —F, —Cl, —Br, —OCH$_3$, —C(=O)CH$_3$, and a thiazolyl. In another embodiment, n a compound of the invention in accordance to the first, second, third, fourth, fifth, sixth, seventh, eighth, ninth, tenth, eleventh, twelfth, thirteenth, fourteenth, fifteenth, or sixteenth embodiment, or a pharmaceutically acceptable salt thereof, Ar is optionally substituted with one with one or more groups selected from —CH$_3$, —CH$_2$CH$_3$, —CHF$_2$, —CF$_3$, cyclopentyl, cyclobutyl, —F, —Br, —OCH$_3$, —C(=O)CH$_3$, and a thiazolyl.

In an eighteenth embodiment, a compound of the invention is represented by the following structural formula:

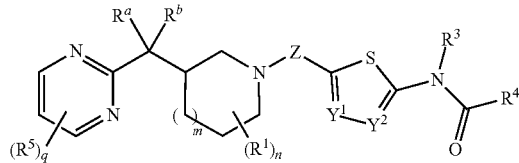

(III)

or a pharmaceutically acceptable salt thereof, wherein R$^5$, for each occurrence, is selected from C$_1$-C$_4$ alkyl, C$_1$-C$_4$ haloalkyl, C$_3$-C$_6$ cycloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR(C=S)OR, —O(C=S)NR$^x$R$^y$, —NR(C=O)NR$^x$R$^y$, —NR$^x$(C=S)NR$^x$R$^y$, —C(=S)R$^x$, —C(=O)R$^x$, phenyl and monocyclic heteroaryl;

wherein when R$^5$ is a C$_1$-C$_4$ alkyl group, the C$_1$-C$_4$ alkyl group is optionally and independently substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^x$, —NR$^x$(C=O)NR$^x$R$^y$, —O(C=O)NR$^x$R$^y$, —NR$^x$(C=S)OR$^y$, —O(C=S)NR$^x$R$^y$, —NR$^x$(C=O)NR$^x$R$^y$, —NR(C=S)NR$^x$R$^y$, —C(=S)R$^x$, and —C(=O)R$^y$, C$_3$-C$_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy);

when R$^5$ is a C$_3$-C$_6$ cycloalkyl, phenyl or a monocyclic heteroaryl, the cycloalkyl, phenyl or a monocyclic heteroaryl is optionally and independently substituted with C$_1$-C$_4$ alkyl, C$_1$-C$_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR(C=O)OR$^y$, —O(C=O)NR$^x$R$^y$, —NR$^x$(C=S)OR$^y$, —O(C=S)NR$^x$R$^y$, —NR(C=O)NR$^x$R$^y$, —NR$^x$(C=S)NR$^x$R$^y$, —C(=S)R$^x$, and —C(=O)R$^x$;

each $R^x$ and each $R^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by $R^x$ or $R^y$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy or halomethoxy);

$R^z$ is —H, $C_1$-$C_4$ alkyl, or $C_3$-$C_8$ cycloalkyl; wherein the $C_1$-$C_4$ alkyl or $C_3$-$C_8$ cycloalkyl group represented by $R^z$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy and halomethoxy); and i is 0, 1, or 2; and q 0, 1, 2, or 3;

wherein the remaining variables are as defined in the first embodiment.

In a nineteenth embodiment, a compound of the invention is represented by the one of the following structural formulas:

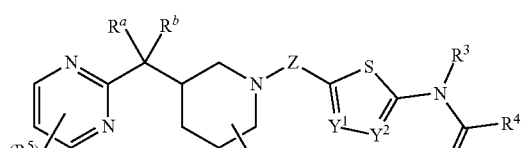

(IIIa)

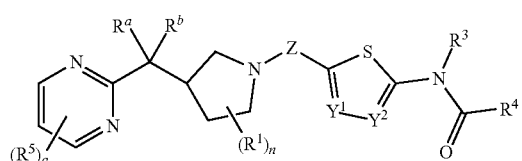

(IIIb)

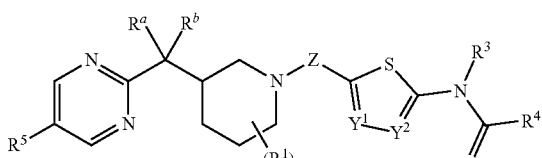

(IIIc)

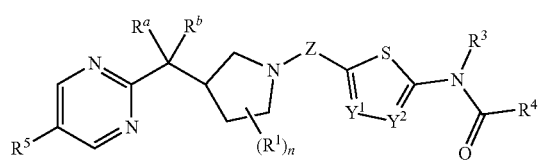

(IIId)

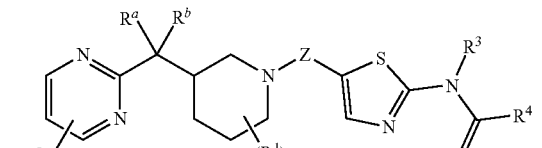

(IIIe)

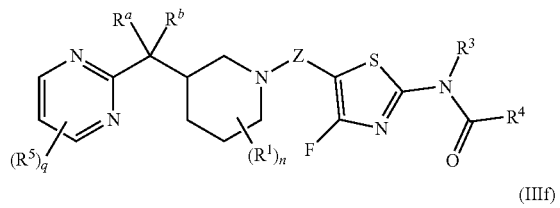

(IIIe')

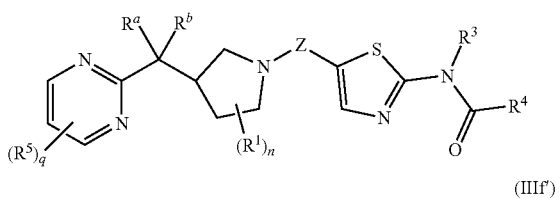

(IIIf)

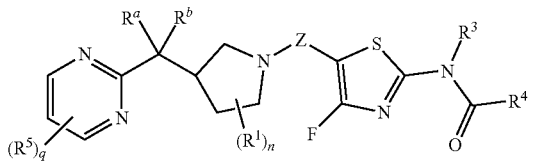

(IIIf')

or a pharmaceutically acceptable salt thereof, wherein q is 0, 1, 2, or 3; and wherein the remaining variables are as defined in the eighteenth embodiment.

In a twentieth embodiment, a compound of the invention is represented by the one of the following structural formulas:

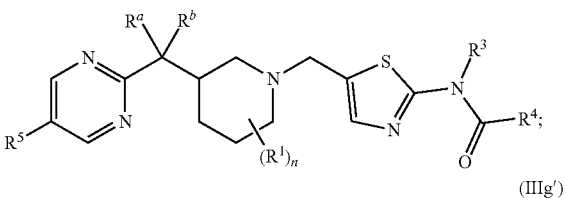

(IIIg)

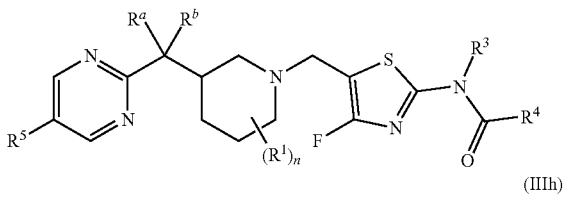

(IIIg')

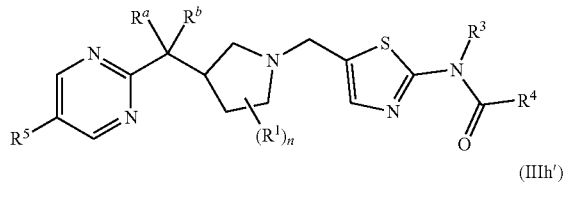

(IIIh)

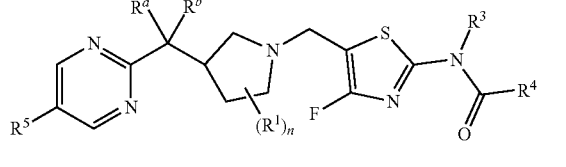

(IIIh')

or a pharmaceutically acceptable sale thereof, wherein the remaining variables are as defined in the eighteenth embodiment.

In a twenty-first embodiment, a compound of the invention is represented by the following structural formula:

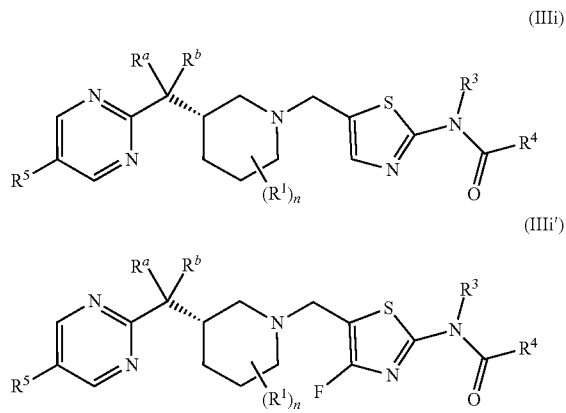

(IIIi)

(IIIi')

or a pharmaceutically acceptable salt thereof, wherein the remaining variables are as defined in the eighteenth embodiment.

In a twenty-second embodiment, a compound of the invention is represented by the following structural formula:

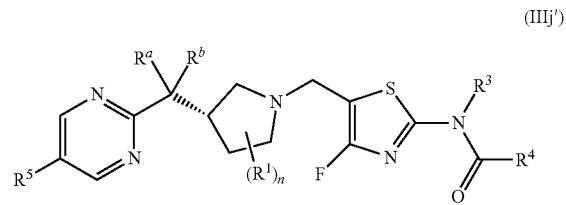

(IIIj')

or a pharmaceutically acceptable salt thereof, wherein the remaining variables are as defined in the eighteenth embodiment.

In a twenty-third embodiment, a compound of the invention is represented by the following structural formula:

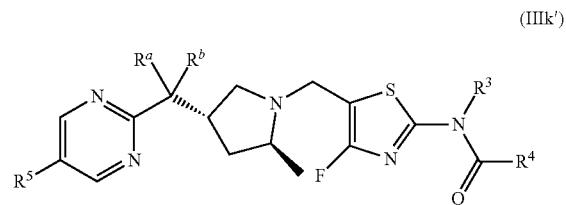

(IIIk')

or a pharmaceutically acceptable salt thereof, wherein the remaining variables are as defined in the eighteenth embodiment.

In a twenty-fourth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment, or a pharmaceutically acceptable salt thereof, $R^3$ is —H, In a twenty-fifth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment, or a pharmaceutically acceptable salt thereof, $R^4$ is —CH$_3$, In a twenty-fourth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth nineteenth, twentieth, twenty-first, twenty-second, or twenty-third embodiments, or a pharmaceutically acceptable salt thereof, $R^5$ is selected from $C_1$-$C_4$ alkyl, $C_1$-$C_4$haloalkyl, $C_3$-$C_6$ cycloalkyl, halo, —CN, —OR$^z$, —NR$^x$R$^y$, —C(=O) NR$^x$R$^y$, —C(=S)NR$^x$R$^y$, —O(C=O)NR$^x$R$^y$, —O(C=S) NR$^x$R$^y$, —C(=O)OR$^x$, —NR$^x$C(=O)R$^y$ phenyl, —C(=O) R$^x$, and optionally substituted monocyclic heteroaryl.

In a twenty-fifth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth nineteenth, twentieth, twenty-first, twenty-second, twenty-third, or twenty-fourth embodiments, or a pharmaceutically acceptable salt thereof, $R^5$ is selected from $C_1$-$C_4$ alkyl, $C_1$-$C_4$haloalkyl, $C_3$-$C_6$ cycloalkyl, halo, —OR$^z$, —C(=O)R$^x$, and monocyclic heteroaryl optionally substituted with $C_1$-$C_4$ alkyl, $C_1$-$C_4$haloalkyl, halo.

In a twenty-sixth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiments, or a pharmaceutically acceptable salt thereof, $R^5$ is selected from —CH$_3$, —CH$_2$CH$_3$, halomethyl, cyclopentyl, cyclobutyl, halo, —OR$^z$, —C(=O)R$^x$, and a 5- or 6-membered monocyclic heteroaryl containing one or two heteroatoms selected from S and N and optionally substituted with $C_1$-$C_4$ alkyl; wherein $R^5$ is —H or $C_1$-$C_4$ alkyl; and wherein $R^z$ is optionally substituted $C_1$-$C_4$ alkyl.

In a twenty-seventh embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth embodiment, or a pharmaceutically acceptable salt thereof, R is selected from —CH$_3$, —CH$_2$CH$_3$, —CHF$_2$, —CF$_3$, cyclopentyl, cyclobutyl, —F, —Br, —Cl, —OCH$_3$, —C(=O)CH$_3$, and a thiazolyl.

In a twenty-eighth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment, or a pharmaceutically acceptable salt thereof, R is selected from —F, —Br, and Cl.

In a twenty-ninth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, or twenty-eighth embodiment, or a pharmaceutically acceptable salt thereof, one of $R^a$ and $R^b$ is —H and the other is selected from —CH$_3$, —CF$_3$, and —OCH$_3$.

In a thirtieth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth embodiment, or a pharmaceutically acceptable salt thereof, n is 0 or 1.

In one embodiment, a compound of the invention may be any one of the compounds described herein in the working examples, including salts and neutral forms thereof.

As used herein, the term "alkyl" refers to a fully saturated branched or straightchained hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkoxy" refers to the group —OR, in which R is an alkyl or a cycloalkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O-cyclopentyl and —O-cyclohexyl.

The number of carbon atoms in a group is specified herein by the prefix "$C_{x-xx}$", wherein x and xx are integers. For example, "$C_4$ alkyl" is an alkyl group which has from 1 to 4 carbon atoms.

As used herein, the term "halogen" or "halo" may be fluoro, chloro, bromo or iodo.

As used herein, the term "haloalkyl" refers to an alkyl, as defined herein, that is substituted by one or more halo groups as defined herein.

As used herein, the terms "heterocyclyl", "heterocyclyl group", "heterocyclic" and "heterocyclic ring" are used interchangeably to refer to a saturated, unsaturated non-aromatic, monocyclic or bicyclic (e.g., fused) ring system which has from 3- to 12-ring members, or in particular 3- to 6-ring members or 5- to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(=O)), N can be oxidized (e.g., N(O)) or quaternized (e.g. N+), and S can be optionally oxidized to sulfoxide and sulfone. Examples of non-aromatic heterocyclyls include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and the like. Examples of bicyclic nonaromatic heterocyclic ring systems include benzo[1,3]dioxolyl, tetrahydroindolyl, and 2-azaspiro[3.3]heptanyl, and the like.

As used herein, the terms "heteroaryl", "heteroaryl group", "heteroaromatic" and "heteroaromatic ring" are used interchangeably to refer to an aromatic 5- to 12-membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone.

"Heteroaryl" includes a heteroaromatic group that is fused to a phenyl group or non-aromatic heterocycle such as tetrahydrofuran, pyran, pyrrolidine, piperidine, and the like. As used herein, the heteroaryl group Ar can be attached to the rest of a compound of the invention at any ring that has an open valency. Examples of heteroaryls include pyrrolyl, furanyl, imidazolyl, pyrazolyl, oxazolyl, isoxazolyl, thiazolyl, isothiazolyl, oxadiazolyl, thiadiazolyl, triazolyl, tetrazolyl, pyridyl, pyrazinyl, pyrimidyl, pyridazinyl, oxazinyl, thiazinyl, dioxinyl, triazinyl, tetrazinyl, azepinyl, oxepinyl, thiepinyl, thiazepinyl, 1-oxo-pyridyl, thienyl, valerolactamyl, azaindolyl, benzimidazolyl, benzo[1,4]dioxinyl, benzofuryl, benzoisoxazolyl, benzoisothiazolyl, benzothiadiazolyl, benzothiazolyl, benzothienyl, benzotriazolyl, benzoxadiazolyl, benzoxazolyl, cyclopentaimidazolyl, cyclopentatriazolyl, imidazo[1,2-a]pyridyl, indazolyl, indolizinyl, indolyl, isoquinolinyl, oxazolopyridinyl, purinyl, pyrazolo[3,4]pyrimidinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinolinyl, thiazolopyridinyl, napthyridyl, and the like.

As used herein the term "an optionally substituted phenyl fused to an optionally substituted non-aromatic 5- to 6-membered heterocycle" refers to the fused ring system where it is the phenyl ring that is that is directly linked to the rest of the compound.

As used herein, the term "cycloalkyl" refers to completely saturated monocyclic or bicyclic (e.g., fused) hydrocarbon groups of 3-12 carbon atoms, 3-6 carbon atoms or 5-7 carbon atoms.

As used herein, the term "halocycloalkyl" refers to a cycloalkyl, as defined herein, that is substituted by one or more halo groups as defined herein.

The term "fused ring system," as used herein, is a ring system having at least two rings and in which two rings share two adjacent ring atoms.

A substituted alkyl, phenyl, heteroaryl, non-aromatic heterocyclyl or heterocyclyl group is an alkyl, phenyl, heteroaryl, non-aromatic heterocyclyl or heterocyclyl group that has one or more substituents. Suitable substituents are those that do not significantly decrease the O-GlcNAcase inhibitory activity of a compound of formula (I"), (I), (I'), (Ia), (Ia') (b), (b') (Ia1), (Ia1'), (Ia2), (Ia2'), (Ia3), (Ia3'), (Ib1), (Ib1'), (II'), (IIa), (IIb), (IIa1), (IIa2), (IIa3), (IIb1), (III), (IIa), (IIIb), (IIIc), (IIId), (IIe), (IIIe'), (IIIf), (IIIf'), (IIIg), (IIIg'), (IIIh), (IIIh'), (IIi), (IIIi'), (IIIj'), (IIIk') (hereinafter referred thereto collectively as "formulas (I") through (IIIk")") or a pharmaceutically acceptable salt thereof. Examples of suitable substituents for an alkyl, phenyl, heteroaryl, non-aromatic heterocyclyl or heterocyclyl group include but are not limited to $C_1$-$C_4$ alkyl, $C_1$-$C_4$ haloalkyl, $C_3$-$C_6$ cycloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl. The $C_1$-$C_4$ alkyl group substituent is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=O)OR$^y$, —O(C=O)NR$^x$R$^y$, —NR(C=S)OR$^y$, —O(C=S)NR$^x$R$^y$, —NR(C=O)NR$^x$R$^y$, —NR$^x$(C=S)NR$^x$R$^y$, —C(=S)R$^x$, and —C(=O)R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy). The C$_3$-C$_6$ cycloalkyl, phenyl and monocyclic heteroaryl group substituents are optionally and independently substituted with C$_1$-C$_4$ alkyl, C$_1$-C$_4$haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(═O)OR$^x$, —OC(═O)OR$^x$, —C(═S)OR$^x$, —O(C═S)R$^y$, —C(═O)NR$^x$R$^y$, —NR$^x$C(═O)R$^y$, —C(═S)NR$^x$R$^y$, —NR$^x$C(═S)R$^y$, —NR$^x$(C═O)OR$^y$, —O(C═O)NR$^x$R$^y$, —NR(C═S)OR$^y$, —O(C═S)NR$^x$R$^y$, —NR(C═O)NR$^x$R$^y$, —NR$^x$(C═S)NR$^x$R$^y$, —C(═S)R$^x$, and —C(═O)R. In these substituents, each R$^x$ and each R$^y$ is independently —H, C$_1$-C$_4$ alkyl, or C$_3$-C$_8$ cycloalkyl, where the C$_1$-C$_4$ alkyl or C$_3$-C$_8$ cycloalkyl represented by R$^x$ or R$^y$ is optionally substituted with one or more substituents selected from halo, hydroxyl, C$_3$-C$_6$ cycloalkyl and phenyl (optionally substituted with one or more groups selected from —CH$_3$, halomethyl, halo, methoxy or halomethoxy). In these substituents, R$^z$ is —H, C$_1$-C$_4$ alkyl, or C$_3$-C$_8$ cycloalkyl, where the C$_1$-C$_4$ alkyl or C$_3$-C$_8$ cycloalkyl group represented by R$^z$ is optionally substituted with one or more substituents selected from halo, hydroxyl, C$_3$-C$_6$ cycloalkyl and phenyl (optionally substituted with one or more groups selected from —CH$_3$, halomethyl, halo, methoxy and halomethoxy). In these substituents, i is 0, 1, or 2.

Pharmaceutically acceptable salts of the compounds disclosed herein are also included in the invention. In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Suitable bases include but are not limited to alkali metal hydroxides, alkaline earth metal hydroxides, carbonates, bicarbonates, and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase).

The disclosed compounds may exist in tautomeric forms and mixtures and separate individual tautomers are contemplated. In addition, some compounds may exhibit polymorphism.

When a particular steroisomer (e.g., enantiomer, diastereomer, etc.) of a compound used in the disclosed methods is depicted by name or structure, the stereochemical purity of the compounds is at least 60%, 70%, 80%, 90%, 95%, 97%, 99%, 99.5% or 99.9%. "Stererochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The term "Peak 1" as used herein refers to the first eluding peak during the separation of enantiomers and/or diastereomers, which is followed by the subsequently eluding "Peak 2", and optionally, "Peak 3", and "Peak 4".

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

One aspect of the invention includes a method for inhibiting a glycosidase and/or a glycosidase signaling pathway in a cell, the method comprising contacting the cell with an effective amount of a compound of any one of formulas (I") through (IIIk') or a pharmaceutically acceptable salt thereof. The glycosidase is preferably a glycoside hydrolase, more preferably a family 84 glycoside hydrolase, even more preferably O-glycoprotein-2-acetamido-2-deoxy-3-D-glucopyranosidase (0-GlcNAcase or OGA), most preferably a mammalian O-GlcNAcase. In one embodiment, the cell is contacted in vitro or in vivo. In one embodiment, contacting the cell includes administering the compound to a subject.

One aspect of the invention includes a method for inhibiting a glycosidase and/or a glycosidase signaling pathway in a subject in need thereof, the method comprising administering to the subject, a therapeutically effective amount of a compound of any one of formulas (I") through (IIIk') or a pharmaceutically acceptable salt thereof, thereby activating the glycosidase in the subject. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase.

One aspect of the invention includes a method for promoting survival of a eukaryotic cell (e.g., a mammalian cell) or increasing the lifespan of the cell, the method comprising administering to the subject a therapeutically effective amount of a compound of any one of formulas (I") through (IIIk') or a pharmaceutically acceptable salt thereof, thereby promoting survival of the eukaryotic cell or increasing the lifespan of the cell.

One aspect of the invention includes a method for treating a disease or a condition that is caused, mediated and/or propagated by O-GlcNAcase activity in a subject, the method comprising administering to the subject a therapeutically effective amount of a compound of any one of formulas (I") through (IIIk') or a pharmaceutically acceptable salt thereof. Preferably, the disease or condition is a neurological disorder, diabetes, cancer or stress. More preferably, the disease or condition is a neurological disorder. In one embodiment, the neurological disorder is one or more tauopathies selected from Acute ischemic stroke (AIS), Alzheimer's disease, Dementia, Anyotrophic lateral sclerosis (ALS). Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British derentia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-denenta complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-oily dementia, Huntington's disease, and Parkinson's disease. In another embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci). Argyrophilic grain dementia, epilepsy, mild cognitive impairment (MCI), Huntington's disease, and Parkinson's disease. In yet another embodiment, the neurological disorder is Alzheimer's disease.

One aspect of the invention includes a method for treating a disease or a condition that is characterized by hyperphosphorylation of tau (e.g., hyperphosphorylation of tau in the brain) in a subject, the method comprising administering to the subject a therapeutically effective amount of a compound of any one of formulas (I") through (IIIk') or a pharmaceutically acceptable salt thereof. In one embodiment, the disease or condition is selected from Acute ischemic stroke (AIS), Alzheimer's disease, Dementia, Amyotrophic lateral sclerosis (ALS). Amyotrophic lateral sclerosis with cognitive impairment (ALSci), Argyrophilic grain dementia, Bluit disease, Coricobasal degeneration (CBP), Dementia pugilistica, Diffuse neurofibrillary tangles with calcification, Down's syndrome, epilepsy, Familial British dementia, Familial Danish dementia, Frototemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD) Variant Creutzfeldt-Jakob Disease (vCJD), Fatal Familial Insomnia, Kuru, Progressive supercortical gliosis, Progressive supranuclear palsy (PSP). Steele-Richardson-Olszewski syndrome, Subacute sclerosing panencephalitis, Tangle-only dementia, Huntington's disease, and Parkinson's disease. In another embodiment, the disease or condition is selected from Acute ischemic stroke (AIS), Alzheimer's disease, Dementia, Anyotrophic lateral sclerosis (ALS), Amyotrophic lateral sclerosis with cognitive impairment (ALSci). Argyrophilic grain dementia, epilepsy, ischemic stroke, mild cognitive impairment (MCI), Huntington's disease, and Parkinson's disease. In yet another embodiment, the disease or condition is Alzheimer's disease.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; and delaying, inhibiting or decreasing the likelihood of the progression of the disease, disorder or syndrome.

The term "an effective amount" means an amount of the compound of any one of formulas (I") through (IIIk') or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of any one of formulas (I") through (IIIk') or a pharmaceutically acceptable salt thereof, reducing the likelihood of recurrence of a disease or condition treatable by a compound of any one of formulas (I") through (IIIk') or a pharmaceutically acceptable salt thereof or one or more symptoms thereof, e.g., as determined by clinical symptoms, compared to a control. The expression "an effective amount" also encompasses the amounts which are effective for increasing normal physiological function.

Another embodiment of the present invention is a pharmaceutical composition comprising at least one compound described herein, or a pharmaceutically acceptable salt thereof, and at least one pharmaceutically acceptable carrier.

Also included are the use of a compound of any one of formulas (I") through (IIIk') or a pharmaceutically acceptable salt thereof in the manufacture of a medicament for the treatment of one or more diseases or conditions described herein. Also included herein are pharmaceutical compositions comprising a compound of any one of formulas (I") through (IIIk') or a pharmaceutically acceptable salt thereof optionally together with a pharmaceutically acceptable carrier, in the manufacture of a medicament for the treatment of one or more diseases or conditions described herein. Also included is a compound of any one of formulas (I″) through (IIIk′) or a pharmaceutically acceptable salt thereof for use the treatment of a subject with one or more diseases or conditions described herein. Further included are pharmaceutical compositions comprising a compound of any one of formulas (I″) through (IIIk′) or a pharmaceutically acceptable salt thereof, optionally together with a pharmaceutically acceptable carrier, for use in the treatment of one or more diseases or conditions described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

A compound of any one of formulas (I″) through (IIIk′) or a pharmaceutically acceptable salt thereof, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

EXEMPLIFICATIONS

The following general reaction schemes, Schemes 1 to 4, provide useful details for preparing the instant compounds. The requisite intermediates are in some cases commercially available or can be prepared according to literature procedures. The illustrative reaction schemes are not limited by the compounds listed or by any particular substituents employed for illustrative purposes substituent labeling (i.e. R groups) as shown in the reaction schemes do not necessarily correlate to that used in the claims and often, for clarity, a single substituent is shown attached to the compound where multiple substituents are allowed under the definitions of any one of formulas (I″) through (IIIk′) hereinabove.

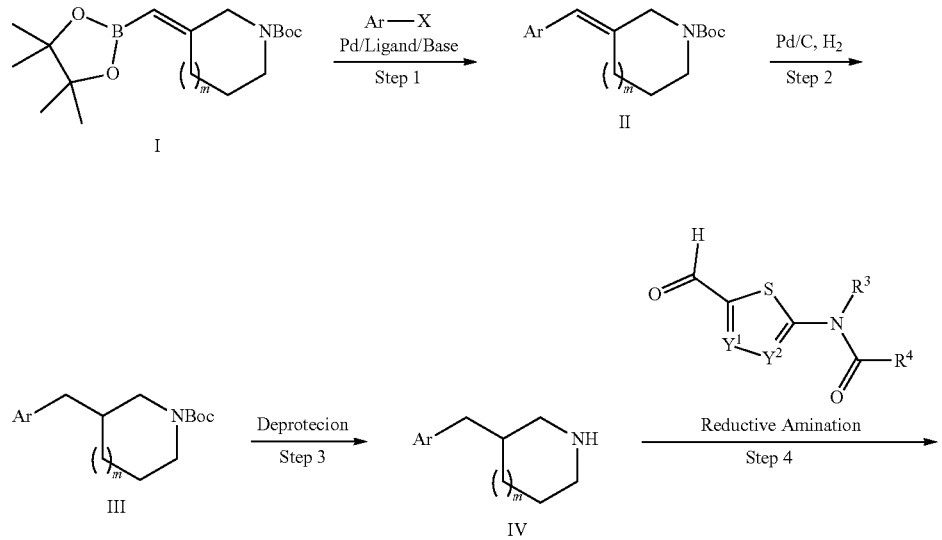

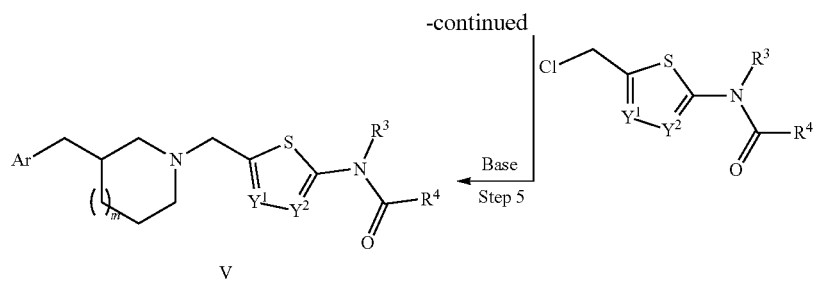

V

Intermediate 1

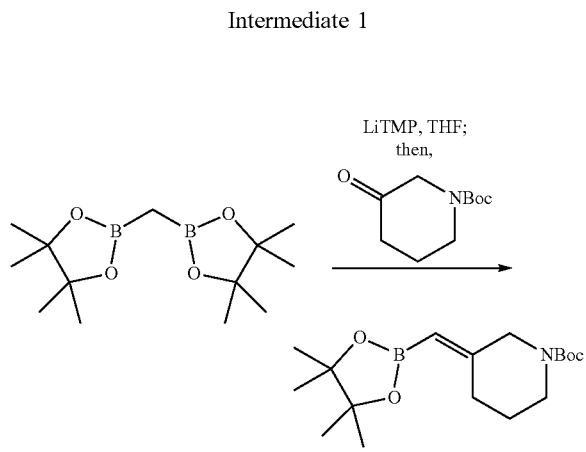

tert-butyl 3-((4,4,5,5-tetramethyl-1,3,2-dioxaborolan-2-yl)methylene)piperidine-1-carboxylate To a solution of 2,2,6,6-tetramethylpiperidine (85.0 g, 602 mmol) in anhydrous THF (1000 mL) at 0° C. was added a 2.5M solution of n-BuLi in hexanes (288 mL, 720 mmol) under argon. The resulting mixture was stirred for 10 min. A solution of 4,4,5,5-tetramethyl-2-[(tetramethyl 1,3,2-dioxaborolan-2-yl)methyl]-1,3,2-dioxaborolane (161 g, 601 mmol) in THF (200 mL) was added at 0° C. After stirring for 15 minutes, the solution was cooled to −78° C. before the dropwise addition of a solution of tert-butyl 3-oxopiperidine-1-carboxylate (100 g, 502 mmol) in THF (500 mL). The reaction was stirred for 1 h at −78° C. and then overnight at 0° C. A 30% $K_2CO_3$ (aq) solution (500 mL) was added and the organic layer was partitioned, dried over $Na_2SO_4$, filtered, and concentrated in vacuo. The residue was purified over $SiO_2$ (ethyl acetate/pentane) to afford the title compound (121 g, 75%).

Intermediate 2

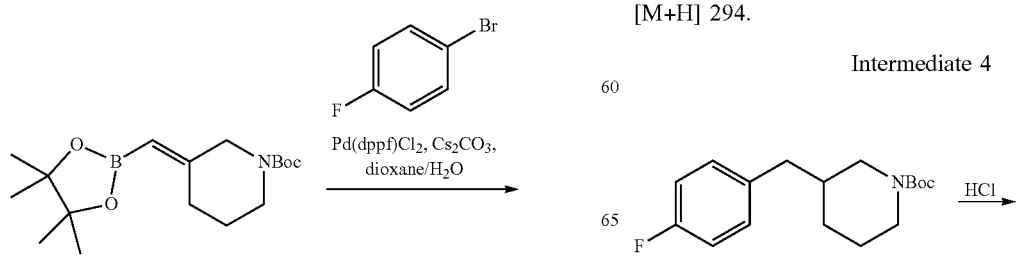

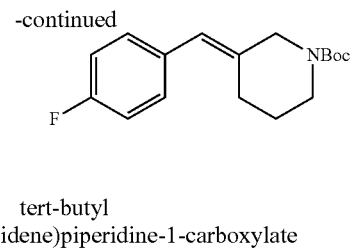

tert-butyl 3-(4-fluorobenzylidene)piperidine-1-carboxylate

To a solution of 1-bromo-4-fluorobenzene (0.2 g, 1.14 mmol) in dioxane (8.0 mL) and $H_2O$ (2.0 mL) were added 1 tert-butyl 3-((4,4,5,5-tetramethyl-1,3,2-dioxaborolan-2-yl)methylene)piperidine-1-carboxylate (0.405 g, 1.26 mmol), Pd(dppf)Cl$_2$ (0.084 g, 0.114 mmol), Cs$_2$CO$_3$ (0.745 g, 2.29 mmol). The mixture was stirred at 90° C. for 2.0 hours under $N_2$. The reaction mixture was filtered and concentrated in vacuo. The residue was purified over $SiO_2$ (petroleum ether/ EtOAc: 15/1) to afford the title compound (0.120 g, 36%). LCMS (ESI): [M+H] 292.

Intermediate 3

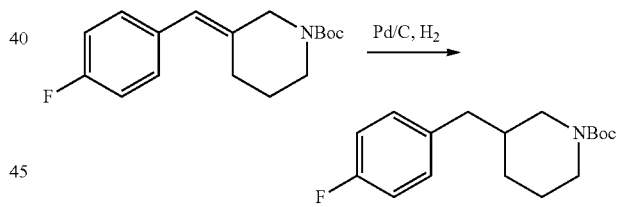

tert-butyl 3-(4-fluorobenzyl)piperidine-1-carboxylate

To a solution of tert-butyl 3-(4-fluorobenzylidene)piperidine-1-carboxylate (0.120 g, 0.412 mmol) in MeOH (15.0 mL) was added Pd/C (0.022 g, 10% on carbon) under $N_2$. The mixture was stirred at 20° C. for 1 hour under $H_2$ (15 psi). The mixture was filtered and concentrated in vacuo to afford the title compound (0.082 g, 68%). LCMS (ESI): [M+H] 294.

Intermediate 4

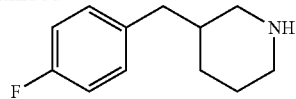

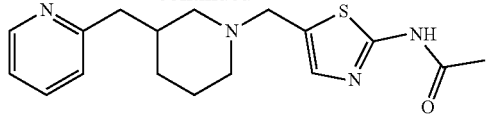

3-(4-fluorobenzyl)piperidine tert-Butyl 3-(4-fluorobenzyl)piperidine-1-carboxylate (0.082 g, 0.280 mmol) was added to a HCl/EtOAc solution (0.280 mmol, 8.0 mL). The mixture was stirred at 18° C. for 17 h. The mixture was adjusted to pH 8 with NH₄OH (aq) and the mixture was concentrated in vacuo to afford the title compound (0.054 g, 99%). LCMS (ESI): [M+H] 194.

Example 1-1

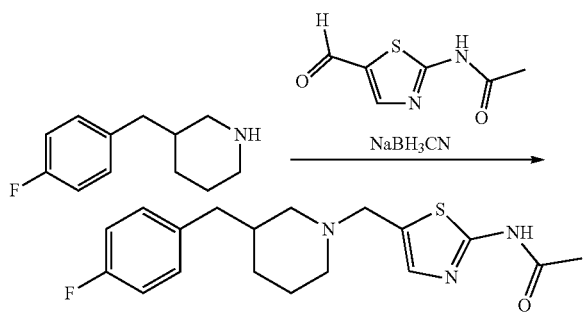

N-(5-((3-(4-fluorobenzyl)piperidin-1-yl)methyl)thiazol-2-yl)acetamide

To a solution of 3-(4-fluorobenzyl)piperidine (0.054 g, 0.279 mmol) in MeOH (15.0 mL) were added N-(5-formylthiazol-2-yl)acetamide (0.095 g, 0.559 mmol) and a drop of AcOH. The mixture was stirred at 50° C. for 2 h. NaBH₃CN (0.053 g, 0.838 mmol) was added and the mixture was stirred at 50° C. for 17 h. The mixture was purified by Prep-HPLC {(Column: Waters Xbridge Prep OBD C18 150×30 5 u; Condition: water (0.04% NH₃H₂O+10 mM NH₄HCO₃)-MeCN; Begin B: 35; End B: 65; Gradient Time (min): 10; 100% B Hold Time (min): 2; FlowRate (ml/min): 25} to afford the title compound (0.038 g, 39%). LCMS: [M+H] 348. ¹HNMR: (400 MHz, Methanol-d4) δ 7.19 (s, 1H), 7.14-7.10 (m, 2H), 6.94 (t, J=9.2 Hz, 2H), 3.65 (s, 2H), 2.83-2.75 (m, 2H), 2.48 (d, J=6.8 Hz, 2H), 2.19 (s, 3H), 2.02-1.99 (m, 1H), 1.82-1.66 (m, 4H), 1.57-1.47 (m, 1H), 0.99-0.91 (m, 1H).

Example 1-2

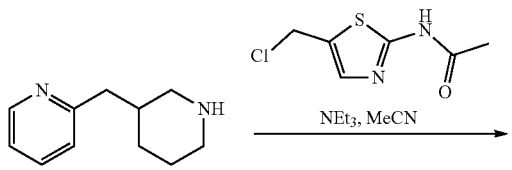

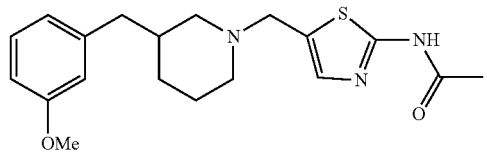

N-(5-((3-(pyridin-2-ylmethyl)piperidin-1-yl)methyl)thiazol-2-yl)acetamide

To a suspension of 2-(3-piperidylmethyl)pyridine HCl (0.035 g, 0.165 mol, hydrochloride) and N-[5-(chloromethyl)thiazol-2-yl]acetamide (0.032 g, 0.165 mmol) in MeCN (0.64 mL) was added triethylamine (0.05 g, 0.494 mol) and the mixture warmed to 70° C. overnight. The reaction was cooled to room temperature, and the mixture was diluted with EtOAc and washed with saturated NH₄Cl (aq). The organics were dried over MgSO₄, filtered and concentrated in vacuo. The residue was purified by Prep-HPLC {(Column: Waters XSelect CSH Prep C18 Sum OBD 19×100 mm; Condition: water:MeCN gradient 5-55% ACN over 7 min gradient, 0.1 Vol % ammonium hydroxide modifier} to afford the title compound (0.015 g, 27%). LCMS (ESI): [M+H] 331. ¹HNMR: (500 MHz, CDCl₃) δ 11.76 (br s, 1H), 8.45 (dd, J=1.8, 4.9 Hz, 1H), 8.40 (d, J=1.8 Hz, 1H), 7.47 (td, J=1.8, 7.9 Hz, 1H), 7.21 (dd, J=4.6, 7.0 Hz, 1H), 7.18 (s, 1H), 3.70-3.59 (m, 2H), 2.78 (br d, J=9.2 Hz, 2H), 2.60-2.53 (m, 1H), 2.51-2.43 (m, 1H), 2.31 (s, 3H), 2.07-1.98 (m, 1H), 1.93-1.81 (m, 2H), 1.66 (m, 2H), 1.56-1.46 (m, 1H), 1.02-0.91 (m, 1H).

Example 1-3

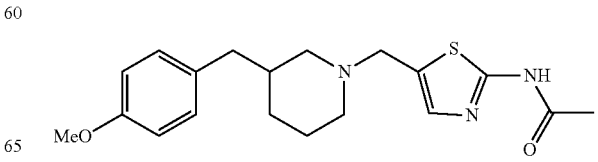

N-(5-((3-(3-methoxybenzyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 1-bromo-3-methoxybenzene, and N-(5-formylthiazol-2-yl)acetamide. LCMS (ESI): [M+H] 360. ¹HNMR: (400 MHz, Methanol-d4) δ 7.20 (s, 1H), 7.13 (t, J=8.0 Hz, 1H), 6.71-6.69 (m, 3H), 3.75 (s, 3H), 3.71-3.65 (m, 2H), 2.84-2.78 (m, 2H), 2.48-2.46 (m, 2H), 2.19 (s, 3H), 2.04-1.99 (m, 1H), 1.88-1.66 (m, 4H), 1.58-1.48 (m, 1H), 1.00-0.92 (m, 1H).

Example 1-4

N-(5-((3-(4-methoxybenzyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 1-chloro-4-methoxybenzene, and N-(5-formylthiazol-2-yl)acetamide. LCMS (ESI): [M+H] 360. ¹HNMR: (400 MHz, CDCl₃) δ 12.43 (s, 1H), 7.17 (s, 1H), 7.04 (d, J=8.4 Hz, 1H), 6.80 (d, J=8.4 Hz, 1H), 3.77 (s, 3H), 3.69-3.58 (m, 2H), 2.79-2.67 (m, 2H), 2.51-2.37 (m, 2H), 2.31 (s, 3H), 2.00-1.85 (m, 1H), 1.90-1.76 (m, 2H), 1.71-1.57 (m, 2H), 1.54-1.48 (m, 1H), 0.94-0.86 (m, 1H).

Example 1-5

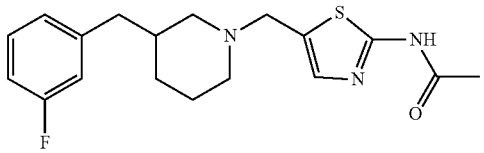

N-(5-((3-(3-fluorobenzyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 1-bromo-3-fluorobenzene, and N-(5-formylthiazol-2-yl)acetamide. LCMS (ESI): [M+H] 348. ¹HNMR: (400 MHz, Methanol-d4) δ 7.26-7.20 (m, 2H), 6.94 (d, J=7.6 Hz, 1H), 6.89-6.85 (m, 2H), 3.69-3.61 (m, 2H), 2.83-2.76 (m, 2H), 2.58-2.47 (m, 2H), 2.19 (s, 3H), 2.05-1.94 (m, 1H), 1.87-1.76 (m, 2H), 1.69-1.66 (m, 2H), 1.57-1.48 (m, 1H), 1.01-0.93 (m, 1H).

Example 1-6

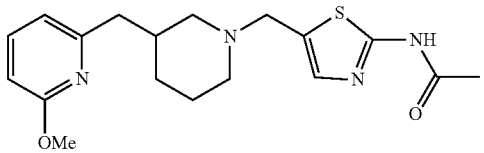 [SMILES: COc1cccc(CC2CCCN(Cc3cnc(NC(C)=O)s3)C2)c1]

N-(5-((3-((6-methoxypyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate and 2-chloro-6-methoxypyridine. LCMS (ESI): [M+H] 361. ¹HNMR: (400 MHz, CDCl₃) δ 12.41 (br s, 1H), 7.44-7.40 (m, 1H), 7.17 (s, 1H), 6.64 (d, J=7.2 Hz, 1H), 6.51 (d, J=8.0 Hz, 1H), 3.88 (s, 3H), 3.69-3.60 (m, 2H), 2.83-2.77 (m, 2H), 2.62-2.50 (m, 2H), 2.30 (s, 3H), 2.16-2.12 (m, 1H), 2.04-1.99 (m, 1H), 1.87-1.82 (m, 1H), 1.68-1.62 (m, 2H), 1.55-1.52 (m, 1H), 1.01-0.92 (m, 1H).

Example 1-7

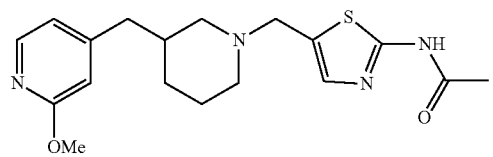 [SMILES: COc1cc(CC2CCCN(Cc3cnc(NC(C)=O)s3)C2)ccn1]

N-(5-((3-((2-methoxypyridin-4-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 4-bromo-2-methoxypyridine, and N-(5-formylthiazol-2-yl)acetamide. LCMS (ESI): [M+H] 361. ¹HNMR: (400 MHz, Methanol-d4) δ 7.95 (d, J=5.2 Hz, 1H), 7.19 (s, 1H), 6.77 (d, J=5.2 Hz, 1H), 6.59 (s, 1H), 3.86 (s, 3H), 3.67 (s, 2H), 2.82-2.74 (m, 2H), 2.51-2.49 (m, 2H), 2.19 (s, 3H), 2.07-2.00 (m, 1H), 1.93-1.84 (m, 1H), 1.82-1.77 (m, 1H), 1.69-1.67 (m, 2H), 1.59-1.55 (m, 1H), 1.03-0.96 (m, 1H).

Example 1-8

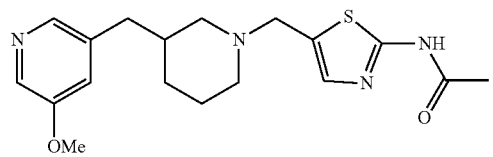 [SMILES: COc1cncc(CC2CCCN(Cc3cnc(NC(C)=O)s3)C2)c1]

N-(5-((3-((5-methoxypyridin-3-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 3-bromo-5-methoxypyridine, and N-(5-formylthiazol-2-yl)acetamide. LCMS (ESI): [M+H] 361. ¹HNMR: (400 MHz, CDCl₃) δ 11.18 (br s, 1H), 8.14 (d, J=2.4 Hz, 1H), 8.00 (s, 1H), 7.17 (s, 1H), 6.98 (s, 1H), 3.84 (s, 3H), 3.64-3.63 (m, 2H), 2.78-2.76 (m, 2H), 2.53-2.46 (m, 2H), 2.29 (s, 3H), 2.02-1.98 (m, 1H), 1.88-1.82 (m, 2H), 1.67-1.63 (m, 2H), 1.55-1.50 (m, 1H), 0.96-0.94 (m, 1H).

Example 1-9

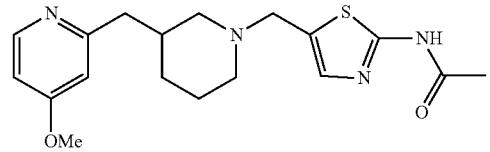 [SMILES: COc1ccnc(CC2CCCN(Cc3cnc(NC(C)=O)s3)C2)c1]

N-(5-((3-((4-methoxypyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl- 1,3,2-dioxaborolan-2-yl)methylene)piperidine-1-carboxylate, 2-bromo-5-methoxypyridine, and N-(5-formylthiazol-2-yl)acetamide. LCMS (ESI): [M+H] 361. ¹HNMR: (400 MHz, Methanol-d4) δ 8.21 (d, J=6.0 Hz, 1H), 7.21 (s, 1H), 6.81-6.78 (m, 2H), 3.85 (s, 3H), 3.71-3.67 (m, 2H), 2.86-2.77 (m, 2H), 2.63 (d, J=7.2 Hz, 2H), 2.20 (s, 3H), 2.08-2.02 (m, 2H), 1.89-1.82 (m, 1H), 1.75-1.61 (m, 2H), 1.58-1.52 (m, 1H), 1.06-1.03 (m, 1H).

Example 1-10

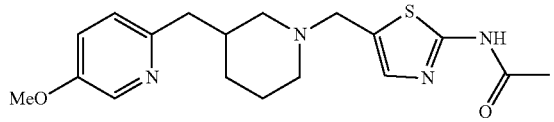 [SMILES: COc1ccc(CC2CCCN(Cc3cnc(NC(C)=O)s3)C2)nc1]

N-(5-((3-((5-methoxypyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-5-methoxypyridine, and N-(5-formylthiazol-2-yl)acetamide. LCMS (ESI): [M+H] 361. ¹HNMR: (400 MHz, CDCl₃) δ 12.31 (br s, 1H), 8.20 (d, J=2.8 Hz, 1H), 7.16 (s, 1H), 7.11-7.08 (m, 1H), 7.03-7.01 (m, 1H), 3.82 (s, 3H), 3.67-3.60 (m, 2H), 2.76 (d, J=10.2 Hz, 2H), 2.74-2.60 (m, 2H), 2.30 (s, 3H), 2.03-2.00 (m, 2H), 1.87-1.85 (m, 1H), 1.65 (d, J=9.6 Hz, 2H), 1.62-1.02 (m, 1H), 0.99-0.97 (m, 1H).

Example 1-11

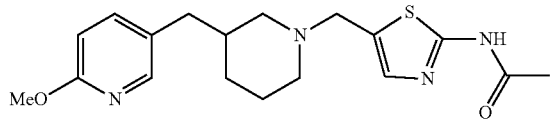 [SMILES: COc1ccc(CC2CCCN(Cc3cnc(NC(C)=O)s3)C2)cn1]

N-(5-((3-((6-methoxypyridin-3-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 3-bromo-5-methoxypyridine, and N-(5-formylthiazol-2-yl)acetamide. LCMS (ESI): [M+H] 360. ¹HNMR: (400 MHz, Methanol-d4) δ 7.87 (d, J=2.0 Hz, 1H), 7.49 (dd, J=8.8, 2.0 Hz, 1H), 7.20 (s, 1H), 6.71 (d, J=8.4 Hz, 1H), 3.86 (s, 3H), 3.69-3.62 (m, 2H), 2.88-2.71 (m, 2H), 2.46-2.44 (m, 2H), 2.20 (s, 3H), 2.07-1.97 (m, 1H), 1.86-1.73 (m, 2H), 1.72-1.62 (m, 2H), 1.60-1.44 (m, 1H), 1.05-0.88 (m, 1H).

Example 1-12

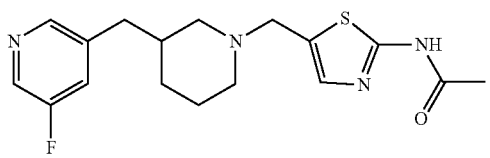 [SMILES: CC(=O)Nc1ncc(CN2CCCC(Cc3cncc(F)c3)C2)s1]

N-(5-((3-((5-fluoropyridin-3-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 3-bromo-5-methoxypyridine, and N-(5-formylthiazol-2-yl)acetamide. LCMS (ESI): [M+H] 349. ¹HNMR: (400 MHz, CDCl₃) δ 11.88 (br s, 1H), 8.30 (s, 1H), 8.22 (s, 1H), 7.21-7.17 (m, 2H), 3.68-3.59 (m, 2H), 2.77-2.74 (m, 2H), 2.63-2.47 (m, 2H), 2.31 (s, 3H), 2.08-2.03 (m, 1H), 1.93-1.83 (m, 2H), 1.73-1.68 (m, 2H), 1.56-1.50 (m, 1H), 1.03-0.93 (m, 1H).

Example 1-13

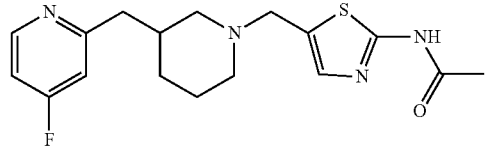 [SMILES: CC(=O)Nc1ncc(CN2CCCC(Cc3cc(F)ccn3)C2)s1]

N-(5-((3-((4-fluoropyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-4-fluoropyridine, and N-(5-formylthiazol-2-yl)acetamide. LCMS (ESI): [M+H] 349. ¹HNMR: (400 MHz, Methanol-d4) δ 8.46 (dd, J=8.8, 5.6 Hz, 1H), 7.23 (s, 1H), 7.14-7.11 (m, 1H), 7.09-7.06 (m, 1H), 3.71 (s, 2H), 2.88-2.81 (m, 2H), 2.75-2.72 (m, 1H), 2.22 (s, 3H), 2.12-2.09 (m, 2H), 1.93-1.90 (m, 1H), 1.71-1.54 (m, 3H), 1.12-1.07 (m, 1H).

Example 1-14

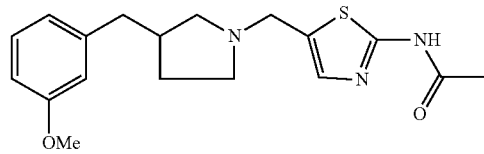 [SMILES: COc1cccc(CC2CCN(Cc3cnc(NC(C)=O)s3)C2)c1]

N-(5-((3-(3-methoxybenzyl)pyrrolidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 1-bromo-3-methoxybenzene, and N-(5-formylthiazol-2-yl)acetamide. LCMS (ESI): [M+H] 346. ¹HNMR: (400 MHz, Methanol-d4) δ 7.23 (s, 1H), 7.15-7.11 (m, 1H), 6.77-6.66 (m, 3H), 3.83-3.66 (m, 5H), 2.73-2.55 (m, 5H), 2.52-2.40 (m, 1H), 2.29-2.23 (m, 1H), 2.19 (s, 3H), 1.99-1.87 (m, 1H), 1.56-1.46 (m, 1H).

Example 1-15

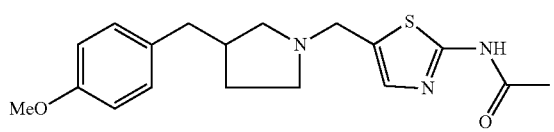 [SMILES: COc1ccc(CC2CCN(Cc3cnc(NC(C)=O)s3)C2)cc1]

N-(5-((3-(4-methoxybenzyl)pyrrolidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 1-chloro-4-methoxybenzene, and N-(5-formylthiazol-2-yl)acetamide. LCMS (ESI): [M+H] 346. $^1$HNMR: (400 MHz, Methanol-d4) δ 7.24 (s, 1H), 7.07 (dd, J=6.4, 2.0 Hz, 2H), 6.81 (t, J=2.8 Hz, 1H), 6.79 (d, J=2.0 Hz, 1H), 3.79-3.73 (m, 5H), 2.74-2.69 (m, 2H), 2.65-2.58 (m, 3H), 2.50-2.42 (m, 1H), 2.29-2.24 (m, 1H), 2.19 (s, 3H), 1.96-1.89 (m, 1H), 1.55-1.51 (m, 1H).

Example 1-16

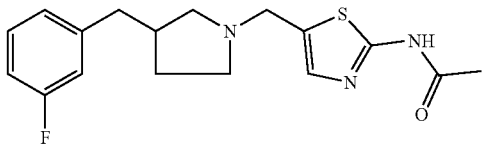 [SMILES: CC(=O)Nc1ncc(CN2CCC(Cc3cccc(F)c3)C2)s1]

N-(5-((3-(3-fluorobenzyl)pyrrolidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 1-bromo-3-fluorobenzene, and N-(5-formylthiazol-2-yl)acetamide. LCMS (ESI): [M+H] 334. $^1$HNMR: (400 MHz, DMSO-d6) δ 11.50 (br s, 1H), 7.32-7.26 (m, 1H), 7.22 (s, 1H), 7.04-6.97 (m, 3H), 3.72-3.63 (m, 2H), 3.32 (s, 2H), 2.69-2.58 (m, 2H), 2.58-2.52 (m, 3H), 2.45-2.35 (m, 1H), 2.17-2.14 (m, 1H), 2.10 (s, 3H), 1.88-1.79 (m, 1H), 1.45-1.37 (m, 1H).

Example 1-17

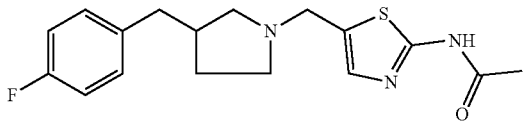 [SMILES: CC(=O)Nc1ncc(CN2CCC(Cc3ccc(F)cc3)C2)s1]

N-(5-((3-(4-fluorobenzyl)pyrrolidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 1-bromo-4-fluorobenzene, and N-(5-formylthiazol-2-yl)acetamide. LCMS (ESI): [M+H] 334. $^1$HNMR: (400 MHz, Methanol-d4) δ 7.23 (s, 1H), 7.18-7.15 (m, 2H), 6.97-6.93 (m, 2H), 3.82-3.72 (m, 2H), 2.71-2.67 (m, 5H), 2.67-2.64 (m, 1H), 2.28-2.26 (m, 1H), 2.19 (s, 3H), 1.98-1.94 (m, 1H), 1.54-1.50 (m, 1H).

Example 1-18

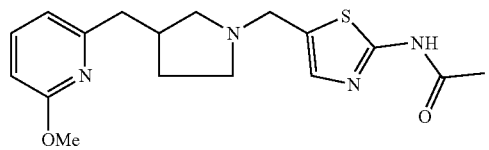 [SMILES: COc1cccc(CC2CCN(Cc3cnc(NC(C)=O)s3)C2)n1]

N-(5-((3-((6-methoxypyridin-2-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 2-chloro-6-methoxypyridine, and N-(5-formylthiazol-2-yl)acetamide. LCMS (ESI): [M+H] 347. $^1$HNMR: (400 MHz, Methanol-d4) δ 7.55-7.50 (m, 1H), 7.25 (s, 1H), 6.76 (d, J=6.8 Hz, 1H), 6.57 (d, J=8.4 Hz, 1H), 3.85 (s, 3H), 3.84-3.74 (m, 2H), 2.80-2.68 (m, 6H), 2.36-2.37 (m, 1H), 2.19 (s, 3H), 2.03-1.96 (m, 1H), 1.62-1.54 (m, 1H).

Example 1-19

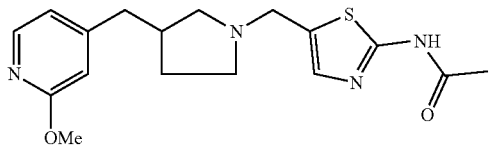 [SMILES: COc1cc(CC2CCN(Cc3cnc(NC(C)=O)s3)C2)ccn1]

N-(5-((3-((2-methoxypyridin-4-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 4-bromo-2-methoxypyridine, and N-(5-formylthiazol-2-yl)acetamide. LCMS (ESI): [M+H] 347. $^1$HNMR: (400 MHz, Methanol-d4) δ 7.97 (d, J=5.6 Hz, 1H), 7.23 (s, 1H), 6.81 (d, J=5.6 Hz, 1H), 6.63 (s, 1H), 3.86 (s, 3H), 3.83-3.73 (m, 2H), 2.73-2.69 (m, 5H), 2.67-2.64 (m, 1H), 2.29-2.27 (m, 1H), 2.17 (s, 3H), 2.19-2.00 (m, 1H), 1.52-1.50 (m, 1H).

Example 1-20

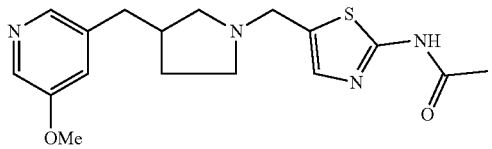 [SMILES: COc1cncc(CC2CCN(Cc3cnc(NC(C)=O)s3)C2)c1]

N-(5-((3-((5-methoxypyridin-3-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 3-bromo-5-methoxypyridine, and N-(5-formylthiazol-2-yl)acetamide. LCMS (ESI): [M+H] 347. ¹HNMR: (400 MHz, CDCl₃) δ 12.36 (s, 1H), 8.13 (d, J=2.4 Hz, 1H), 8.04 (d, J=1.6 Hz, 1H), 7.18 (s, 1H), 6.99-6.98 (m, 1H), 3.82 (s, 3H), 3.80-3.71 (m, 2H), 2.70-2.62 (m, 5H), 2.53-2.44 (m, 1H), 2.30 (s, 3H), 2.29-2.25 (m, 1H), 2.02-1.93 (m, 1H), 1.54-1.46 (m, 1H).

Example 1-21

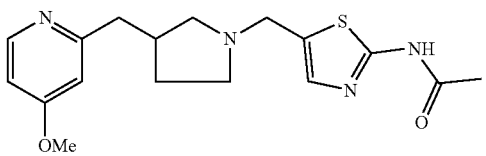 [SMILES: COc1ccnc(CC2CCN(Cc3cnc(NC(C)=O)s3)C2)c1]

N-(5-((3-((4-methoxypyridin-2-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 2-bromo-4-methoxypyridine, and N-(5-formylthiazol-2-yl)acetamide. LCMS (ESI): [M+H] 347. ¹HNMR: (400 MHz, Methanol-d4) δ 8.22 (d, J=6.0 Hz, 1H), 7.24 (s, 1H), 6.84 (d, J=2.4 Hz, 1H), 6.82-6.80 (m, 1H), 3.86 (s, 3H), 3.84-3.75 (m, 2H), 2.79 (d, J=7.6 Hz, 2H), 2.74-2.59 (m, 4H), 2.34-2.29 (m, 1H), 2.19 (s, 3H), 2.03-1.92 (m, 1H), 1.62-1.53 (m, 1H).

Example 1-22

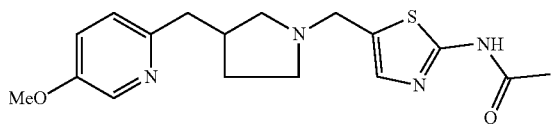 [SMILES: COc1ccc(CC2CCN(Cc3cnc(NC(C)=O)s3)C2)nc1]

N-(5-((3-((5-methoxypyridin-2-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 2-bromo-5-methoxypyridine, and N-(5-formylthiazol-2-yl)acetamide. LCMS (ESI): [M+H] 347. ¹HNMR: (400 MHz, CDCl₃) δ 11.55 (br s, 1H), 8.21 (d, J=2.8 Hz, 1H), 7.19 (s, 1H), 7.12-7.09 (m, 1H), 7.05-7.03 (m, 1H), 3.83 (s, 3H), 3.80-3.71 (m, 2H), 2.79 (d, J=7.2 Hz, 2H), 2.78-2.60 (m, 4H), 2.31-2.29 (m, 4H), 1.97-1.55 (m, 1H), 1.54-1.52 (m, 1H).

Example 1-23

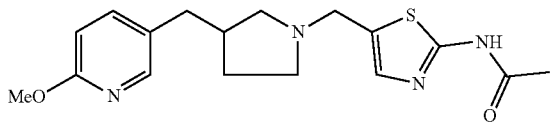 [SMILES: COc1ccc(CC2CCN(Cc3cnc(NC(C)=O)s3)C2)cn1]

N-(5-((3-((6-methoxypyridin-3-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 5-bromo-2-methoxypyridine, and N-(5-formylthiazol-2-yl)acetamide. LCMS (ESI): [M+H] 347. ¹HNMR: (400 MHz, Methanol-d4) δ 7.92 (d, J=1.6 Hz, 1H), 7.53 (dd, J=8.8, 2.4 Hz, 1H), 7.24 (s, 1H), 6.72 (d, J=8.8 Hz, 1H), 3.86 (s, 3H), 3.83-3.74 (m, 2H), 2.75-2.66 (m, 2H), 2.66-2.57 (m, 3H), 2.51-2.39 (m, 1H), 2.30-2.25 (m, 1H), 2.19 (s, 3H), 2.00-1.91 (m, 1H), 1.57-1.48 (m, 1H).

Example 1-24

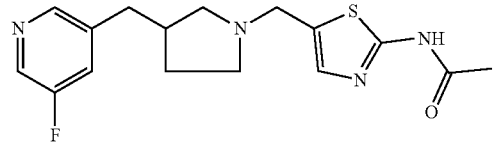 [SMILES: CC(=O)Nc1ncc(CN2CCC(Cc3cncc(F)c3)C2)s1]

N-(5-((3-((5-fluoropyridin-3-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 3-bromo-5-fluoropyridine, and N-(5-formylthiazol-2-yl)acetamide. LCMS (ESI): [M+H] 335. ¹HNMR: (400 MHz, CDCl₃) δ 12.44 (br s, 1H), 8.29 (d, J=2.8 Hz, 1H), 8.25 (s, 1H), 7.22-7.18 (m, 2H), 3.80-3.71 (m, 2H), 2.72-2.62 (m, 5H), 2.52-2.43 (m, 1H), 2.30 (s, 3H), 2.28-2.26 (m, 1H), 2.02-1.94 (m, 1H), 1.54-1.45 (m, 1H).

Example 1-25

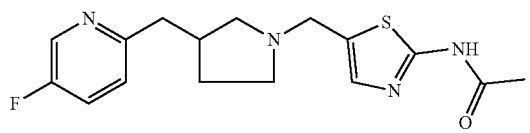

N-(5-((3-((5-fluoropyridin-2-yl)methyl)pyrrolidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)pyrrolidine-1-carboxylate, 2-bromo-5-fluoropyridine, and N-(5-formylthiazol-2-yl)acetamide. LCMS (ESI): [M+H] 335. ¹HNMR: (400 MHz, CDCl₃) δ 11.55 (s, 1H), 8.36 (d, J=3.2 Hz, 1H), 7.32-7.27 (m, 1H), 7.19 (s, 1H), 7.13-7.10 (m, 1H), 3.80-3.72 (m, 2H), 2.85-2.82 (m, 2H), 2.74-2.61 (m, 4H), 2.32-2.30 (m, 1H), 2.29 (s, 3H), 2.00-1.95 (m, 1H), 1.57-1.51 (m, 1H).

Example 1-26

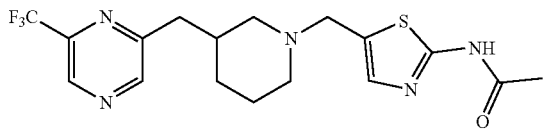 [SMILES: CC(=O)Nc1ncc(CN2CCCC(Cc3cncc(C(F)(F)F)n3)C2)s1]

N-(5-((3-((6-(trifluoromethyl)pyrazin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-chloro-6-(trifluoromethyl)pyrazine, and N-[5-(chloromethyl)thiazol-2-yl]acetamide. LCMS (ESI): [M+H] 400. ¹HNMR: (500 MHz, CDCl₃) δ 11.56 (br s, 1H), 8.78 (s, 1H), 8.64 (s, 1H), 7.18 (s, 1H), 3.75-3.58 (m, 2H), 2.95-2.68 (m, 3H), 2.31 (s, 3H), 2.23-2.09 (m, 2H), 2.04-1.91 (m, 1H), 1.74-1.52 (m, 4H), 1.09 (m, 1H).

Example 1-27

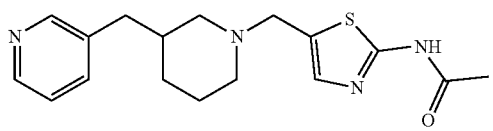 [SMILES: CC(=O)Nc1ncc(CN2CCCC(Cc3cccnc3)C2)s1]

N-(5-((3-(pyridin-3-ylmethyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate 3-bromopyridine, and N-[5-(chloromethyl)thiazol-2-yl]acetamide. LCMS (ESI): [M+H] 331. ¹HNMR: (500 MHz, CDCl₃) δ 11.79 (br s, 1H), 8.54 (dd, J=1.8, 4.9 Hz, 1H), 7.59 (dt, J=1.8, 7.6 Hz, 1H), 7.19 (s, 1H), 7.14 (d, J=7.9 Hz, 1H), 7.13-7.09 (m, 1H), 3.75-3.56 (m, 2H), 2.89-2.76 (m, 2H), 2.76-2.63 (m, 2H), 2.32 (s, 3H), 2.12 (m, 1H), 2.08-2.01 (m, 1H), 1.90 (br t, J=10.4 Hz, 1H), 1.78-1.62 (m, 2H), 1.60-1.47 (m, 1H), 1.12-0.96 (m, 1H).

Example 1-28

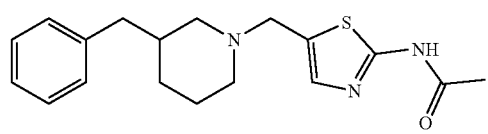 [SMILES: CC(=O)Nc1ncc(CN2CCCC(Cc3ccccc3)C2)s1]

N-(5-((3-benzylpiperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, bromobenzene, and N-[5-(chloromethyl)thiazol-2-yl]acetamide. LCMS (ESI): [M+H] 330. ¹HNMR: (500 MHz, CDCl₃) δ 11.61 (br s, 1H), 7.32-7.24 (m, 2H), 7.22-7.08 (m, 4H), 3.73-3.58 (m, 2H), 2.80 (br d, J=7.9 Hz, 2H), 2.60-2.51 (m, 1H), 2.50-2.42 (m, 1H), 2.31 (s, 3H), 1.99 (br t, J=10.4 Hz, 1H), 1.93-1.86 (m, 1H), 1.85-1.79 (m, 1H), 1.71-1.62 (m, 2H), 1.56-1.45 (m, 1H), 1.00-0.87 (m, 1H).

Example 1-29

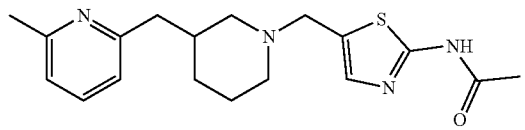 [SMILES: CC(=O)Nc1ncc(CN2CCCC(Cc3cccc(C)n3)C2)s1]

N-(5-((3-((6-methylpyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-6-methylpyridine, and N-[5-(chloromethyl)thiazol-2-yl]acetamide. LCMS (ESI): [M+H] 345. ¹HNMR: (500 MHz, CDCl₃) δ 12.11 (br s, 1H), 7.46 (t, J=7.6 Hz, 1H), 7.17 (s, 1H), 6.95 (d, J=7.3 Hz, 1H), 6.91 (d, J=7.3 Hz, 1H), 3.64 (q, J=14.0 Hz, 2H), 2.79 (br d, J=8.5 Hz, 2H), 2.71-2.61 (m, 2H), 2.52 (s, 3H), 2.31 (s, 3H), 2.16-2.06 (m, 1H), 2.02 (br t, J=10.1 Hz, 1H), 1.86 (br t, J=10.4 Hz, 1H), 1.71-1.62 (m, 2H), 1.59-1.46 (m, 1H), 1.07-0.95 (m, 1H).

Example 1-30

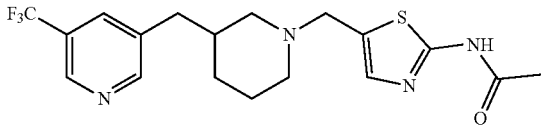 [SMILES: CC(=O)Nc1ncc(CN2CCCC(Cc3cncc(C(F)(F)F)c3)C2)s1]

N-(5-((3-((5-(trifluoromethyl)pyridin-3-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 3-bromo-5-(trifluoromethyl)pyridine, and N-[5-(chloromethyl)thiazol-2-yl]acetamide. LCMS (ESI): [M+H] 399. ¹HNMR: (500 MHz, CDCl₃) δ 11.74 (br s, 1H), 8.73 (s, 1H), 8.60 (s, 1H), 7.70 (s, 1H), 7.18 (s, 1H), 3.74-3.58 (m, 2H), 2.76 (m, 2H), 2.71-2.63 (m, 1H), 2.56 (m, 1H), 2.31 (s, 3H), 2.08 (m, 1H), 1.90 (m, 2H), 1.75-1.60 (m, 2H), 1.59-1.48 (m, 1H), 1.06-0.95 (m, 1H).

Example 1-31

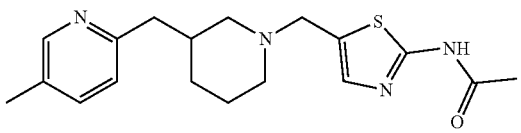 [SMILES: CC(=O)Nc1ncc(CN2CCCC(Cc3ccc(C)cn3)C2)s1]

N-(5-((3-((5-methylpyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-chloro-5-methylpyridine, and N-[5-(chloromethyl)thiazol-2-yl]acetamide. LCMS (ESI): [M+H] 345. $^1$HNMR: (500 MHz, CDCl$_3$) δ 11.94 (br s, 1H), 8.35 (s, 1H), 7.38 (dd, J=1.8, 7.9 Hz, 1H), 7.17 (s, 1H), 7.02 (d, J=7.9 Hz, 1H), 3.72-3.56 (m, 2H), 2.84-2.73 (m, 2H), 2.65 (dq, J=7.3, 13.6 Hz, 2H), 2.31 (s, 3H), 2.29 (s, 3H), 2.14-1.97 (m, 2H), 1.87 (br t, J=10.4 Hz, 1H), 1.70-1.61 (m, 2H), 1.58-1.46 (m, 1H), 1.06-0.95 (m, 1H).

Example 1-3

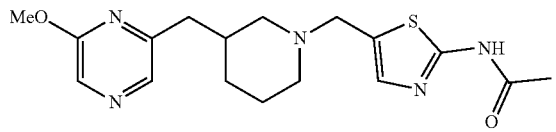 [SMILES: COc1cncc(CC2CCCN(Cc3cnc(NC(C)=O)s3)C2)n1]

N-(5-((3-((6-methoxypyrazin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-6-methoxypyrazine, and N-[5-(chloromethyl)thiazol-2-yl]acetamide. LCMS (ESI): [M+H] 361.

Example 1-33

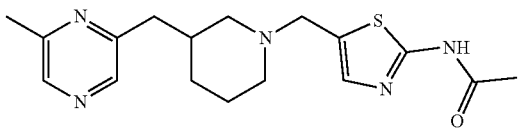

N-(5-((3-((6-methylpyrazin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-6-methylpyrazine, and N-[5-(chloromethyl)thiazol-2-yl]acetamide. LCMS (ESI): [M+H] 346. $^1$HNMR: (500 MHz, CDCl$_3$) δ 11.80 (br s, 1H), 8.27 (s, 1H), 8.21 (s, 1H), 7.18 (s, 1H), 3.70-3.59 (m, 2H), 2.78 (br s, 2H), 2.67 (m, 2H), 2.54 (s, 3H), 2.31 (s, 3H), 2.18-2.00 (m, 2H), 1.94-1.85 (m, 1H), 1.65 (m, 2H), 1.54 (m, 1H), 1.13-0.96 (m, 1H).

Example 1-34

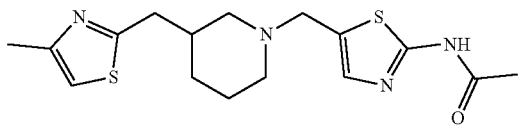 [SMILES: CC(=O)Nc1ncc(CN2CCCC(Cc3nc(C)cs3)C2)s1]

N-(5-((3-((4-methylthiazol-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-4-methylthiazole, and N-[5-(chloromethyl)thiazol-2-yl]acetamide. LCMS (ESI): [M+H] 351. $^1$HNMR: (500 MHz, Methanol-d4) δ 7.54 (s, 1H), 7.04 (s, 1H), 4.88-4.99 (m, 1H), 4.46-4.56 (m, 2H), 4.41 (s, 1H), 3.51 (br d, J=11.0 Hz, 2H), 2.84-3.05 (m, 3H), 2.74 (br t, J=12.2 Hz, 1H), 2.30-2.42 (m, 3H), 2.18-2.25 (m, 4H), 1.92-2.06 (m, 1H), 1.87 (br d, J=14.0 Hz, 1H), 1.73 (br d, J=13.4 Hz, 1H), 1.22-1.39 (m, 1H).

Example 1-35

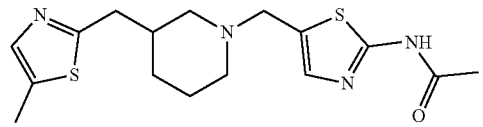 [SMILES: CC(=O)Nc1ncc(CN2CCCC(Cc3ncc(C)s3)C2)s1]

N-(5-((3-((5-methylthiazol-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-5-methylthiazole, and N-[5-(chloromethyl)thiazol-2-yl]acetamide. LCMS (ESI): [M+H] 351. $^1$HNMR: (500 MHz, Methanol-d4) δ 7.57 (s, 1H), 7.40-7.46 (m, 1H), 4.94-5.04 (m, 1H), 4.53 (s, 2H), 3.53 (br d, J=10.4 Hz, 2H), 2.95-3.06 (m, 2H), 2.90 (br s, 1H), 2.77 (br t, J=11.9 Hz, 1H), 2.45 (d, J=1.2 Hz, 3H), 2.18-2.29 (m, 4H), 1.95-2.10 (m, 1H), 1.83-1.94 (m, 1H), 1.75 (br d, J=13.4 Hz, 1H), 1.42 (s, 1H), 1.21-1.37 (m, 1H).

Example 1-36

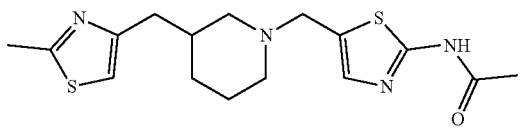 [SMILES: CC(=O)Nc1ncc(CN2CCCC(Cc3csc(C)n3)C2)s1]

N-(5-((3-((2-methylthiazol-4-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 4-bromo-2-methylthiazole, and N-[5-(chloromethyl)thiazol-2-yl]acetamide. LCMS (ESI): [M+H] 351. ¹HNMR: (500 MHz, Methanol-d4) δ 7.57 (s, 1H), 7.30 (s, 1H), 4.52 (br s, 2H), 3.44-3.56 (m, 2H), 2.86-2.93 (m, 1H), 2.70-2.82 (m, 6H), 2.18-2.23 (m, 4H), 1.94-2.03 (m, 1H), 1.86 (br d, J=13.4 Hz, 1H), 1.76 (br d, J=12.8 Hz, 1H), 1.20-1.32 (m, 1H).

Example 1-37

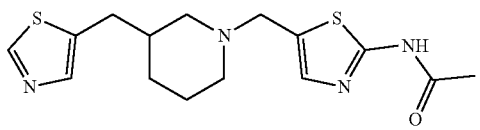 [SMILES: CC(=O)Nc1ncc(CN2CCCC(Cc3cncs3)C2)s1]

N-(5-((3-(thiazol-5-ylmethyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 5-bromothiazole, and N-[5-(chloromethyl)thiazol-2-yl]acetamide. LCMS (ESI): [M+H] 337. ¹HNMR: (500 MHz, DMSO-d6) δ 11.93 (s, 1H), 8.91 (s, 1H), 7.61 (s, 1H), 7.22 (s, 1H), 4.04 (s, 6H), 3.50-3.64 (m, 3H), 2.64-2.82 (m, 5H), 2.52-2.56 (m, 1H), 2.11 (s, 4H), 1.91-2.00 (m, 1H), 1.69-1.80 (m, 2H), 1.57-1.65 (m, 2H), 1.36-1.44 (m, 1H), 0.94 (br d, J=9.8 Hz, 1H).

Example 1-38

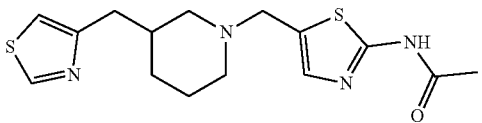 [SMILES: CC(=O)Nc1ncc(CN2CCCC(Cc3cscn3)C2)s1]

N-(5-((3-(thiazol-4-ylmethyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 4-bromothiazole, and N-[5-(chloromethyl)thiazol-2-yl]acetamide. LCMS (ESI): [M+H] 337. ¹HNMR: (500 MHz, DMSO-d6) δ 11.92 (s, 1H), 8.99 (d, J=1.8 Hz, 1H), 7.30 (d, J=1.8 Hz, 1H), 7.21 (s, 1H), 4.04 (s, 5H), 3.49-3.63 (m, 5H), 2.59-2.74 (m, 5H), 2.11 (s, 4H), 1.87-1.99 (m, 2H), 1.75 (br t, J=10.4 Hz, 1H), 1.58 (br d, J=10.4 Hz, 2H), 1.34-1.44 (m, 1H), 0.92 (br d, J=9.8 Hz, 1H).

Example 1-39

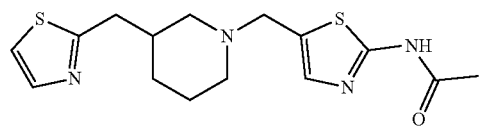 [SMILES: CC(=O)Nc1ncc(CN2CCCC(Cc3nccs3)C2)s1]

N-(5-((3-(thiazol-2-ylmethyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromothiazole, and N-[5-(chloromethyl)thiazol-2-yl]acetamide. LCMS (ESI): [M+H] 337. ¹HNMR: (500 MHz, Methanol-d4) δ 7.66 (d, J=3.7 Hz, 1H), 7.44 (d, J=3.7 Hz, 1H), 7.21 (s, 1H), 3.67 (s, 2H), 2.96 (d, J=7.3 Hz, 2H), 2.83 (br t, J=11.6 Hz, 2H), 2.15-2.24 (m, 4H), 2.01-2.12 (m, 2H), 1.88 (br t, J=10.4 Hz, 1H), 1.68-1.81 (m, 2H), 1.52-1.63 (m, 1H), 1.07 (br dd, J=11.6, 2.4 Hz, 1H).

Example 1-40

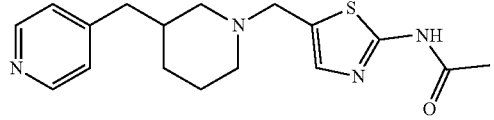 [SMILES: CC(=O)Nc1ncc(CN2CCCC(Cc3ccncc3)C2)s1]

N-(5-((3-(pyridin-4-ylmethyl)piperidin-1-yl)methyl)thiazol-2-yl)acetamide

The title compound was prepared in an analogous manner of that in scheme 1 from tert-butyl 3-((4,4,5,5-tetramethyl-1,3,2-dioxaborolan-2-yl)methylene)piperidine-1-carboxylate, 4-bromopyridine, and N-[5-(chloromethyl)thiazol-2-yl]acetamide. LCMS (ESI): [M+H] 331. ¹HNMR: (500 MHz, Methanol-d4) δ 8.38 (br d, J=5.5 Hz, 2H), 7.23-7.29 (m, 2H), 7.20 (s, 1H), 3.66 (s, 2H), 2.69-2.87 (m, 2H), 2.49-2.68 (m, 2H), 2.21 (s, 3H), 2.00-2.12 (m, 2H), 1.93 (td, J=7.0, 3.1 Hz, 1H), 1.76-1.87 (m, 1H), 1.64-1.76 (m, 2H), 1.46-1.62 (m, 1H), 1.03 (br d, J=9.8 Hz, 1H).

Example 1-41

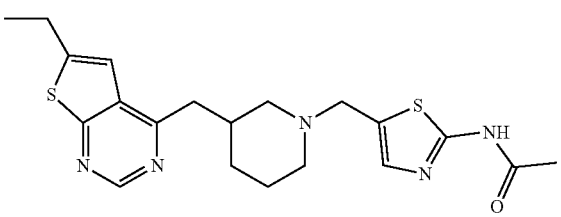

N-(5-((3-((6-ethylthieno[2,3-d]pyrimidin-4-yl)methyl)piperidin-1-yl)methyl)thiazol-2-yl)acetamide The title compound was prepared in an analogous manner of that in scheme 1 from tert-butyl 3-((4,4,5,5-tetramethyl- 1,3,2-dioxaborolan-2-yl)methylene)piperidine-1-carboxylate, 4-chloro-6-ethylthieno[2,3-d]pyrimidine, and N-[5-(chloromethyl)thiazol-2-yl]acetamide. LCMS (ESI): [M+H] 416. ¹HNMR: (500 MHz, Methanol-d4) δ 8.81-8.90 (m, 1H), 7.55 (s, 1H), 7.32 (dd, J=2.4, 1.2 Hz, 1H), 4.51 (br d, J=6.1 Hz, 2H), 3.53 (br d, J=11.6 Hz, 2H), 3.02-3.20 (m, 4H), 2.92 (br s, 1H), 2.79-2.88 (m, 1H), 2.45 (br s, 1H), 2.23 (s, 3H), 1.96-2.10 (m, 1H), 1.71-1.94 (m, 2H), 1.34-1.44 (m, 5H), 1.20-1.33 (m, 1H).

Example 1-42

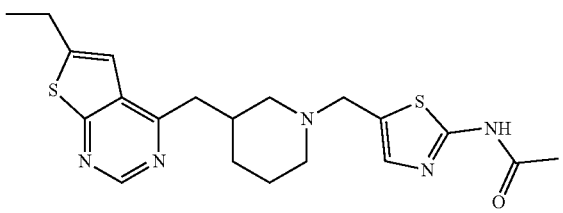 [SMILES: CCc1cc2c(CC3CCCN(Cc4cnc(NC(C)=O)s4)C3)ncnc2s1]

N-(5-((3-((6-ethylthieno[3,2-d]pyrimidin-4-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 4-chloro-6-ethylthieno[3,2-d]pyrimidine, and N-[5-(chloromethyl)thiazol-2-yl]acetamide. LCMS (ESI): [M+H] 416. ¹HNMR: (500 MHz, Methanol-d4) δ 8.96-9.00 (m, 1H), 7.51-7.61 (m, 1H), 7.31-7.36 (m, 1H), 4.90-4.94 (m, 2H), 4.48-4.55 (m, 2H), 3.01-3.18 (m, 4H), 2.83-2.97 (m, 2H), 2.75-2.83 (m, 1H), 2.21-2.24 (m, 4H), 1.95-2.07 (m, 1H), 1.90 (br d, J=13.4 Hz, 1H), 1.68-1.84 (m, 2H), 1.35-1.50 (m, 5H), 0.96 (t, J=7.3 Hz, 1H).

Example 1-43

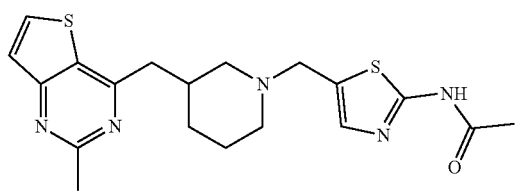 [SMILES: CC(=O)Nc1ncc(CN2CCCC(Cc3nc(C)nc4ccsc34)C2)s1]

N-(5-((3-((2-methylthieno[3,2-d]pyrimidin-4-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 4-chloro-2-methylthieno[3,2-d]pyrimidine, and N-[5-(chloromethyl)thiazol-2-yl]acetamide. LCMS (ESI): [M+H] 402. ¹HNMR: (500 MHz, Methanol-d4) δ 8.33 (d, J=5.5 Hz, 1H), 7.56 (s, 1H), 7.51 (d, J=5.5 Hz, 1H), 4.56 (br d, J=14.0 Hz, 1H), 4.49 (d, J=14.0 Hz, 1H), 3.60-3.74 (m, 1H), 3.52-3.59 (m, 1H), 3.11-3.18 (m, 1H), 3.03-3.11 (m, 1H), 2.91-3.01 (m, 1H), 2.79-2.90 (m, 2H), 2.74 (s, 3H), 2.66 (s, 3H), 2.52-2.62 (m, 1H), 2.23 (s, 4H).

Example 1-44

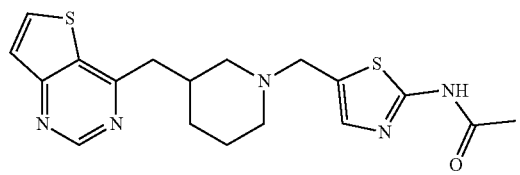 [SMILES: CC(=O)Nc1ncc(CN2CCCC(Cc3ncnc4ccsc34)C2)s1]

N-(5-((3-(thieno[3,2-d]pyrimidin-4-ylmethyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 4-chlorothieno[3,2-d]pyrimidine, and N-[5-(chloromethyl)thiazol-2-yl]acetamide. LCMS (ESI): [M+H] 388. ¹HNMR: (500 MHz, Methanol-d4) δ 9.06 (s, 1H), 8.35 (d, J=5.5 Hz, 1H), 7.51-7.63 (m, 3H), 2.63-2.67 (m, 2H), 2.53 (s, 1H), 2.23-2.24 (m, 3H), 1.97-2.11 (m, 2H), 1.91 (br d, J=14.0 Hz, 2H), 1.78 (br d, J=14.0 Hz, 1H), 1.38-1.45 (m, 5H).

Example 1-45

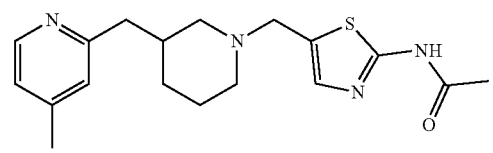 [SMILES: CC(=O)Nc1ncc(CN2CCCC(Cc3cc(C)ccn3)C2)s1]

N-(5-((3-((4-methylpyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 2-bromo-4-methylpyridine, and N-[5-(chloromethyl)thiazol-2-yl]acetamide. LCMS (ESI): [M+H] 345. ¹HNMR: (500 MHz, Methanol-d4) δ 8.60 (d, J=6.1 Hz, 1H), 7.77-7.83 (m, 2H), 7.59 (s, 1H), 3.42-3.59 (m, 2H), 2.90-3.09 (m, 4H), 2.83-2.88 (m, 1H), 2.66 (d, J=1.8 Hz, 4H), 2.20-2.25 (m, 3H), 2.00 (br d, J=12.8 Hz, 1H), 1.81 (s, 1H), 1.79 (br s, 1H), 1.24-1.44 (m, 1H).

Example 1-46

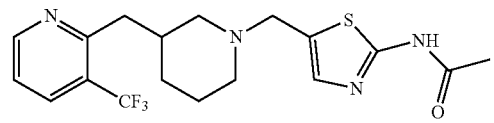 [SMILES: CC(=O)Nc1ncc(CN2CCCC(Cc3ncccc3C(F)(F)F)C2)s1]

N-(5-((3-((3-(trifluoromethyl)pyridin-2-yl)methyl)piperidin-1-yl)methyl)thiazol-2-yl)acetamide The title compound was prepared in an analogous manner of that in scheme 1 from tert-butyl 3-((4,4,5,5-tetramethyl- 1,3,2-dioxaborolan-2-yl)methylene)piperidine-1-carboxylate, 2-bromo-3-(trifluoromethyl)pyridine, and N-[5-(chloromethyl)thiazol-2-yl]acetamide. LCMS (ESI): [M+H] 399. ¹HNMR: (500 MHz, Methanol-d4) δ 8.74 (br dd, J=7.9, 4.9 Hz, 1H), 8.11 (t, J=6.4 Hz, 1H), 7.40-7.51 (m, 2H), 3.48-3.61 (m, 3H), 2.79-3.05 (m, 6H), 2.18-2.28 (m, 2H), 1.94-2.10 (m, 1H), 1.87 (s, 1H), 1.84 (br s, 1H), 1.72-1.82 (m, 1H), 1.28-1.43 (m, 1H).

Example 1-47

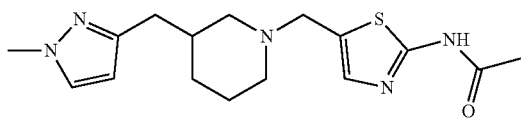 [SMILES: CC(=O)Nc1ncc(CN2CCCC(Cc3ccn(C)n3)C2)s1]

N-(5-((3-((1-methyl-1H-pyrazol-3-yl)methyl)piperidin-1-yl)methyl)thiazol-2-yl)acetamide The title compound was prepared in an analogous manner of that in scheme 1 from tert-butyl 3-((4,4,5,5-tetramethyl-1,3,2-dioxaborolan-2-yl)methylene)piperidine-1-carboxylate, 3-bromo-1-methyl-1H-pyrazole, and N-[5-(chloromethyl)thiazol-2-yl]acetamide. LCMS (ESI): [M+H] 334. ¹HNMR: (500 MHz, Methanol-d4) δ 7.42 (d, J=1.8 Hz, 1H), 7.22 (s, 1H), 6.04 (d, J=1.8 Hz, 1H), 3.80 (s, 3H), 3.67 (s, 2H), 2.86 (br d, J=7.9 Hz, 2H), 2.43-2.53 (m, 2H), 2.18-2.22 (m, 3H), 1.97-2.07 (m, 1H), 1.82-1.92 (m, 1H), 1.66-1.79 (m, 3H), 1.51-1.60 (m, 1H), 0.97 (br dd, J=11.9, 3.4 Hz, 1H).

Scheme 2

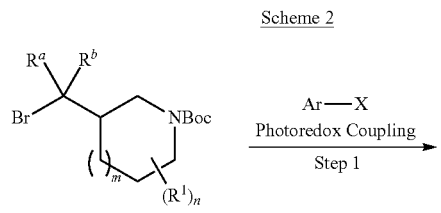

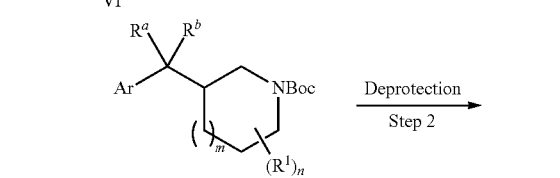

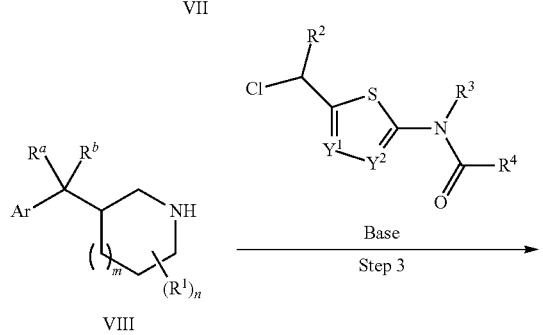

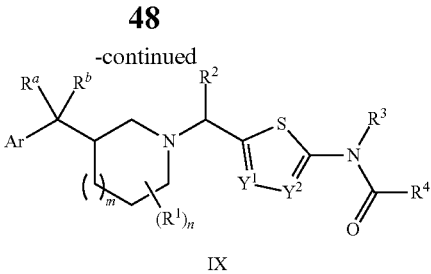

IX

Intermediate 5

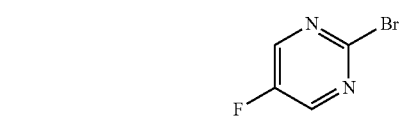

tert-butyl 3-((5-fluoropyrimidin-2-yl)methyl)pyrrolidine-1-carboxylate

A solution of NiCl₂(glyme) (0.084 g, 0.384 mmol), 4-tert-butyl-2-(4-tert-butyl-2-pyridyl)pyridine, and Ir{dF(CF₃)ppy}₂(dtbpy)PF₆ (0.086 g, 0.077 mmol) in DME (80 mL) was sparged with N₂ for 15 min. The nickel solution was added to a mixture of tert-butyl 3-(bromomethyl)pyrrolidine-1-carboxylate (2.03 g, 7.68 mmol), 2-bromo-5-fluoropyrimidine (1.70 g, 9.61 mmol), tris(trimethylsilyl)silane (2.87 g, 11.5 mmol, 3.54 mL), and lithium hydroxide (0.736 mg, 30.7 mmol). After the mixture was sparged with N₂ (15 min), the reaction was irradiated with blue LEDs (48 watts 450 hv) overnight at 40° C. Celite was added to the reaction, and the mixture was filtered and concentrated in vacuo. The residue was purified over SiO₂ (0-100% EtOAc:heptane) to afford the title compound (0.760 g). LCMS (ESI): [M-t-Bu] 226. ¹HNMR: (500 MHz, CDCl₃) δ 8.39 (br d, J=9.46 Hz, 2H), 3.30-3.46 (m, 2H), 3.10-3.21 (m, 1H), 2.85-2.96 (m, 3H), 2.54-2.66 (m, 1H), 1.80-1.91 (m, 1H), 1.42-1.57 (m, 1H), 1.27-1.35 (m, 9H).

Intermediate 6

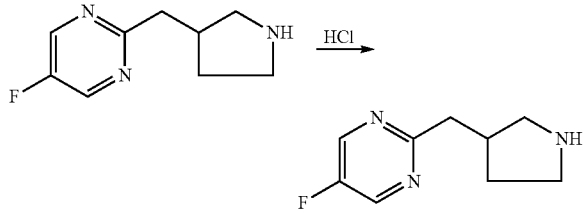

5-fluoro-2-(pyrrolidin-3-ylmethyl)pyrimidine hydrochloride

A solution of HCl in dioxane (4.0 M, 6.75 mL, 27.0 mmol) was added to a solution of tert-butyl 3-[(5-fluoropyrimidin-2-yl)methyl]pyrrolidine-1-carboxylate (0.760 g, 2.70 mmol) in CH$_2$Cl$_2$ (40.0 mL). After 2 h, the solution was decanted off. The residue was dissolved in MeOH and concentrated in vacuo to afford the title compound. LCMS (ESI): [M+H] 182.

Examples 2-1 and 2-2

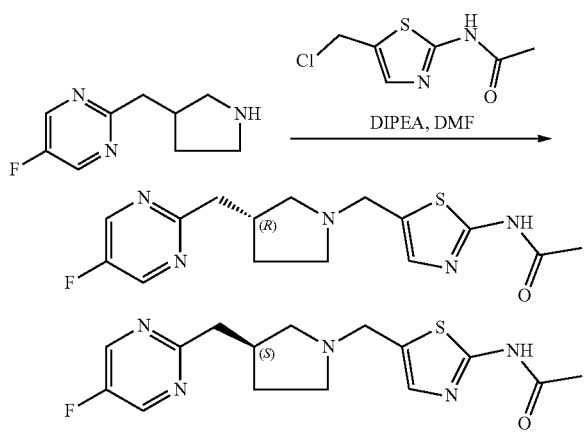

(R)-N-(5-((3-((5-fluoropyrimidin-2-yl)methyl)pyrrolidin-1-yl)methyl)thiazol-2-yl)acetamide and (S)—N-(5-((3-((5-fluoropyrimidin-2-yl)methyl)pyrrolidin-1-yl)methyl)thiazol-2-yl)acetamide Absolute configuration assigned arbitrarily. N-[5-(chloromethyl)thiazol-2-yl]acetamide (0.428 g, 2.25 mmol) was added to a solution of 5-fluoro-2-(pyrrolidin-3-ylmethyl)pyrimidine hydrochloride (0.489 g, 2.25 mmol) and diisopropylethylamine (1.45 g, 11.2 mmol, 1.96 mL) in DMF (5.00 mL). After 2 h, the mixture was concentrated in vacuo. The residue was dissolved in CH$_2$Cl$_2$, washed with saturated NaHCO$_3$ (aq) and concentrated in vacuo. The residue was purified over SiO$_2$ (40 g, 0-15% CH$_2$C$_2$:MeOH) to afford the title compound as a racemic mixture (0.411 g, 54%). The enantiomers were separated using chiral SFC. Column: CHIRALPAK AD-H 30×250 mm, Sum. Method: 35% Isopropanol w/ 0.1% diethyl amine in C$_{o2}$ at 100 mL/min.

Peak 1: 0.137 g. LCMS: [M+H] 336. $^1$HNMR: (500 MHz, CDCl$_3$) δ 12.07 (br s, 1H), 8.48-8.59 (m, 2H), 7.22 (s, 1H), 3.79 (s, 2H), 3.05 (d, J=7.32 Hz, 2H), 2.74-2.88 (m, 2H), 2.67-2.74 (m, 1H), 2.58-2.64 (m, 1H), 2.35 (dd, J=8.39, 6.56 Hz, 1H), 2.32 (s, 3H), 1.98-2.07 (m, 1H), 1.61 (ddt, J=12.63, 8.16, 6.16, 6.16 Hz, 1H).

Peak 2. 0.124 g. LCMS: [M+H] 336. $^1$HNMR: (500 MHz, CDCl$_3$) δ 11.56 (br s, 1H), 8.53 (s, 2H), 7.22 (s, 1H), 3.79 (s, 2H), 3.05 (d, J=7.17 Hz, 2H), 2.75-2.87 (m, 2H), 2.68-2.74 (m, 1H), 2.60 (td, J=8.58, 6.03 Hz, 1H), 2.32-2.37 (m, 1H), 2.32 (s, 3H), 1.99-2.08 (m, 1H), 1.57-1.65 (m, 1H).

Example 2-3

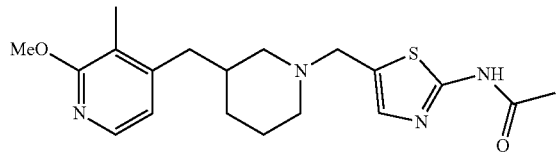 [SMILES: COc1nccc(CC2CCCN(Cc3cnc(NC(C)=O)s3)C2)c1C]

N-(5-((3-((2-methoxy-3-methylpyridin-4-yl)methyl)piperidin-1-yl)methyl)thiazol-2-yl)acetamide The title compound was prepared in an analogous manner of that in scheme 2 from tert-butyl 3-(bromomethyl)piperidine-1-carboxylate, 4-bromo-2-methoxy-3-methylpyridine, and N-[5-(chloromethyl)thiazol-2-yl]acetamide. LCMS (ESI): [M+H] 376. $^1$HNMR: (500 MHz, CDCl$_3$) δ 7.79 (d, J=5.49 Hz, 1H), 7.21 (s, 1H), 6.70 (d, J=4.88 Hz, 1H), 3.89 (s, 3H), 3.67 (s, 1H), 3.60-3.70 (m, 1H), 2.71-2.89 (m, 2H), 2.47-2.60 (m, 2H), 2.20 (s, 3H), 2.12 (s, 3H), 2.06 (br t, J=11.29 Hz, 1H), 1.79-1.93 (m, 2H), 1.62-1.75 (m, 2H), 1.46-1.60 (m, 1H), 1.46-1.60 (m, 1H), 0.94-1.12 (m, 1H).

Example 2-4

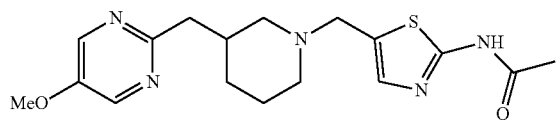 [SMILES: COc1cnc(CC2CCCN(Cc3cnc(NC(C)=O)s3)C2)nc1]

N-(5-((3-((5-methoxypyrimidin-2-yl)methyl)piperidin-1-yl)methyl)thiazol-2-yl)acetamide The title compound was prepared in an analogous manner of that in scheme 2 from tert-butyl 3-(bromomethyl)piperidine-1-carboxylate, 2-bromo-5-methoxypyrimidine, and N-[5-(chloromethyl)thiazol-2-yl]acetamide. LCMS (ESI): [M+H] 362. $^1$HNMR: (500 MHz, CDCl$_3$) δ 11.71 (br s, 1H), 8.33 (s, 2H), 7.18 (s, 1H), 3.90 (s, 3H), 3.73-3.56 (m, 2H), 2.95-2.70 (m, 4H), 2.30 (s, 3H), 2.27-2.16 (m, 1H), 2.06-1.93 (m, 1H), 1.93-1.83 (m, 1H), 1.73-1.62 (m, 2H), 1.56 (m, 1H), 1.11-0.94 (m, 1H).

Example 2-5

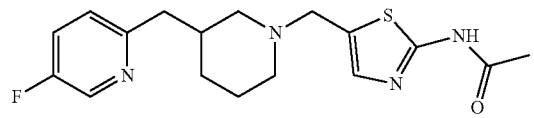 [SMILES: CC(=O)Nc1ncc(CN2CCCC(Cc3ccc(F)cn3)C2)s1]

N-(5-((3-((5-fluoropyridin-2-yl)methyl)piperidin-1-yl)methyl)thiazol-2-yl)acetamide The title compound was prepared in an analogous manner of that in scheme 2 from tert-butyl 3-(bromomethyl)piperidine-1-carboxylate, 2-bromo-5-fluoropyridine, and N-[5-(chloromethyl)thiazol-2-yl]acetamide. LCMS (ESI): [M+H]

349. ¹HNMR: (500 MHz, CDCl₃) δ 12.58 (br s, 1H), 8.44 (d, J=3.1 Hz, 1H), 7.58 (br d, J=11.0 Hz, 1H), 7.51 (dt, J=3.1, 8.2 Hz, 1H), 7.29 (dd, J=4.3, 9.2 Hz, 1H), 4.52-4.25 (m, 2H), 3.70-3.43 (m, 2H), 2.92-2.75 (m, 1H), 2.63-2.41 (m, 2H), 2.36 (s, 3H), 2.24 (m, 1H), 2.18-2.05 (m, 1H), 2.05-1.83 (m, 3H), 1.34-1.13 (m, 1H).

Example 2-6

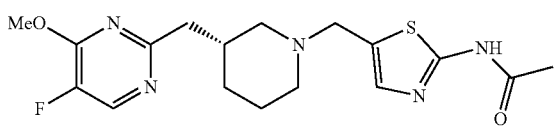 [SMILES: COc1nc(C[C@H]2CCCN(Cc3cnc(NC(C)=O)s3)C2)ncc1F]

(R)-N-(5-((3-((5-fluoro-4-methoxypyrimidin-2-yl)methyl)piperidin-1-yl)methyl)thiazol-2-yl)acetamide The title compound was prepared in an analogous manner of that in scheme 2 from tert-butyl (S)-3-(bromomethyl)piperidine-1-carboxylate, 2-chloro-5-fluoro-4-methoxypyrimidine and N-[5-(chloromethyl)thiazol-2-yl]acetamide. LCMS (ESI): [M+H] 380.

Example 2-7

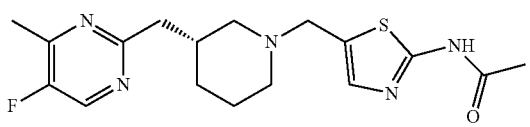 [SMILES: CC(=O)Nc1ncc(CN2CCC[C@H](Cc3ncc(F)c(C)n3)C2)s1]

(R)-N-(5-((3-((5-fluoro-4-methylpyrimidin-2-yl)methyl)piperidin-1-yl)methyl)thiazol-2-yl)acetamide The title compound was prepared in an analogous manner of that in scheme 2 from tert-butyl (S)-3-(bromomethyl)piperidine-1-carboxylate, 2-chloro-5-fluoro-4-methylpyrimidine and N-[5-(chloromethyl)thiazol-2-yl]acetamide. LCMS (ESI): [M+H] 381.

Example 2-8

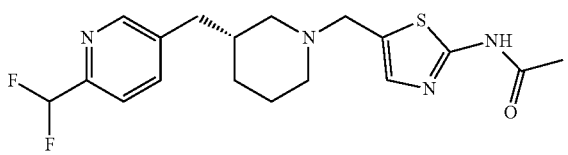 [SMILES: CC(=O)Nc1ncc(CN2CCC[C@H](Cc3ccc(C(F)F)nc3)C2)s1]

(R)-N-(5-((3-((6-(difluoromethyl)pyridin-3-yl)methyl)piperidin-1-yl)methyl)thiazol-2-yl)acetamide The title compound was prepared in an analogous manner of that in scheme 2 from tert-butyl (S)-3-(bromomethyl)piperidine-1-carboxylate, 5-bromo-2-(difluoromethyl)pyridine and N-[5-(chloromethyl)thiazol-2-yl]acetamide. LCMS (ESI): [M+H] 381. ¹HNMR: (500 MHz, CDCl₃) δ 11.58 (br s, 1H), 8.43 (d, J=1.8 Hz, 1H), 7.62 (dd, J=2.4, 7.9 Hz, 1H), 7.58-7.53 (m, 1H), 7.18 (s, 1H), 6.63 (t, J=55.5 Hz, 1H), 3.71-3.57 (m, 2H), 2.75 (br d, J=7.9 Hz, 2H), 2.64 (dd, J=7.6, 13.7 Hz, 1H), 2.54 (dd, J=7.6, 13.7 Hz, 1H), 2.31 (s, 3H), 2.06 (br t, J=10.1 Hz, 1H), 1.98-1.79 (m, 2H), 1.73-1.58 (m, 2H), 1.56-1.46 (m, 1H), 1.09-0.89 (m, 1H).

Example 2-9

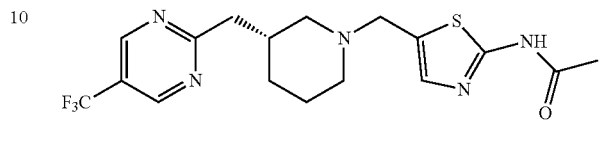

(R)-N-(5-((3-((5-(trifluoromethyl)pyrimidin-2-yl)methyl)piperidin-1-yl)methyl)thiazol-2-yl)acetamide The title compound was prepared in an analogous manner of that in scheme 2 from tert-butyl (S)-3-(bromomethyl)piperidine-1-carboxylate, 2-bromo-5-(trifluoromethyl)pyrimidine, and N-[5-(chloromethyl)thiazol-2-yl]acetamide. LCMS (ESI): [M+H] 400. ¹HNMR: (500 MHz, CDCl₃) δ 11.58 (br s, 1H), 8.90 (s, 2H), 7.18 (s, 1H), 3.72-3.59 (m, 2H), 3.02-2.91 (m, 2H), 2.80 (br t, J=11.3 Hz, 2H), 2.30 (s, 3H), 2.06 (br t, J=10.1 Hz, 1H), 1.94 (br t, J=10.1 Hz, 1H), 1.74-1.65 (m, 2H), 1.64-1.52 (m, 2H), 1.15-1.01 (m, 1H).

Example 2-10

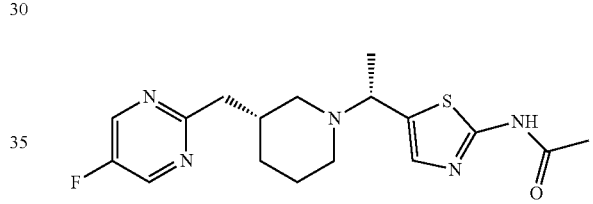

N-(5-((R)-1-((R)-3-((5-fluoropyrimidin-2-yl)methyl)piperidin-1-yl)ethyl)thiazol-2-yl)acetamide Relative configuration assigned arbitrarily. The title compound was prepared in an analogous manner of that in scheme 2 from tert-butyl (S)-3-(bromomethyl)piperidine-1-carboxylate, 2-bromo-5-(trifluoromethyl)pyrimidine, and N-(5-(1-chloroethyl)thiazol-2-yl)acetamide. The chiral separation method: Column: CHIRALPAK IA 30×250 mm, 5um; Method: 40% Ethanol with 0.1% diethyl amine in CO₂ (flow rate: 100 mL/min), ABPR 120 bar, MBPR 40 psi. The product was peak 1. LCMS (ESI): [M+H] 364. ¹HNMR: (500 MHz, CDCl₃) δ 11.34 (br s, 1H), 8.53 (s, 2H), 7.10 (s, 1H), 3.91 (q, J=6.7 Hz, 1H), 2.91-2.79 (m, 3H), 2.70 (m, 1H), 2.30 (s, 3H), 2.27-2.18 (m, 1H), 2.14-2.01 (m, 2H), 1.71-1.50 (m, 4H), 1.39 (d, J=6.7 Hz, 3H), 1.08-0.96 (m, 1H).

Example 2-11

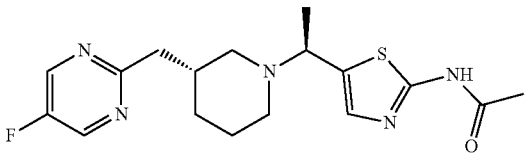 [SMILES: CC(=O)Nc1ncc([C@H](C)N2CCC[C@H](Cc3ncc(F)cn3)C2)s1]

N-(5-((S)-1-((R)-3-((5-fluoropyrimidin-2-yl)methyl)
piperidin-1-yl)ethyl)thiazol-2-yl)acetamide Relative configuration assigned arbitrarily. The chiral separation method: Column: CHIRALPAK IA 30×250 mm, 5 um; Method: 40% Ethanol with 0.1% diethyl amine in $CO_2$ (flow rate: 100 mL/min), ABPR 120 bar, MBPR 40 psi. The product was peak 2. LCMS (ESI): [M+H] 364.

Example 2-12

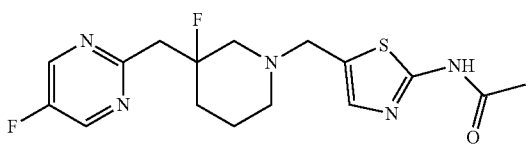 [SMILES: CC(=O)Nc1ncc(CN2CCCC(F)(Cc3ncc(F)cn3)C2)s1]

N-(5-((3-fluoro-3-((5-fluoropyrimidin-2-yl)methyl)
piperidin-1-yl)methyl)thiazol-2-yl)acetamide The title compound was prepared in an analogous manner of that in scheme 2 from tert-butyl 3-(bromomethyl)-3-fluoropiperidine-1-carboxylate, 2-bromo-5-fluoropyrimidine, and N-[5-(chloromethyl)thiazol-2-yl]acetamide. LCMS (ESI): [M+H] 368. $^1$HNMR: (500 MHz, $CDCl_3$) δ 12.24 (s, 1H), 8.56 (s, 2H), 7.23 (s, 1H), 3.70-3.86 (m, 2H), 3.30-3.52 (m, 2H), 2.61-2.75 (m, 2H), 2.51 (br s, 2H), 1.80-1.89 (m, 1H), 1.67-1.79 (m, 3H).

Example 2-13

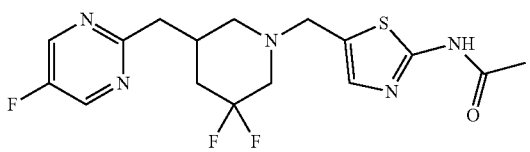 [SMILES: CC(=O)Nc1ncc(CN2CC(Cc3ncc(F)cn3)CC(F)(F)C2)s1]

N-(5-((3,3-difluoro-5-((5-fluoropyrimidin-2-yl)
methyl)piperidin-1-yl)methyl)thiazol-2-yl)acetamide The title compound was prepared in an analogous manner of that in scheme 2 from tert-butyl 5-(bromomethyl)-3,3-difluoropiperidine-1-carboxylate, 2-bromo-5-fluoropyrimidine, and N-[5-(chloromethyl)thiazol-2-yl]acetamide. LCMS (ESI): [M+H] 386. $^1$HNMR: (500 MHz, $CDCl_3$) δ 12.23 (br s, 1H), 8.54 (s, 2H), 7.22 (s, 1H), 3.72-3.88 (m, 2H), 2.98-3.08 (m, 2H), 2.91-2.95 (m, 2H), 2.52-2.65 (m, 1H), 2.34-2.43 (m, 1H), 2.11-2.21 (m, 1H), 2.07 (t, J=10.83 Hz, 1H), 1.45-1.61 (m, 1H).

Example 2-14

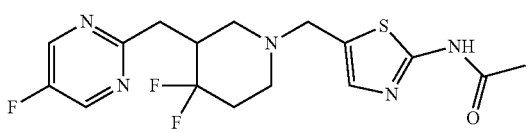 [SMILES: CC(=O)Nc1ncc(CN2CCC(F)(F)C(Cc3ncc(F)cn3)C2)s1]

N-(5-((4,4-difluoro-3-((5-fluoropyrimidin-2-yl)
methyl)piperidin-1-yl)methyl)thiazol-2-yl)acetamide The title compound was prepared in an analogous manner of that in scheme 2 from tert-butyl 3-(bromomethyl)-4,4-difluoropiperidine-1-carboxylate, 2-bromo-5-fluoropyrimidine, and N-[5-(chloromethyl)thiazol-2-yl]acetamide. LCMS (ESI): [M+H] 386. $^1$HNMR: (500 MHz, $CDCl_3$) δ 12.25 (br s, 1H), 8.32-8.35 (m, 1H), 8.33 (s, 1H), 6.99 (s, 1 H), 3.51-3.57 (m, 1H), 3.43-3.48 (m, 1H), 3.19 (dd, J=14.96, 3.36 Hz, 1H), 2.71-2.77 (m, 1H), 2.55-2.68 (m, 3H), 2.16-2.26 (m, 1H), 2.13 (s, 3H), 1.76-1.97 (m, 2H).

Example 2-15

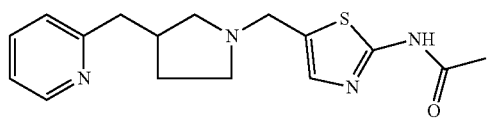 [SMILES: CC(=O)Nc1ncc(CN2CCC(Cc3ccccn3)C2)s1]

N-(5-((3-(pyridin-2-ylmethyl)pyrrolidin-1-yl)
methyl)thiazol-2-yl)acetamide

The title compound was prepared in an analogous manner of that in scheme 2 from tert-butyl 3-(bromomethyl)pyrrolidine-1-carboxylate, 2-bromopyridine, and N-[5-(chloromethyl)thiazol-2-yl]acetamide. LCMS (ESI): [M+H] 317. $^1$HNMR: (500 MHz, $CDCl_3$) δ 12.33 (br s, 1H), 8.48-8.57 (m, 1H), 7.59 (td, J=7.63, 1.83 Hz, 1H), 7.21 (s, 1H), 7.14 (d, J=7.78 Hz, 1H), 7.11 (ddd, J=7.48, 4.88, 1.07 Hz, 1H), 3.73-3.84 (m, 2H), 2.87 (d, J=7.48 Hz, 2H), 2.60-2.80 (m, 4H), 2.33-2.37 (m, 1H), 2.32 (s, 3H), 1.96-2.05 (m, 1H), 1.57 (ddt, J=12.66, 8.20, 6.28, 6.28 Hz, 1H).

Example 2-16

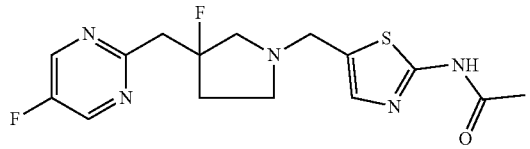 [SMILES: CC(=O)Nc1ncc(CN2CCC(F)(Cc3ncc(F)cn3)C2)s1]

N-(5-((3-fluoro-3-((5-fluoropyrimidin-2-yl)methyl)
pyrrolidin-1-yl)methyl)thiazol-2-yl)acetamide The title compound was prepared in an analogous manner of that in scheme 2 from tert-butyl 3-(bromomethyl)-3-fluoropyrrolidine-1-carboxylate, 2-bromo-5-fluoropyrimidine, and N-[5-(chloromethyl)thiazol-2-yl]acetamide. LCMS (ESI): [M+H] 354. $^1$HNMR: (500 MHz, $CDCl_3$) δ 11.49 (br s, 1H), 8.58 (s, 2H), 7.23 (s, 1H), 3.83 (d, J=1.83 Hz, 2H), 3.38-3.53 (m, 2H), 3.08-3.22 (m, 1H), 2.79-2.94 (m, 2H), 2.71 (td, J=8.28, 4.35 Hz, 1H), 2.31-2.34 (m, 3H), 2.11-2.31 (m, 2H).

Example 2-17

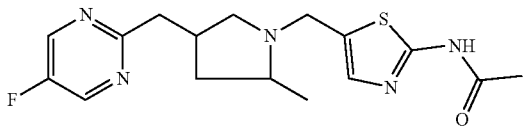 [SMILES: CC(=O)Nc1ncc(CN2CC(Cc3ncc(F)cn3)CC2C)s1]

N-(5-((4-((5-fluoropyrimidin-2-yl)methyl)-2-methylpyrrolidin-1-yl)methyl)thiazol-2-yl)acetamide The title compound was prepared in an analogous manner of that in scheme 2 from tert-butyl 4-(bromomethyl)-2-methylpyrrolidine-1-carboxylate, 2-bromo-5-fluoropyrimidine, and N-[5-(chloromethyl)thiazol-2-yl]acetamide. The resulting enantiomers were separated using chiral SFC. LCMS (ESI): [M+H] 350. $^1$HNMR: (400 MHz, Methanol-d4) δ 8.59-8.65 (m, 2H), 7.23 (d, J=5.52 Hz, 1H), 4.03-4.09 (m, 1H), 3.55 (t, J=14.56 Hz, 1H), 2.81-3.13 (m, 3H), 2.45-2.80 (m, 3H), 2.20 (d, J=1.00 Hz, 3H), 2.07-2.16 (m, 1H), 1.60-1.86 (m, 1H), 1.16 (dd, J=6.02, 8.28 Hz, 3H).

Example 2-18

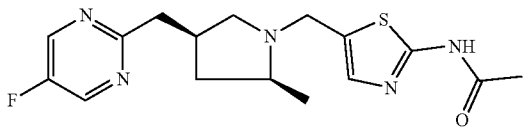 [SMILES: CC(=O)Nc1ncc(CN2C[C@H](Cc3ncc(F)cn3)C[C@@H]2C)s1]

N-(5-(((2S,4S)-4-((5-fluoropyrimidin-2-yl)methyl)-2-methylpyrrolidin-1-yl)methyl)thiazol-2-yl)acetamide Relative and absolute configuration assigned arbitrarily. The chiral separation method: Column: CHIRALPAK AD-H; Method: 40% Ethanol with 0.1% diethyl amine in $CO_2$ (flow rate: 100 mL/min), ABPR 120 bar, MBPR 40 psi. The product was peak 4. LCMS (ESI): [M+H] 350. $^1$HNMR: (500 MHz, CDCl$_3$) δ 12.28 (br s, 1H), 8.52 (s, 2H), 7.20 (s, 1H), 4.05 (dd, J=14.27, 0.99 Hz, 1H), 3.54 (d, J=14.50 Hz, 1H), 3.00-3.10 (m, 2H), 2.87 (dd, J=9.54, 3.89 Hz, 1H), 2.59-2.69 (m, 1H), 2.49-2.59 (m, 2H), 2.33 (s, 3H), 2.10 (ddd, J=12.51, 8.24, 6.41 Hz, 1H), 1.27-1.35 (m, 1H), 1.17 (d, J=5.95 Hz, 3H).

Example 2-19

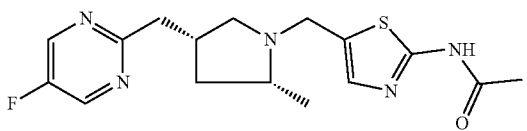 [SMILES: CC(=O)Nc1ncc(CN2C[C@@H](Cc3ncc(F)cn3)C[C@H]2C)s1]

N-(5-(((2R,4R)-4-((5-fluoropyrimidin-2-yl)methyl)-2-methylpyrrolidin-1-yl)methyl)thiazol-2-yl)acetamide Relative and absolute configuration assigned arbitrarily. The chiral separation method used: Column: CHIRALPAK AD-H; Method: 40% Ethanol with 0.1% diethyl amine in $CO_2$ (flow rate: 100 mL/min), ABPR 120 bar, MBPR 40 psi. The product was peak 3. LCMS (ESI): [M+H] 350. $^1$HNMR: (500 MHz, CDCl$_3$) δ 12.32 (br s, 1H), 8.51 (s, 2H), 7.20 (s, 1H), 4.06 (dd, J=14.19, 0.92 Hz, 1H), 3.53 (d, J=14.19 Hz, 1H), 3.14 (dd, J=9.00, 7.17 Hz, 1H), 2.91-3.03 (m, 2H), 2.69-2.80 (m, 1H), 2.57-2.66 (m, 1H), 2.32 (s, 3H), 2.06 (t, J=9.00 Hz, 1H), 1.72-1.79 (m, 2H), 1.64-1.72 (m, 1H), 1.15 (d, J=6.10 Hz, 3H).

Example 2-20

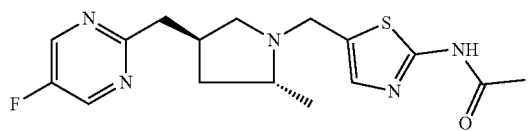 [SMILES: CC(=O)Nc1ncc(CN2C[C@H](Cc3ncc(F)cn3)C[C@H]2C)s1]

N-(5-(((2R,4S)-4-((5-fluoropyrimidin-2-yl)methyl)-2-methylpyrrolidin-1-yl)methyl)thiazol-2-yl)acetamide Relative and absolute configuration assigned arbitrarily. The chiral separation method: Column: CHIRALPAK AD-H; Method: 40% Ethanol with 0.1% diethyl amine in $CO_2$ (flow rate: 100 mL/min), ABPR 120 bar, MBPR 40 psi. The product was peak 2. LCMS (ESI): [M+H] 350. $^1$HNMR: (500 MHz, CDCl$_3$) δ 12.50 (br s, 1H), 8.50 (s, 2H), 7.19 (s, 1H), 4.05 (dd, J=14.11, 1.14 Hz, 1H), 3.53 (d, J=14.34 Hz, 1H), 3.14 (dd, J=9.08, 7.10 Hz, 1H), 2.96 (d, J=7.02 Hz, 2H), 2.74 (ddqd, J=9.92, 9.00, 7.10, 7.02, 7.02, 6.26 Hz, 1H), 2.62 (ddq, J=7.78, 7.78, 6.10, 6.10, 6.10 Hz, 1H), 2.30-2.34 (m, 3H), 2.06 (t, J=9.00 Hz, 1H), 1.76 (ddd, J=12.97, 7.78, 6.26 Hz, 1H), 1.68 (ddd, J=12.82, 9.92, 7.78 Hz, 1H), 1.15 (d, J=5.95 Hz, 3H).

Example 2-21

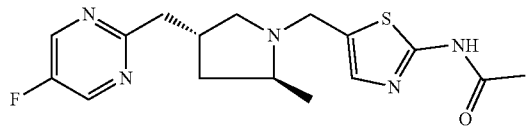 [SMILES: CC(=O)Nc1ncc(CN2C[C@@H](Cc3ncc(F)cn3)C[C@@H]2C)s1]

N-(5-(((2S,4R)-4-((5-fluoropyrimidin-2-yl)methyl)-2-methylpyrrolidin-1-yl)methyl)thiazol-2-yl)acetamide Relative and absolute configuration assigned arbitrarily. The chiral separation method: Column: CHIRALPAK AD-H; Method: 40% Ethanol with 0.1% diethyl amine in $CO_2$ (flow rate: 100 mL/min), ABPR 120 bar, MBPR 40 psi. The product was peak 1. LCMS (ESI): [M+H] 350. $^1$HNMR: (500 MHz, CDCl$_3$) δ 12.46 (br s, 1H), 8.50 (d, J=0.61 Hz, 2H), 7.18 (t, J=0.99 Hz, 1H), 4.03 (dd, J=14.27, 1.14 Hz, 1H), 3.53 (d, J=14.50 Hz, 1H), 2.99-3.08 (m, 2H), 2.57-2.67 (m, 1H), 2.55 (ddq, J=9.46, 6.41, 6.10, 6.10, 6.10 Hz, 1H), 2.47-2.52 (m, 1H), 2.31 (s, 3H), 2.08 (ddd, J=12.47, 8.28, 6.41 Hz, 1H), 1.29 (ddd, J=12.66, 9.46, 7.32 Hz, 1H), 1.15 (d, J=6.10 Hz, 3H).

Example 2-22

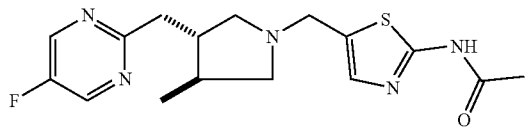

N-(5-(((trans)-3-((5-fluoropyrimidin-2-yl)methyl)-4-methylpyrrolidin-1-yl)methyl)thiazol-2-yl)acetamide The title compound was prepared in an analogous manner of that in scheme 2 from tert-butyl(trans)-3-(bromomethyl)-4-methylpyrrolidine-1-carboxylate, 2-bromo-5-fluoropyrimidine, and N-[5-(chloromethyl)thiazol-2-yl]acetamide. LCMS (ESI): [M+H] 350. $^1$HNMR: (500 MHz, CDCl$_3$) δ 12.36 (br s, 1H), 8.44 (s, 2H), 7.12 (s, 1H), 3.67 (q, J=13.89 Hz, 2H), 3.04 (dd, J=13.89, 5.95 Hz, 1H), 2.89 (dd, J=13.66, 9.08 Hz, 1H), 2.79 (t, J=8.24 Hz, 1H), 2.68 (t, J=8.62 Hz, 1H), 2.44 (dd, J=9.08, 6.79 Hz, 1H), 2.24 (s, 3H), 2.16-2.22 (m, 2H), 1.93 (spt, J=6.99 Hz, 1H), 0.90 (d, J=6.71 Hz, 3H).

Example 2-23

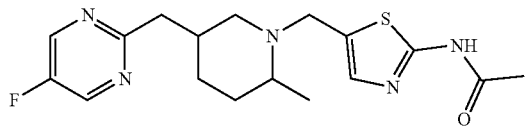 [SMILES: CC(=O)Nc1ncc(CN2CC(Cc3ncc(F)cn3)CCC2C)s1]

N-(5-((5-((5-fluoropyrimidin-2-yl)methyl)-2-methylpiperidin-1-yl)methyl)thiazol-2-yl)acetamide The title compound was prepared in an analogous manner of that in scheme 2 from tert-butyl 5-(bromomethyl)-2-methylpiperidine-1-carboxylate, 2-bromo-5-fluoropyrimidine, and N-[5-(chloromethyl)thiazol-2-yl]acetamide. The cis and trans diastereomers were separated over silica gel. The resulting enantiomers were separated using chiral SFC.

Example 2-24

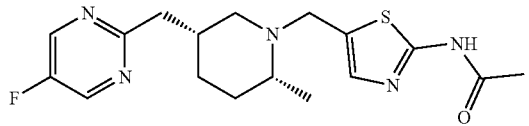 [SMILES: CC(=O)Nc1ncc(CN2C[C@@H](Cc3ncc(F)cn3)CC[C@H]2C)s1]

N-(5-(((2R,5R)-5-((5-fluoropyrimidin-2-yl)methyl)-2-methylpiperidin-1-yl)methyl)thiazol-2-yl)acetamide Absolute configuration assigned arbitrarily. The chiral separation method: Column: CHIRALPAK IA 30×250 mm, Sum; Method: 40% Ethanol with 0.1% diethyl amine in CO$_2$ (flow rate: 100 mL/min), ABPR 120 bar, MBPR 40 psi. The product was peak 1. LCMS (ESI): [M+H] 364. $^1$HNMR: (400 MHz, Methanol-d4) δ 8.59 (d, J=0.75 Hz, 2H), 7.17 (s, 1H), 3.84 (dd, J=0.75, 14.05 Hz, 1H), 3.63 (d, J=14.31 Hz, 1H), 2.89-3.04 (m, 2H), 2.68-2.81 (m, 1H), 2.46-2.55 (m, 1H), 2.33-2.42 (m, 1H), 2.22-2.31 (m, 1H), 2.19 (s, 3H), 1.63-1.74 (m, 1H), 1.48-1.63 (m, 2H), 1.36-1.47 (m, 1H), 1.11 (d, J=6.53 Hz, 3H).

Example 2-25

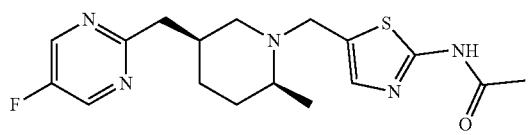 [SMILES: CC(=O)Nc1ncc(CN2C[C@H](Cc3ncc(F)cn3)CC[C@@H]2C)s1]

N-(5-(((2S,5S)-5-((5-fluoropyrimidin-2-yl)methyl)-2-methylpiperidin-1-yl)methyl)thiazol-2-yl)acetamide Absolute configuration assigned arbitrarily. The chiral separation method: Column: CHIRALPAK IA 30×250 mm, Sum; Method: 40% Ethanol with 0.1% diethyl amine in CO$_2$ (flow rate: 100 mL/min), ABPR 120 bar, MBPR 40 psi. The product was peak 2. LCMS (ESI): [M+H] 364. $^1$HNMR: (400 MHz, Methanol-d4) δ 8.59 (d, J=0.75 Hz, 2H), 7.17 (s, 1H), 3.79-3.89 (m, 1H), 3.62 (d, J=14.31 Hz, 1H), 2.89-3.04 (m, 2H), 2.68-2.80 (m, 1H), 2.46-2.54 (m, 1H), 2.34-2.41 (m, 1H), 2.22-2.32 (m, 1H), 2.19 (s, 3H), 1.63-1.74 (m, 1H), 1.48-1.63 (m, 2H), 1.36-1.48 (m, 1H), 1.11 (d, J=6.53 Hz, 3H).

Example 2-26

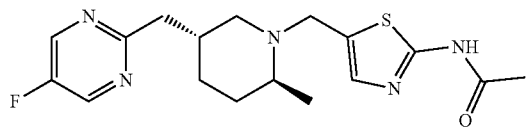 [SMILES: CC(=O)Nc1ncc(CN2C[C@@H](Cc3ncc(F)cn3)CC[C@@H]2C)s1]

N-(5-(((2S,5R)-5-((5-fluoropyrimidin-2-yl)methyl)-2-methylpiperidin-1-yl)methyl)thiazol-2-yl)acetamide Absolute configuration assigned arbitrarily. The chiral separation method: Column: CHIRALPAK IA 30×250 mm, Sum; Method: 40% Ethanol with 0.1% diethyl amine in CO$_2$ (flow rate: 100 mL/min), ABPR 120 bar, MBPR 40 psi. The product was peak 1. LCMS (ESI): [M+H] 364. $^1$HNMR: (400 MHz, Methanol-d4) δ 8.62 (d, J=0.75 Hz, 2H), 7.21 (s, 1H), 3.99 (d, J=14.81 Hz, 1H), 3.79 (d, J=14.81 Hz, 1H), 2.72-2.86 (m, 3H), 2.11-2.33 (m, 5H), 1.87-1.97 (m, 1H), 1.63-1.74 (m, 2H), 1.28-1.44 (m, 1H), 1.21 (d, J=6.02 Hz, 3H), 0.99-1.15 (m, 1H).

Example 2-27

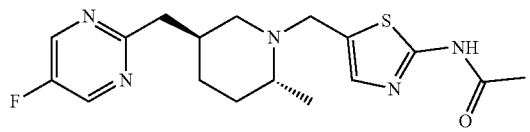 [SMILES: CC(=O)Nc1ncc(CN2C[C@H](Cc3ncc(F)cn3)CC[C@H]2C)s1]

N-(5-(((2R,5S)-5-((5-fluoropyrimidin-2-yl)methyl)-2-methylpiperidin-1-yl)methyl)thiazol-2-yl)acetamide Absolute configuration assigned arbitrarily. The chiral separation method: Column: CHIRALPAK IA 30×250 mm, 5um; Method: 40% Ethanol with 0.1% diethyl amine in CO$_2$ (flow rate: 100 mL/min), ABPR 120 bar, MBPR 40 psi. The product was peak 2. LCMS (ESI): [M+H] 364. $^1$HNMR: (400 MHz, Methanol-d4) δ 8.62 (s, 2H), 7.21 (s, 1H), 3.99 (d, J=14.81 Hz, 1H), 3.79 (d, J=14.81 Hz, 1H), 2.73-2.85 (m, 3H), 2.12-2.33 (m, 5H), 1.87-1.96 (m, 1H), 1.63-1.73 (m, 2H), 1.28-1.42 (m, 1H), 1.21 (d, J=6.27 Hz, 3H), 0.99-1.15 (m, 1H).

Example 2-28

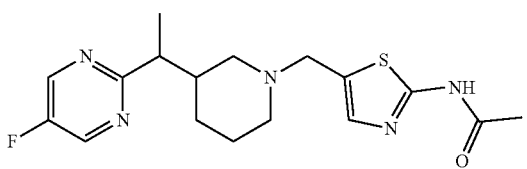 [SMILES: CC(=O)Nc1ncc(CN2CCCC(C(C)c3ncc(F)cn3)C2)s1]

N-(5-((5-((5-fluoropyrimidin-2-yl)methyl)-2-methylpiperidin-1-yl)methyl)thiazol-2-yl)acetamide The title compound was prepared in an analogous manner of that in scheme 2 from tert-butyl 3-(1-bromoethyl)piperidine-1-carboxylate, 2-bromo-5-fluoropyrimidine, and N-[5-(chloromethyl)thiazol-2-yl]acetamide. The resulting enantiomers were separated using chiral SFC.

Example 2-29

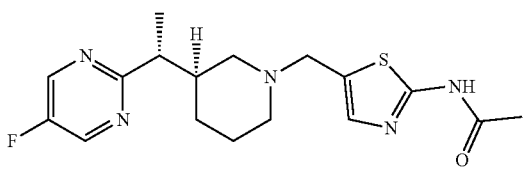 [SMILES: CC(=O)Nc1ncc(CN2CCC[C@@H]([C@@H](C)c3ncc(F)cn3)C2)s1]

N-(5-(((S)-3-((R)-1-(5-fluoropyrimidin-2-yl)ethyl)piperidin-1-yl)methyl)thiazol-2-yl)acetamide Relative and absolute configuration assigned arbitrarily. The chiral separation method: Column: CHIRALPAK IG 30×250 mm, 5um; 30% Ethanol w/ 0.1% DEA in CO$_2$ (flow rate: 100 mL/min), ABPR 120 bar, MBPR 40 psi, column temperature 40 deg. ° C. The product was peak 1. LCMS (ESI): [M+H] 364.

Example 2-30

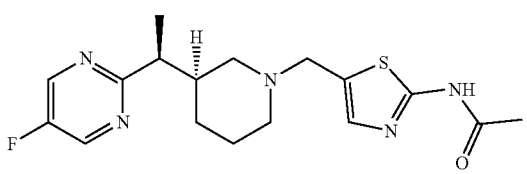 [SMILES: CC(=O)Nc1ncc(CN2CCC[C@@H]([C@H](C)c3ncc(F)cn3)C2)s1]

N-(5-(((S)-3-((S)-1-(5-fluoropyrimidin-2-yl)ethyl)piperidin-1-yl)methyl)thiazol-2-yl)acetamide Relative and absolute configuration assigned arbitrarily. The chiral separation method used: Column: CHIRALPAK IG 30×250 mm, 5um; 30% Ethanol w/ 0.1% DEA in CO$_2$ (flow rate: 100 mL/min), ABPR 120 bar, MBPR 40 psi, column temperature 40 deg ° C. The product was peak 2. LCMS (ESI): [M+H] 364.

Example 2-31

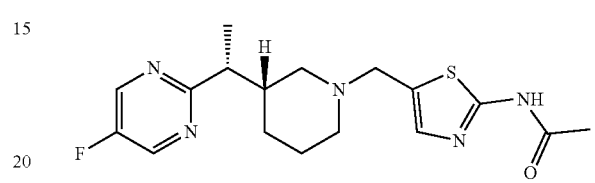

N-(5-(((R)-3-((R)-1-(5-fluoropyrimidin-2-yl)ethyl)piperidin-1-yl)methyl)thiazol-2-yl)acetamide Relative and absolute configuration assigned arbitrarily. The chiral separation method: CHIRALPAK IG 30×250 mm, 5um; 30% Ethanol w/ 0.1% DEA in CO$_2$ (flow rate: 100 mL/min), ABPR 120 bar, MBPR 40 psi, column temperature 40 deg ° C. The product was peak 3. LCMS (ESI): [M+H] 364.

Example 2-32

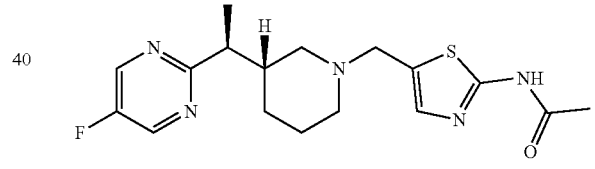

N-(5-(((R)-3-((S)-1-(5-fluoropyrimidin-2-yl)ethyl)piperidin-1-yl)methyl)thiazol-2-yl)acetamide Relative and absolute configuration assigned arbitrarily. The chiral separation method: Column: CHIRALPAK IG 30×250 mm, 5 um; 30% Ethanol w/ 0.1% DEA in CO$_2$ (flow rate: 100 mL/min), ABPR 120 bar, MBPR 40 psi, column temperature 40 deg ° C. The product was peak 4. LCMS (ESI): [M+H] 364.

Example 2-33

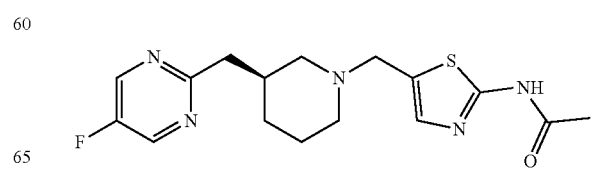

N-[5-[[(3S)-3-[(5-fluoropyrimidin-2-yl)methyl]-1-piperidyl]methyl]thiazol-2-yl]acetamide The title compound was prepared in an analogous manner of that in scheme 2 from tert-butyl (R)-3-(bromomethyl)piperidine-1-carboxylate, 2-bromo-5-fluoro-pyrimidine and N-[5-(chloromethyl)thiazol-2-yl]acetamide. LCMS (ESI): [M+H] 350. $^1$HNMR: (500 MHz, CDCl$_3$) δ 12.09 (br s, 1H), 8.52 (s, 2H), 7.18 (s, 1H), 3.59-3.71 (m, 2H), 2.86 (d, J=6.71 Hz, 2H), 2.81 (br t, J=10.68 Hz, 2H), 2.31 (s, 3H), 2.18-2.28 (m, 1H), 1.99-2.07 (m, 1H), 1.90 (br t, J=10.38 Hz, 1H), 1.64-1.73 (m, 2H), 1.51-1.61 (m, 1H), 1.00-1.09 (m, 1H).

Example 2-34

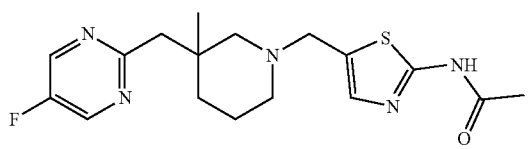 [SMILES: CC(=O)Nc1ncc(CN2CCCC(C)(Cc3ncc(F)cn3)C2)s1]

N-(5-((3-((5-fluoropyrimidin-2-yl)methyl)-3-methylpiperidin-1-yl)methyl)thiazol-2-yl)acetamide The title compound was prepared in an analogous manner of that in scheme 2 from tert-butyl 3-(bromomethyl)-3-methylpiperidine-1-carboxylate, 2-bromo-5-fluoropyrimidine, and N-(5-(chloromethyl)thiazol-2-yl)acetamide. LCMS: [M+H] 364. $^1$H NMR (400 MHz, METHANOL-d$_4$) δ 8.57-8.63 (m, 2H), 7.17 (s, 1H), 3.85 (d, J=14.31 Hz, 1H), 3.59-3.70 (m, 1H), 2.89-3.03 (m, 2H), 2.74 (br s, 1H), 2.45-2.56 (m, 1H), 2.33-2.43 (m, 1H), 2.26 (ddd, J=3.76, 7.53, 11.29 Hz, 1H), 2.19 (s, 3H), 1.64-1.74 (m, 1H), 1.49-1.63 (m, 2H), 1.39-1.48 (m, 1H), 1.12 (d, J=6.53 Hz, 3H).

Example 2-35

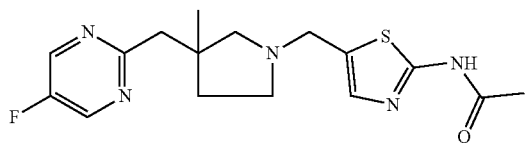 [SMILES: CC(=O)Nc1ncc(CN2CCC(C)(Cc3ncc(F)cn3)C2)s1]

N-(5-((3-((5-fluoropyrimidin-2-yl)methyl)-3-methylpyrrolidin-1-yl)methyl)thiazol-2-yl)acetamide The title compound was prepared in an analogous manner of that in scheme 2 from tert-butyl 3-(bromomethyl)-3-methylpyrrolidine-1-carboxylate, 2-bromo-5-fluoropyrimidine, and N-(5-(chloromethyl)thiazol-2-yl)acetamide. LCMS (ESI): [M+H] 350. $^1$H NMR (400 MHz, METHANOL-d4) δ 8.64 (d, J=0.75 Hz, 2H), 7.21 (s, 1H), 3.75 (s, 2H), 3.01 (s, 2H), 2.91 (d, J=9.54 Hz, 1H), 2.63 (dt, J=2.26, 7.03 Hz, 2H), 2.34 (d, J=9.54 Hz, 1H), 2.20 (s, 3H), 2.13 (td, J=7.28, 12.80 Hz, 1H), 1.58 (ddd, J=6.15, 7.22, 12.99 Hz, 1H), 1.10 (s, 3H).

Example 2-36

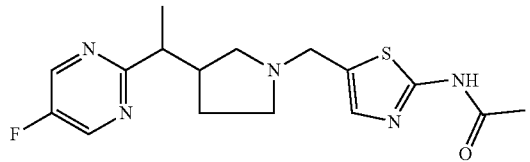 [SMILES: CC(=O)Nc1ncc(CN2CCC(C(C)c3ncc(F)cn3)C2)s1]

N-(5-((3-(1-(5-fluoropyrimidin-2-yl)ethyl)pyrrolidin-1-yl)methyl)thiazol-2-yl)acetamide The title compound was prepared in an analogous manner of that in scheme 2 from tert-butyl 3-(1-bromoethyl)pyrrolidine-1-carboxylate, 2-bromo-5-fluoropyrimidine, and N-(5-(chloromethyl)thiazol-2-yl)acetamide. LCMS (ESI): [M+H] 350. $^1$H NMR (400 MHz, METHANOL-d4) δ 8.69 (s, 1H), 8.63-8.77 (m, 1H), 7.51-7.64 (m, 1H), 4.50-4.70 (m, 2H), 3.41-3.91 (m, 1H), 2.69-3.26 (m, 4H), 2.28-2.55 (m, 1H), 2.22 (d, J=4.02 Hz, 3H), 1.91-2.12 (m, 1H), 1.54-1.87 (m, 1H), 1.26-1.42 (m, 3H).

Example 2-37

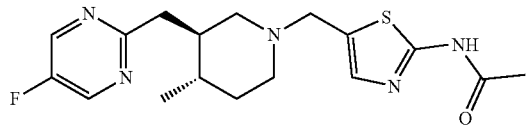 [SMILES: CC(=O)Nc1ncc(CN2CC[C@H](C)[C@@H](Cc3ncc(F)cn3)C2)s1]

N-(5-(((3S,4R)-3-((5-fluoropyrimidin-2-yl)methyl)-4-methylpiperidin-1-yl)methyl)thiazol-2-yl)acetamide The title compound was prepared in an analogous manner of that in scheme 2 from trans-tert-butyl 3-(bromomethyl)-4-methylpiperidine-1-carboxylate, 2-bromo-5-fluoropyrimidine, and N-(5-(chloromethyl)thiazol-2-yl)acetamide, followed by chiral separation; absolute configuration assigned arbitrarily. The chiral separation method used: Column: CHIRALPAK AD-H 30×250 mm, 5 um; Method: 40% Ethanol in 0.1% diethyl amine in CO$_2$ (flow rate: 100 mL/min), ABPR 120 bar, MBPR 40 psi. The product was peak 1. LCMS (ESI): [M+H] 364. $^1$H NMR (400 MHz, METHANOL-d4) δ 8.56 (s, 2H), 7.15 (s, 1H), 3.66 (dd, J=0.75, 14.05 Hz, 1H), 3.47-3.57 (m, 1H), 2.96-3.08 (m, 1H), 2.86-2.95 (m, 1H), 2.65 (br s, 1H), 2.28-2.52 (m, 3H), 2.20 (s, 4H), 1.79 (dt, J=3.64, 7.34 Hz, 1H), 1.52-1.72 (m, 2H), 0.96 (d, J=7.03 Hz, 3H).

Example 2-38

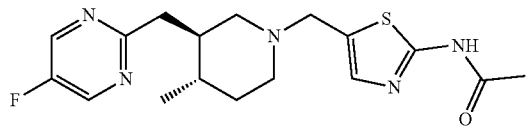 [SMILES: CC(=O)Nc1ncc(CN2CC[C@H](C)[C@@H](Cc3ncc(F)cn3)C2)s1]

N-(5-(((3R,4S)-3-((5-fluoropyrimidin-2-yl)methyl)-4-methylpiperidin-1-yl)methyl)thiazol-2-yl)acetamide The title compound was prepared in an analogous manner of that in scheme 2 from trans-tert-butyl 3-(bromomethyl)-4-methylpiperidine-1-carboxylate, 2-bromo-5-fluoropyrimidine, and N-(5-(chloromethyl)thiazol-2-yl)acetamide, followed by chiral separation; absolute configuration assigned arbitrarily. The chiral separation method used was: Column: CHIRALPAK AD-H 30×250 mm, Sum; Method: 40% Ethanol in 0.1% diethyl amine in $CO_2$ (flow rate: 100 mL/min), ABPR 120 bar, MBPR 40 psi. The product was peak 2. LCMS (ESI): [M+H] 364. $^1$H NMR (400 MHz, METHANOL-d4) δ 8.56 (s, 2H), 7.15 (s, 1H), 3.62-3.70 (m, 1H), 3.48-3.57 (m, 1H), 2.97-3.09 (m, 1H), 2.86-2.95 (m, 1H), 2.65 (br s, 1H), 2.27-2.50 (m, 3H), 2.20 (s, 4H), 1.80 (tt, J=3.89, 7.40 Hz, 1H), 1.52-1.72 (m, 2H), 0.96 (d, J=7.03 Hz, 3H).

Example 2-39

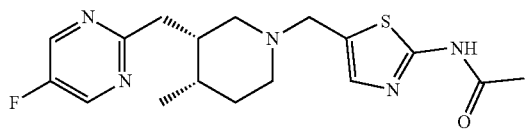 [SMILES: CC(=O)Nc1ncc(CN2CC[C@H](C)[C@H](Cc3ncc(F)cn3)C2)s1]

N-(5-(((3S,4S)-3-((5-fluoropyrimidin-2-yl)methyl)-4-methylpiperidin-1-yl)methyl)thiazol-2-yl)acetamide The title compound was prepared in an analogous manner of that in scheme 2 from cis-tert-butyl 3-(bromomethyl)-4-methylpiperidine-1-carboxylate, 2-bromo-5-fluoropyrimidine, and N-(5-(chloromethyl)thiazol-2-yl)acetamide, followed by chiral separation; absolute configuration assigned arbitrarily. The chiral separation method used: Column: CHIRALPAK AD-H 30×250 mm, Sum. Method: 40% Ethanol w/ 0.1% DEA in $C_{O2}$ (flow rate: 100 mL/min), ABPR 120 bar, MBPR 40 psi. The product was peak 1. LCMS (ESI): [M+H] 364. $^1$H NMR (400 MHz, METHANOL-d4) δ 8.56 (s, 2H), 7.15 (s, 1H), 3.62-3.73 (m, 1H), 3.53 (br d, J=14.05 Hz, 1H), 2.96-3.09 (m, 1H), 2.86-2.95 (m, 1H), 2.66 (br s, 1H), 2.28-2.54 (m, 3H), 2.20 (s, 4H), 1.74-1.87 (m, 1H), 1.50-1.73 (m, 2H), 0.96 (d, J=7.03 Hz, 3H).

Example 2-40

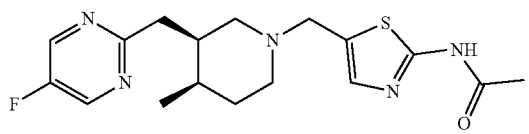 [SMILES: CC(=O)Nc1ncc(CN2CC[C@@H](C)[C@@H](Cc3ncc(F)cn3)C2)s1]

N-(5-(((3R,4R)-3-((5-fluoropyrimidin-2-yl)methyl)-4-methylpiperidin-1-yl)methyl)thiazol-2-yl)acetamide The title compound was prepared in an analogous manner of that in scheme 2 from cis-tert-butyl 3-(bromomethyl)-4-methylpiperidine-1-carboxylate, 2-bromo-5-fluoropyrimidine, and N-(5-(chloromethyl)thiazol-2-yl)acetamide, followed by chiral separation; absolute configuration assigned arbitrarily. The chiral separation method used was: Column: CHIRALPAK AD-H 30×250 mm, Sum. Method: 40% Ethanol w/ 0.1% DEA in $CO_2$ (flow rate: 100 mL/min), ABPR 120 bar, MBPR 40 psi. The product was peak 2. LCMS (ESI): [M+H] 364. $^1$H NMR (400 MHz, METHANOL-d4) δ 8.56 (s, 2H), 7.15 (s, 1H), 3.62-3.72 (m, 1H), 3.49-3.57 (m, 1H), 2.97-3.10 (m, 1H), 2.85-2.95 (m, 1H), 2.66 (br s, 1H), 2.28-2.52 (m, 3H), 2.20 (s, 4H), 1.75-1.89 (m, 1H), 1.51-1.73 (m, 2H), 0.96 (d, J=7.03 Hz, 3H).

Example 2-41

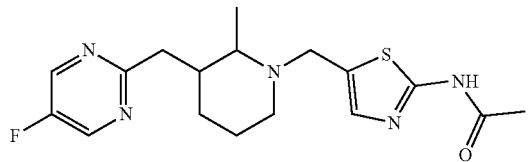 [SMILES: CC(=O)Nc1ncc(CN2CCCC(Cc3ncc(F)cn3)C2C)s1]

N-(5-((3-((5-fluoropyrimidin-2-yl)methyl)-2-methylpiperidin-1-yl)methyl)thiazol-2-yl)acetamide The title compound was prepared in an analogous manner of that in scheme 2 from tert-butyl 3-(bromomethyl)-2-methylpiperidine-1-carboxylate, 2-bromo-5-fluoropyrimidine, and N-(5-(chloromethyl)thiazol-2-yl)acetamide. LCMS (ESI): [M+H] 364. $^1$H NMR (400 MHz, $CDCl_3$) δ 11.42 (br s, 1H), 8.44-8.59 (m, 2H), 7.19 (br d, J=8.03 Hz, 1H), 3.58-3.92 (m, 2H), 2.87 (br d, J=7.28 Hz, 3H), 2.47 (br d, J=9.03 Hz, 3H), 2.30 (s, 3H), 1.15-1.46 (m, 3H), 1.15-1.46 (m, 1H), 1.03 (br s, 3H).

Example 2-42

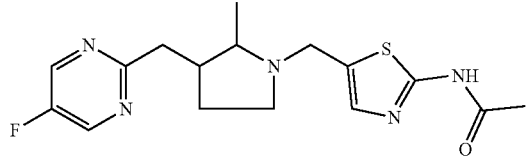 [SMILES: CC(=O)Nc1ncc(CN2CCC(Cc3ncc(F)cn3)C2C)s1]

N-(5-((3-((5-fluoropyrimidin-2-yl)methyl)-2-methylpyrrolidin-1-yl)methyl)thiazol-2-yl)acetamide The title compound was prepared in an analogous manner of that in scheme 2 from tert-butyl 3-(bromomethyl)-2-methylpyrrolidine-1-carboxylate, 2-bromo-5-fluoropyrimidine, and N-(5-(chloromethyl)thiazol-2-yl)acetamide. LCMS (ESI): [M+H] 350. $^1$H NMR (400 MHz, $CDCl_3$) δ 11.52 (br s, 1H), 8.52 (s, 2H), 7.22 (br s, 1H), 4.05 (br d, J=13.80 Hz, 1H), 3.72 (br s, 1H), 2.69-3.20 (m, 5H), 2.36-2.59 (m, 1H), 2.31 (s, 3H), 1.79 (br s, 1H), 1.59 (br s, 1H), 1.11 (br d, J=5.02 Hz, 3H).

Example 2-43

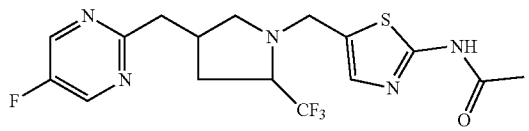 [SMILES: CC(=O)Nc1ncc(CN2CC(Cc3ncc(F)cn3)CC2C(F)(F)F)s1]

N-(5-((4-((5-fluoropyrimidin-2-yl)methyl)-2-(trifluoromethyl)pyrrolidin-1-yl)methyl)thiazol-2-yl)acetamide The title compound was prepared in an analogous manner of that in scheme 2 from, tert-butyl 4-(bromomethyl)-2-(trifluoromethyl)pyrrolidine-1-carboxylate, 2-bromo-5-fluoropyrimidine, and N-(5-(chloromethyl)thiazol-2-yl)acetamide. The resulting enantiomers were separated using chiral SFC.

Example 2-44

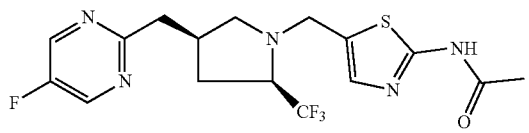

N-(5-(((2R,4S)-4-((5-fluoropyrimidin-2-yl)methyl)-2-(trifluoromethyl)pyrrolidin-1-yl)methyl)thiazol-2-yl)acetamide Relative and absolute configuration assigned arbitrarily. Column: CHIRALPAK AD-H 30×250 mm, 5um; Method: 40% Ethanol in 0.1% diethyl amine in CO$_2$ (flow rate: 100 mL/min), ABPR 120 bar, MBPR 40 psi. The product was peak 1. LCMS (ESI): [M+H] 404. $^1$H NMR (500 MHz, CDCl$_3$) δ 11.89 (br s, 1H), 8.51 (s, 2H), 7.21 (s, 1H), 3.92-4.23 (m, 2H), 3.30-3.40 (m, 1H), 3.13-3.20 (m, 1H), 2.93-3.07 (m, 2H), 2.77-2.90 (m, 1H), 2.39 (dd, J=10.07, 8.85 Hz, 1H), 2.32 (s, 3H), 2.12 (br dd, J=13.50, 6.94 Hz, 1H), 1.77 (dt, J=13.58, 10.83 Hz, 1H).

Example 2-45

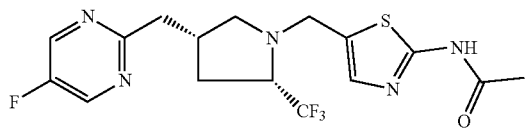 [SMILES: CC(=O)Nc1ncc(CN2C[C@@H](Cc3ncc(F)cn3)C[C@H]2C(F)(F)F)s1]

N-(5-(((2S,4R)-4-((5-fluoropyrimidin-2-yl)methyl)-2-(trifluoromethyl)pyrrolidin-1-yl)methyl)thiazol-2-yl)acetamide Relative and absolute configuration assigned arbitrarily. Column: CHIRALPAK AD-H 30×250 mm, 5 um; Method: 40% Ethanol in 0.1% diethyl amine in CO$_2$ (flow rate: 100 mL/min), ABPR 120 bar, MBPR 40 psi. The product was peak 2. LCMS (ESI): [M+H] 404. $^1$H NMR (500 MHz, CDCl$_3$) δ 11.97 (br s, 1H), 8.52 (s, 2H), 7.22 (s, 1H), 3.96-4.23 (m, 2H), 3.30-3.43 (m, 1H), 3.18 (dd, J=8.01, 6.48 Hz, 1H), 2.93-3.09 (m, 2H), 2.78-2.91 (m, 1H), 2.40 (dd, J=10.07, 8.85 Hz, 1H), 2.30-2.36 (m, 3H), 2.14 (ddd, J=13.47, 7.06, 1.30 Hz, 1H), 1.78 (dt, J=13.54, 10.78 Hz, 1H).

Example 2-46

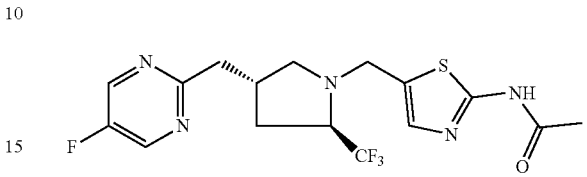

N-(5-(((2R,4R)-4-((5-fluoropyrimidin-2-yl)methyl)-2-(trifluoromethyl)pyrrolidin-1-yl)methyl)thiazol-2-yl)acetamide Relative and absolute configuration assigned arbitrarily. Column: CHIRALPAK AD-H 30×250 mm, 5um; Method: 40% Ethanol in 0.1% diethyl amine in CO$_2$ (flow rate: 100 mL/min), ABPR 120 bar, MBPR 40 psi. The product was peak 3. LCMS (ESI): [M+H] 404. $^1$H NMR (500 MHz, CDCl$_3$) δ 10.69 (br s, 1H), 8.45 (s, 2H), 7.19 (s, 5H), 3.90-4.15 (m, 2H), 3.14 (qd, J=7.43, 2.59 Hz, 1H), 2.95-3.05 (m, 1H), 2.78-2.94 (m, 3H), 2.67 (td, J=9.77, 6.10 Hz, 1H), 2.23 (s, 3H), 1.99 (ddt, J=12.57, 10.59, 7.34, 7.34 Hz, 1H), 1.48-1.61 (m, 1H).

Example 2-47

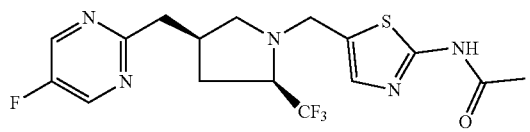 [SMILES: CC(=O)Nc1ncc(CN2C[C@H](Cc3ncc(F)cn3)C[C@@H]2C(F)(F)F)s1]

N-(5-(((2R,4S)-4-((5-fluoropyrimidin-2-yl)methyl)-2-(trifluoromethyl)pyrrolidin-1-yl)methyl)thiazol-2-yl)acetamide Relative and absolute configuration assigned arbitrarily. Column: CHIRALPAK AD-H 30×250 mm, 5um; Method: 40% Ethanol in 0.1% diethyl amine in CO$_2$ (flow rate: 100 mL/min), ABPR 120 bar, MBPR 40 psi. The product was peak 4. LCMS (ESI): [M+H] 404. $^1$H NMR (500 MHz, CDCl$_3$) δ 10.73 (br s, 1H), 8.45 (s, 2H), 7.17-7.22 (m, 5H), 3.90-4.15 (m, 2H), 3.14 (qd, J=7.43, 2.75 Hz, 1H), 2.97-3.04 (m, 1H), 2.78-2.95 (m, 3H), 2.67 (td, J=9.77, 6.10 Hz, 1H), 2.23 (s, 3H), 1.99 (ddt, J=12.59, 10.49, 7.38, 7.38 Hz, 1H), 1.57 (m, 1H).

Example 2-48

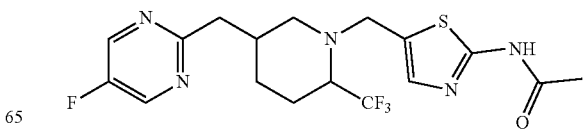

N-(5-((5-((5-fluoropyrimidin-2-yl)methyl)-2-(trifluoromethyl)piperidin-1-yl)methyl)thiazol-2-yl)acetamide The title compound was prepared in an analogous manner of that in scheme 2 from, tert-butyl 5-(bromomethyl)-2-(trifluoromethyl)piperidine-1-carboxylate, 2-bromo-5-fluoropyrimidine, and N-(5-(chloromethyl)thiazol-2-yl)acetamide. The resulting isomers were separated using: Column: CHIRALPAK AD-H 30×250 mm, 5um; Method: 30% Iso-propanol in 0.1% diethyl amine in $CO_2$ (flow rate: 100 mL/min), ABPR 120 bar, MBPR 40 psi.

Example 2-49

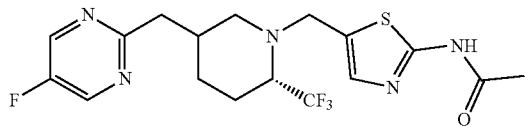 [SMILES: CC(=O)Nc1ncc(CN2CC(Cc3ncc(F)cn3)CC[C@H]2C(F)(F)F)s1]

Relative and absolute configuration assigned arbitrarily; the product was peak 1. LCMS (ESI): [M+H] 487. $^1$H NMR (500 MHz, $CDCl_3$) δ 12.15 (br s, 1H), 8.52 (s, 2H), 7.22 (s, 1H), 3.93-4.18 (m, 2H), 3.27-3.40 (m, 1H), 2.80-2.91 (m, 2H), 2.74-2.80 (m, 1H), 2.64-2.74 (m, 1H), 2.31-2.36 (m, 3H), 2.20-2.31 (m, 1H), 1.94-2.03 (m, 1H), 1.77-1.89 (m, 1H), 1.62 (br d, J=12.21 Hz, 1H), 1.36-1.49 (m, 1H).

Example 2-50

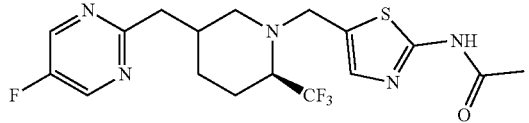 [SMILES: CC(=O)Nc1ncc(CN2CC(Cc3ncc(F)cn3)CC[C@@H]2C(F)(F)F)s1]

Relative and absolute configuration assigned arbitrarily; the product was peak 2. LCMS (ESI): [M+H] 487. $^1$H NMR (500 MHz, $CDCl_3$) δ 12.15 (br s, 1H), 8.52 (s, 2H), 7.22 (s, 1H), 3.96-4.15 (m, 2H), 3.25-3.39 (m, 1H), 2.80-2.90 (m, 2H), 2.74-2.80 (m, 1H), 2.65-2.73 (m, 1H), 2.30-2.35 (m, 3H), 2.21-2.29 (m, 1H), 1.94-2.02 (m, 1H), 1.78-1.89 (m, 1H), 1.62 (br d, J=12.21 Hz, 1H), 1.37-1.49 (m, 1H).

Example 2-51

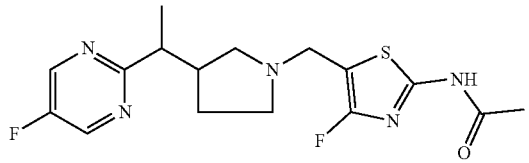 [SMILES: CC(=O)Nc1nc(F)c(CN2CCC(C(C)c3ncc(F)cn3)C2)s1]

N-(4-fluoro-5-((3-(1-(5-fluoropyrimidin-2-yl)ethyl) pyrrolidin-1-yl)methyl)thiazol-2-yl)acetamide The title compound was prepared in an analogous manner of that in example 1-1 from 5-fluoro-2-(1-(pyrrolidin-3-yl) ethyl)pyrimidine and N-(4-fluoro-5-formylthiazol-2-yl)acetamide. LCMS (ESI): [M+H] 368. $^1$H NMR (400 MHz, Methanol-$d_4$) δ 8.66 (dd, J=0.88, 1.63 Hz, 2H), 3.82-3.96 (m, 2H), 3.00-3.21 (m, 2H), 2.81-2.96 (m, 1H), 2.67-2.80 (m, 2H), 2.40-2.66 (m, 1H), 2.19 (d, J=4.77 Hz, 3H), 1.72-1.83 (m, 1H), 1.34-1.57 (m, 1H), 1.30 (dd, J=7.03, 11.29 Hz, 3H).

Example 2-52

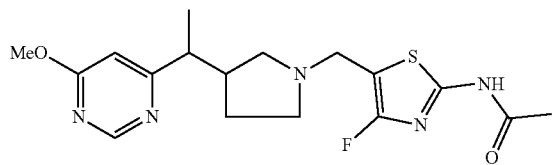 [SMILES: COc1cc(C(C)C2CCN(Cc3sc(NC(C)=O)nc3F)C2)ncn1]

N-(4-fluoro-5-((3-(1-(6-methoxypyrimidin-4-yl) ethyl)pyrrolidin-1-yl)methyl)thiazol-2-yl)acetamide The title compound was prepared in an analogous manner of that in scheme 2 from 4-methoxy-6-(1-(pyrrolidin-3-yl) ethyl)pyrimidine and N-(4-fluoro-5-formylthiazol-2-yl)acetamide. LCMS (ESI): [M+H] 380. $^1$H NMR (400 MHz, Methanol-$d_4$) δ 8.69 (s, 1H), 6.75-6.85 (m, 1H), 4.38-4.66 (m, 2H), 3.99 (d, J=0.75 Hz, 1H), 3.96-4.06 (m, 1H), 3.96-4.06 (m, 1H), 3.39-3.92 (m, 2H), 3.13 (td, J=1.63, 3.26 Hz, 1H), 2.84 (br d, J=7.53 Hz, 2H), 2.28-2.55 (m, 1H), 2.18-2.25 (m, 3H), 1.43-2.09 (m, 2H), 1.30 (dd, J=6.65, 9.91 Hz, 3H).

Example 2-53

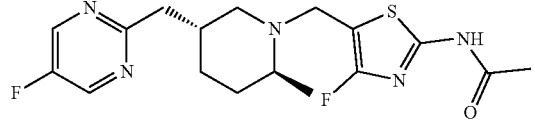 [SMILES: CC(=O)Nc1nc(F)c(CN2C[C@@H](Cc3ncc(F)cn3)CC[C@@H]2C)s1]

N-(4-fluoro-5-(((2S,5R)-5-((5-fluoropyrimidin-2-yl) methyl)-2-methylpiperidin-1-yl)methyl)thiazol-2-yl) acetamide The title compound was prepared according to the general procedure described in scheme 2 and using 5-fluoro-2-(((3R,6S)-6-methylpiperidin-3-yl)methyl)pyrimidine and N-(4-fluoro-5-formylthiazol-2-yl)acetamide. LCMS (ESI): [M+H] 382. $^1$HNMR: (400 MHz, Methanol-$d_4$) δ 8.66 (d, J=1.00 Hz, 2H), 3.72-3.96 (m, 2H), 2.71-2.92 (m, 3H), 2.13-2.38 (m, 2H), 2.22 (s, 3H), 1.92-2.07 (m, 1H), 1.63-1.77 (m, 2H), 1.28-1.47 (m, 1H), 1.22 (d, J=6.27 Hz, 3H), 1.00-1.16 (m, 1H).

Scheme 3

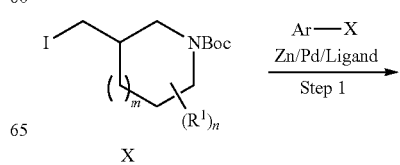

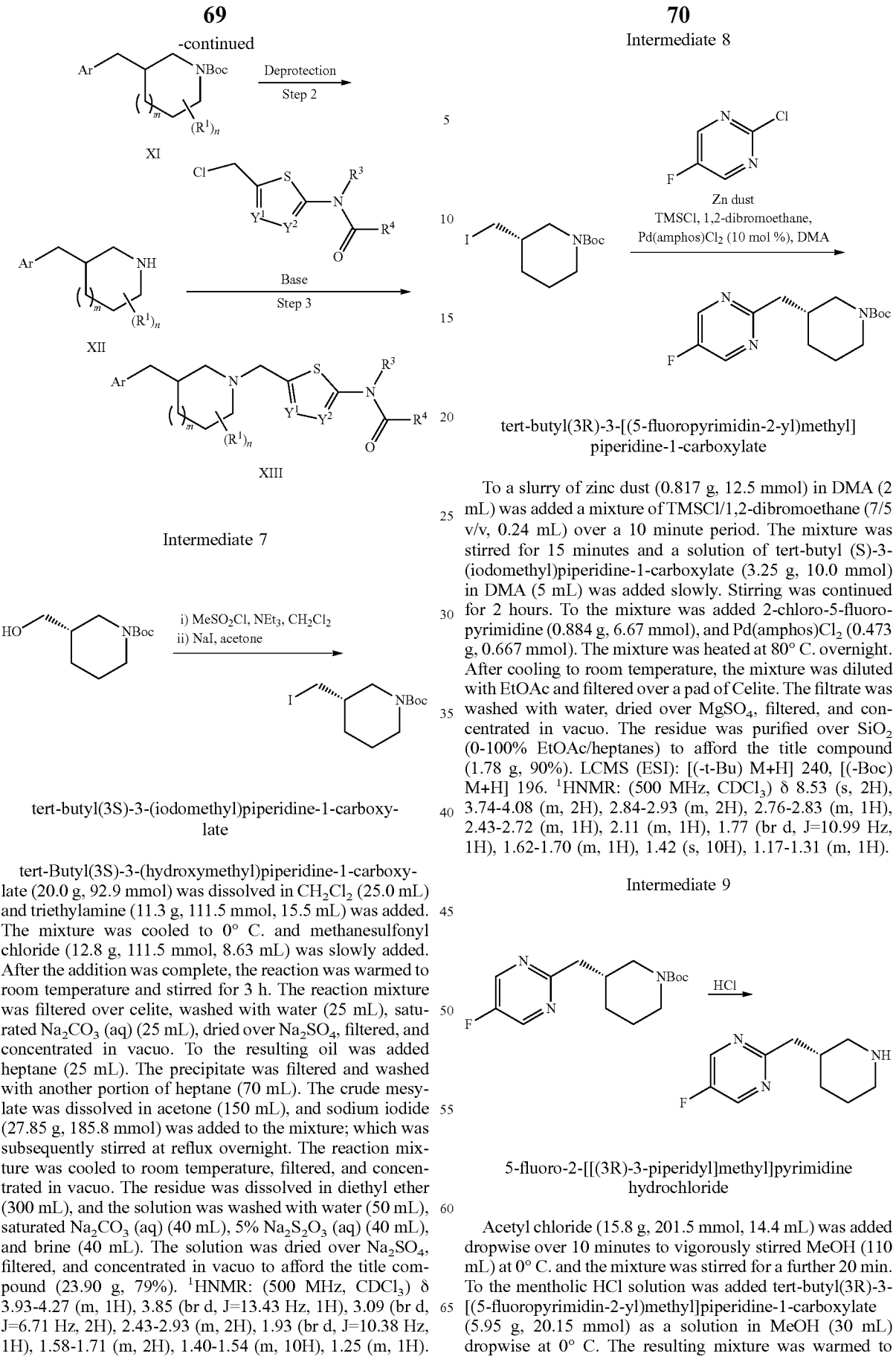

Intermediate 7 tert-butyl(3S)-3-(iodomethyl)piperidine-1-carboxylate tert-Butyl(3S)-3-(hydroxymethyl)piperidine-1-carboxylate (20.0 g, 92.9 mmol) was dissolved in $CH_2Cl_2$ (25.0 mL) and triethylamine (11.3 g, 111.5 mmol, 15.5 mL) was added. The mixture was cooled to 0° C. and methanesulfonyl chloride (12.8 g, 111.5 mmol, 8.63 mL) was slowly added. After the addition was complete, the reaction was warmed to room temperature and stirred for 3 h. The reaction mixture was filtered over celite, washed with water (25 mL), saturated $Na_2CO_3$ (aq) (25 mL), dried over $Na_2SO_4$, filtered, and concentrated in vacuo. To the resulting oil was added heptane (25 mL). The precipitate was filtered and washed with another portion of heptane (70 mL). The crude mesylate was dissolved in acetone (150 mL), and sodium iodide (27.85 g, 185.8 mmol) was added to the mixture; which was subsequently stirred at reflux overnight. The reaction mixture was cooled to room temperature, filtered, and concentrated in vacuo. The residue was dissolved in diethyl ether (300 mL), and the solution was washed with water (50 mL), saturated $Na_2CO_3$ (aq) (40 mL), 5% $Na_2S_2O_3$ (aq) (40 mL), and brine (40 mL). The solution was dried over $Na_2SO_4$, filtered, and concentrated in vacuo to afford the title compound (23.90 g, 79%). $^1$HNMR: (500 MHz, $CDCl_3$) δ 3.93-4.27 (m, 1H), 3.85 (br d, J=13.43 Hz, 1H), 3.09 (br d, J=6.71 Hz, 2H), 2.43-2.93 (m, 2H), 1.93 (br d, J=10.38 Hz, 1H), 1.58-1.71 (m, 2H), 1.40-1.54 (m, 10H), 1.25 (m, 1H).

Intermediate 8 tert-butyl(3R)-3-[(5-fluoropyrimidin-2-yl)methyl]piperidine-1-carboxylate

To a slurry of zinc dust (0.817 g, 12.5 mmol) in DMA (2 mL) was added a mixture of TMSCl/1,2-dibromoethane (7/5 v/v, 0.24 mL) over a 10 minute period. The mixture was stirred for 15 minutes and a solution of tert-butyl (S)-3-(iodomethyl)piperidine-1-carboxylate (3.25 g, 10.0 mmol) in DMA (5 mL) was added slowly. Stirring was continued for 2 hours. To the mixture was added 2-chloro-5-fluoropyrimidine (0.884 g, 6.67 mmol), and Pd(amphos)Cl$_2$ (0.473 g, 0.667 mmol). The mixture was heated at 80° C. overnight. After cooling to room temperature, the mixture was diluted with EtOAc and filtered over a pad of Celite. The filtrate was washed with water, dried over $MgSO_4$, filtered, and concentrated in vacuo. The residue was purified over $SiO_2$ (0-100% EtOAc/heptanes) to afford the title compound (1.78 g, 90%). LCMS (ESI): [(-t-Bu) M+H] 240, [(-Boc) M+H] 196. $^1$HNMR: (500 MHz, $CDCl_3$) δ 8.53 (s, 2H), 3.74-4.08 (m, 2H), 2.84-2.93 (m, 2H), 2.76-2.83 (m, 1H), 2.43-2.72 (m, 1H), 2.11 (m, 1H), 1.77 (br d, J=10.99 Hz, 1H), 1.62-1.70 (m, 1H), 1.42 (s, 10H), 1.17-1.31 (m, 1H).

Intermediate 9

5-fluoro-2-[[(3R)-3-piperidyl]methyl]pyrimidine hydrochloride

Acetyl chloride (15.8 g, 201.5 mmol, 14.4 mL) was added dropwise over 10 minutes to vigorously stirred MeOH (110 mL) at 0° C. and the mixture was stirred for a further 20 min. To the mentholic HCl solution was added tert-butyl(3R)-3-[(5-fluoropyrimidin-2-yl)methyl]piperidine-1-carboxylate (5.95 g, 20.15 mmol) as a solution in MeOH (30 mL) dropwise at 0° C. The resulting mixture was warmed to room temperature and stirred for a further 2 hours. The mixture was concentrated in vacuo to afford the title compound (4.60 g, 98%). LCMS (ESI): [M+H] 232. ¹HNMR: (400 MHz, Methanol-d4) δ 8.67-8.76 (m, 2H), 3.27-3.38 (m, 2H), 2.82-2.97 (m, 3H), 2.70-2.81 (m, 1H), 2.34-2.46 (m, 1H), 1.78-1.93 (m, 2H), 1.72 (s, 1H), 1.26-1.39 (m, 1H).

Example 3-1

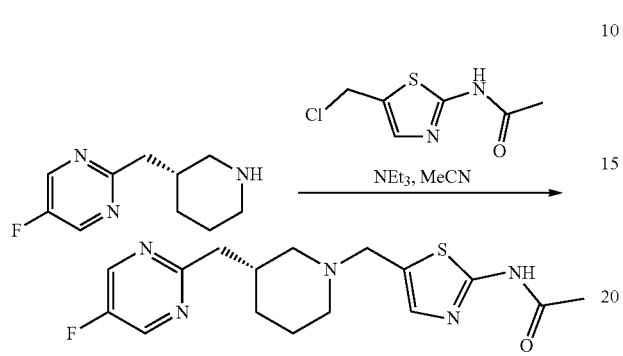

N-[5-[[(3R)-3-[(5-fluoropyrimidin-2-yl)methyl]-1-piperidyl]methyl]thiazol-2-yl]acetamide To a suspension of 5-fluoro-2-[[(3R)-3-piperidyl]methyl] pyrimidine hydrochloride (7.90 g, 34.1 mmol) and N-[5-(chloromethyl)thiazol-2-yl]acetamide (6.83 g, 35.8 mmol) in MeCN (170 mL) was added triethylamine (10.35 g, 102 mmol, 14.2 mL); which was subsequently warmed to 70° C. overnight. The reaction was cooled to room temperature, and the mixture was diluted with EtOAc and washed with saturated NH₄Cl(aq). The organics were dried over MgSO₄, filtered and concentrated in vacuo. The residue was purified over SiO₂ (24 g, 0-100% EtOAc:iPrOH (3:1 v/v)-heptane) to afford the title compound (8.24 g, 69%). LCMS (ESI): [M+H] 350. ¹HNMR: (500 MHz, CDCl₃) δ 11.89 (br s, 1H), 8.52 (s, 2H), 7.18 (s, 1H), 3.65 (q, J=13.63 Hz, 2H), 2.86 (d, J=7.33 Hz, 2H), 2.77-2.84 (m, 2H), 2.31 (s, 3H), 2.18-2.28 (m, 1H), 1.98-2.07 (m, 1H), 1.90 (br t, J=10.38 Hz, 1H), 1.66-1.71 (m, 2H), 1.51-1.61 (m, 1H), 1.00-1.09 (m, 1H).

Example 3-2

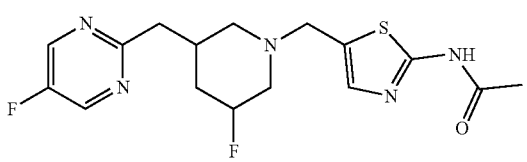 [SMILES: CC(=O)Nc1ncc(CN2CC(F)CC(Cc3ncc(F)cn3)C2)s1]

N-(5-((3-fluoro-5-((5-fluoropyrimidin-2-yl)methyl) piperidin-1-yl)methyl)thiazol-2-yl)acetamide The title compound was prepared in an analogous manner of that in scheme 3 from tert-butyl 3-fluoro-5-(iodomethyl) piperidine-1-carboxylate, 2-chloro-5-fluoro-pyrimidine, and N-[5-(chloromethyl)thiazol-2-yl]acetamide. LCMS (ESI): [M+H] 368. ¹HNMR: (500 MHz, CDCl₃) δ 11.96 (br s, 1H), 8.54 (s, 2H), 7.21 (s, 1H), 4.66 (tt, J=9.99, 4.73 Hz, 0.5H), 4.56 (tt, J=9.96, 4.77 Hz, 0.5H), 3.68-3.82 (m, 2H), 3.18 (dt, J=9.99, 4.92 Hz, 1H), 2.88-3.00 (m, 3H), 2.85 (br d, J=10.53 Hz, 1H), 2.34-2.40 (m, 1H), 2.28-2.34 (m, 4H), 2.12-2.20 (m, 1H), 2.05 (td, J=9.84, 5.04 Hz, 1H), 1.90 (t, J=10.68 Hz, 1H), 1.25 (quin, J=11.48 Hz, 1H).

Example 3-3

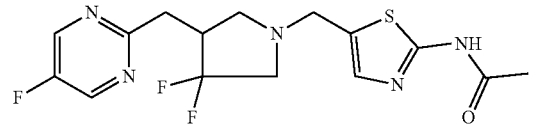 [SMILES: CC(=O)Nc1ncc(CN2CC(Cc3ncc(F)cn3)C(F)(F)C2)s1]

N-(5-((3,3-difluoro-4-((5-fluoropyrimidin-2-yl) methyl)pyrrolidin-1-yl)methyl)thiazol-2-yl)acetamide The title compound was prepared in an analogous manner of that in scheme 3 from tert-butyl 3,3-difluoro-4-(iodomethyl)pyrrolidine-1-carboxylate, 2-chloro-5-fluoro-pyrimidine, and N-[5-(chloromethyl)thiazol-2-yl]acetamide. LCMS: [M+H] 372. ¹HNMR: (500 MHz, CDCl₃) δ 12.17 (br s, 1H), 8.54 (s, 2H), 7.23 (t, J=0.84 Hz, 1H), 3.82 (t, J=0.92 Hz, 2H), 3.34-3.40 (m, 1H), 3.23-3.33 (m, 1H), 3.14 (td, J=6.41, 3.36 Hz, 2H), 3.04 (dd, J=15.03, 9.54 Hz, 1H), 2.81-2.91 (m, 1H), 2.44-2.50 (m, 1H), 2.30-2.36 (m, 3H).

Example 3-4

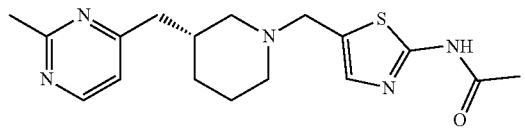 [SMILES: CC(=O)Nc1ncc(CN2CCC[C@H](Cc3ccnc(C)n3)C2)s1]

(R)-N-(5-((3-((2-methylpyrimidin-4-yl)methyl)piperidin-1-yl)methyl)thiazol-2-yl)acetamide The title compound was prepared in an analogous manner of that in scheme 3 from tert-butyl (S)-3-(iodomethyl) piperidine-1-carboxylate, 4-chloro-2-methyl-pyrimidine, and N-[5-(chloromethyl)thiazol-2-yl]acetamide. LCMS: [M+H] 346. ¹HNMR: (400 MHz, CDCl₃) δ 11.56 (br s, 1H), 8.48 (d, J=5.02 Hz, 1H), 7.17 (s, 1H), 6.94 (d, J=5.27 Hz, 1H), 3.57-3.71 (m, 2H), 2.76 (m, 2H), 2.70 (s, 3H), 2.57-2.68 (m, 2H), 2.31 (s, 3H), 2.06-2.18 (m, 2H), 1.89 (m, 1H), 1.67 (m, 2H), 1.50-1.63 (m, 1H), 0.99-1.11 (m, 1H).

Example 3-5

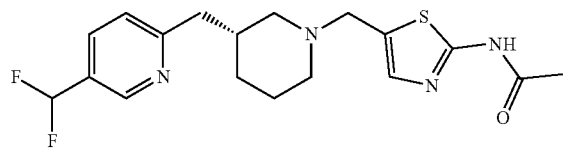 [SMILES: CC(=O)Nc1ncc(CN2CCC[C@H](Cc3ccc(C(F)F)cn3)C2)s1]

(R)-N-(5-((3-((5-(difluoromethyl)pyridin-2-yl)methyl)piperidin-1-yl)methyl)thiazol-2-yl)acetamide The title compound was prepared in an analogous manner of that in scheme 3 from tert-butyl (S)-3-(iodomethyl)piperidine-1-carboxylate, 2-chloro-5-(difluoromethyl)pyridine, and N-[5-(chloromethyl)thiazol-2-yl]acetamide. LCMS (ESI): [M+H] 381. ¹HNMR: (400 MHz, CDCl₃) δ 11.97 (br s, 1H), 8.64 (d, J=1.25 Hz, 1H), 7.74 (d, J=7.76 Hz, 1H), 7.23 (d, J=8.03 Hz, 1H), 7.17 (s, 1H), 6.68 (t, J=56.47 Hz, 1H), 3.57-3.72 (m, 2H), 2.70-2.85 (m, 4H), 2.31 (s, 3H), 2.03-2.19 (m, 2H), 1.90 (br t, J=10.29 Hz, 1H), 1.67 (m, 2H), 1.48-1.60 (m, 1H), 0.99-1.13 (m, 1H).

Example 3-6

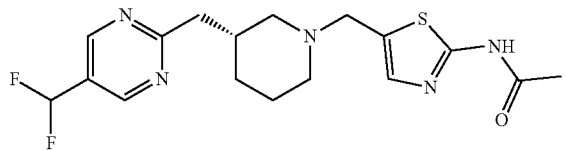 [SMILES: CC(=O)Nc1ncc(CN2CCC[C@H](Cc3ncc(C(F)F)cn3)C2)s1]

(R)-N-(5-((3-((5-(difluoromethyl)pyrimidin-2-yl)methyl)piperidin-1-yl)methyl)thiazol-2-yl)acetamide The title compound was prepared in an analogous manner of that in scheme 3 from tert-butyl (S)-3-(iodomethyl)piperidine-1-carboxylate, 2-chloro-5-(difluoromethyl)pyrimidine, and N-[5-(chloromethyl)thiazol-2-yl]acetamide. LCMS (ESI): [M+H] 382. ¹HNMR: (400 MHz, CDCl₃) δ 11.69 (br s, 1H), 8.80 (s, 2H), 7.18 (s, 1H), 6.73 (t, J=55.22 Hz, 1H), 3.59-3.71 (m, 2H), 2.93 (d, J=7.28 Hz, 2H), 2.81 (br t, J=9.91 Hz, 2H), 2.30 (s, 3H), 2.01-2.11 (m, 1H), 1.93 (t, J=10.29 Hz, 1H), 1.52-1.74 (m, 4H), 1.02-1.14 (m, 1H).

Example 3-7

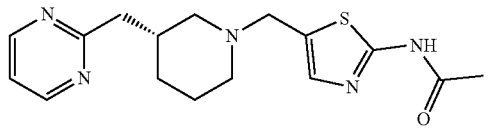 [SMILES: CC(=O)Nc1ncc(CN2CCC[C@H](Cc3ncccn3)C2)s1]

(R)-N-(5-((3-(pyrimidin-2-ylmethyl)piperidin-1-yl)methyl)thiazol-2-yl)acetamide

The title compound was prepared in an analogous manner of that in scheme 3 from tert-butyl (S)-3-(iodomethyl)piperidine-1-carboxylate, 2-chloropyrimidine, and N-[5-(chloromethyl)thiazol-2-yl]acetamide. LCMS (ESI): [M+H] 331. ¹HNMR: (400 MHz, CDCl₃) δ 11.39 (br s, 1H), 8.67 (d, J=5.02 Hz, 2H), 7.18 (s, 1H), 7.12 (t, J=4.89 Hz, 1H), 3.59-3.70 (m, 2H), 2.79-2.91 (m, 4H), 2.30 (s, 3H), 1.97-2.04 (m, 1H), 1.91 (t, J=10.42 Hz, 1H), 1.63-1.74 (m, 3H), 1.52-1.62 (m, 1H), 1.00-1.11 (m, 1H).

Example 3-8

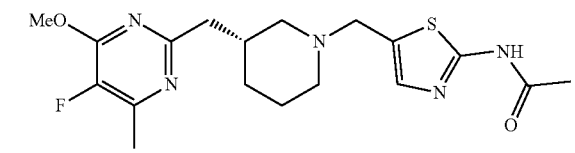 [SMILES: COc1nc(C[C@H]2CCCN(Cc3cnc(NC(C)=O)s3)C2)nc(C)c1F]

(R)-N-(5-((3-((5-fluoro-4-methoxy-6-methylpyrimidin-2-yl)methyl)piperidin-1-yl)methyl)thiazol-2-yl)acetamide The title compound was prepared in an analogous manner of that in scheme 3 from tert-butyl (S)-3-(iodomethyl)piperidine-1-carboxylate, 2-bromo-5-fluoro-4-methoxy-6-methylpyrimidine, and N-(5-(chloromethyl)thiazol-2-yl)acetamide. LCMS (ESI): [M+H] 394. ¹H NMR (500 MHz, CDCl₃) δ 11.74 (br s, 1H), 7.18 (s, 1H), 4.00 (s, 3H), 3.65 (s, 2H), 2.80-2.91 (m, 2H), 2.66 (d, J=7.33 Hz, 2H), 2.40 (d, J=2.44 Hz, 3H), 2.31 (s, 3H), 2.17-2.27 (m, 1H), 2.01 (br t, J=10.38 Hz, 1H), 1.85 (br t, J=10.38 Hz, 1H), 1.53-1.73 (m, 3H), 0.97-1.07 (m, 1H).

Example 3-9

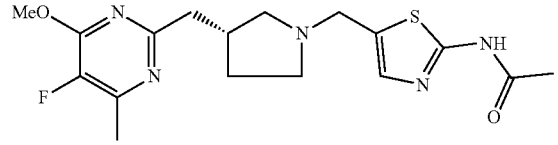 [SMILES: COc1nc(C[C@H]2CCN(Cc3cnc(NC(C)=O)s3)C2)nc(C)c1F]

(R)-N-(5-((3-((5-fluoro-4-methoxy-6-methylpyrimidin-2-yl)methyl)pyrrolidin-1-yl)methyl)thiazol-2-yl)acetamide The title compound was prepared in an analogous manner of that in scheme 3 from tert-butyl (S)-3-(iodomethyl)pyrrolidine-1-carboxylate, 2-bromo-5-fluoro-4-methoxy-6-methylpyrimidine, and N-(5-(chloromethyl)thiazol-2-yl)acetamide. LCMS (ESI): [M+H] 380. ¹HNMR: (500 MHz, CDCl₃) δ 12.28 (br s, 1H), 7.22 (s, 1H), 4.00 (s, 3H), 3.73-3.85 (m, 2H), 2.82-2.92 (m, 3H), 2.68-2.81 (m, 2H), 2.52-2.62 (m, 1H), 2.40 (d, J=2.90 Hz, 3H), 2.31 (m, 4H), 1.99-2.09 (m, 1H), 1.58 (ddt, J=12.61, 8.14, 6.18, 6.18 Hz, 1H).

Example 3-10

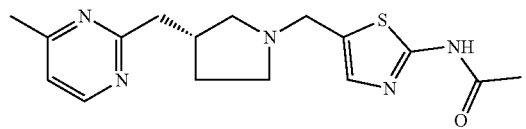 [SMILES: CC(=O)Nc1ncc(CN2CC[C@H](Cc3nccc(C)n3)C2)s1]

(R)-N-(5-((3-((4-methylpyrimidin-2-yl)methyl)pyrrolidin-1-yl)methyl)thiazol-2-yl)acetamide The title compound was prepared in an analogous manner of that in scheme 3 from tert-butyl (S)-3-(iodomethyl)

pyrrolidine-1-carboxylate, 2-bromo-4-methylpyrimidine, and N-(5-(chloromethyl)thiazol-2-yl)acetamide. LCMS (ESI): [M+H] 332. ¹HNMR (600 MHz, CDCl₃) δ 12.18 (br s, 1H), 8.48 (d, J=5.13 Hz, 1H), 7.27-7.32 (m, 1H), 6.98 (d, J=5.14 Hz, 1H), 3.84 (br s, 2H), 2.93-3.04 (m, 3H), 2.83 (dt, J=14.95, 7.38 Hz, 2H), 2.66 (br s, 1H), 2.49 (s, 3H), 2.36-2.47 (m, 1H), 2.31 (s, 3H), 2.05 (br dd, J=12.29, 5.87 Hz, 1H), 1.64 (br dd, J=12.29, 6.24 Hz, 1H).

Example 3-11

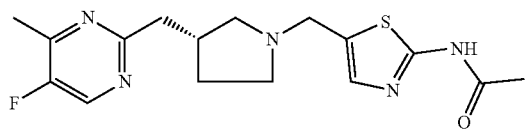 [SMILES: CC(=O)Nc1ncc(CN2CC[C@H](Cc3ncc(F)c(C)n3)C2)s1]

(R)-N-(5-((3-((5-fluoro-4-methylpyrimidin-2-yl)methyl)pyrrolidin-1-yl)methyl)thiazol-2-yl)acetamide The title compound was prepared in an analogous manner of that in scheme 3 from tert-butyl (S)-3-(iodomethyl)pyrrolidine-1-carboxylate, 2-bromo-5-fluoro-4-methylpyrimidine, and N-(5-(chloromethyl)thiazol-2-yl)acetamide. LCMS (ESI): [M+H]350. ¹H NMR (500 MHz, CDCl₃) δ 11.91 (br s, 1H), 8.35 (d, J=1.68 Hz, 1H), 7.22 (t, J=1.07 Hz, 1H), 3.78 (d, J=0.61 Hz, 2H), 2.98 (dt, J=7.25, 1.26 Hz, 2H), 2.83-2.87 (m, 1H), 2.70-2.82 (m, 2H), 2.58 (td, J=8.66, 6.03 Hz, 1H), 2.51 (d, J=2.44 Hz, 3H), 2.29-2.35 (m, 4H), 1.98-2.07 (m, 1H), 1.60 (ddt, J=12.51, 8.32, 6.14, 6.14 Hz, 1H).

Example 3-12

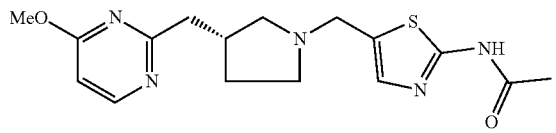 [SMILES: COc1ccnc(C[C@H]2CCN(Cc3cnc(NC(C)=O)s3)C2)n1]

(R)-N-(5-((3-((4-methoxypyrimidin-2-yl)methyl)pyrrolidin-1-yl)methyl)thiazol-2-yl)acetamide The title compound was prepared in an analogous manner of that in scheme 3 from tert-butyl (S)-3-(iodomethyl)pyrrolidine-1-carboxylate, 2-bromo-4-methoxypyrimidine, and N-(5-(chloromethyl)thiazol-2-yl)acetamide. LCMS (ESI): [M+H] 348. ¹H NMR (500 MHz, CDCl₃) δ 12.17 (br s, 1H), 8.24 (d, J=5.80 Hz, 1H), 7.13 (t, J=1.07 Hz, 1H), 6.41-6.48 (m, 1H), 3.83-3.92 (m, 3H), 3.65-3.76 (m, 2H), 2.78-2.88 (m, 3H), 2.70-2.78 (m, 1H), 2.65 (td, J=8.39, 5.80 Hz, 1H), 2.50 (td, J=8.66, 6.18 Hz, 1H), 2.24-2.29 (m, 1H), 2.23 (s, 3H), 1.91-2.03 (m, 1H), 1.53 (ddt, J=12.59, 8.28, 6.05, 6.05 Hz, 1H).

Example 3-13

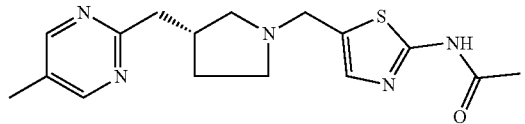 [SMILES: CC(=O)Nc1ncc(CN2CC[C@H](Cc3ncc(C)cn3)C2)s1]

(R)-N-(5-((3-((5-methylpyrimidin-2-yl)methyl)pyrrolidin-1-yl)methyl)thiazol-2-yl)acetamide The title compound was prepared in an analogous manner of that in scheme 3 from tert-butyl (S)-3-(iodomethyl)pyrrolidine-1-carboxylate, 2-bromo-5-methylpyrimidine, and N-(5-(chloromethyl)thiazol-2-yl)acetamide. LCMS (ESI): [M+H] 332. ¹H NMR (500 MHz, CDCl₃) δ 11.95 (br s, 1H), 8.48 (s, 2H), 7.20 (s, 1H), 2.94-3.03 (m, 2H), 2.75-2.87 (m, 2H), 2.72 (td, J=8.32, 5.80 Hz, 1H), 2.57 (td, J=8.54, 6.26 Hz, 1H), 2.30 (s, 4H), 2.28 (s, 3H), 1.95-2.07 (m, 1H), 1.94-2.05 (m, 1H), 1.54-1.65 (m, 1H).

Example 3-14

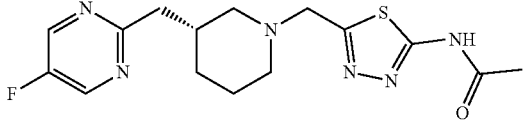 [SMILES: CC(=O)Nc1nnc(CN2CCC[C@H](Cc3ncc(F)cn3)C2)s1]

N-(5-((3-((5-fluoropyrimidin-2-yl)methyl)piperidin-1-yl)methyl)-1,3,4-thiadiazol-2-yl)acetamide The title compound was prepared according to the general procedure described in scheme 3 using 5-fluoro-2-(piperidin-3-ylmethyl)pyrimidine HCl and N-(5-formyl-1,3,4-thiadiazol-2-yl)acetamide. LCMS: [M+H] 351. ¹H NMR (400 MHz, METHANOL-d4) δ 8.63 (d, J=0.75 Hz, 2H), 3.75-3.90 (m, 2H), 2.87 (d, J=7.28 Hz, 2H), 2.74-2.83 (m, 2H), 2.13-2.35 (m, 5H), 2.01 (t, J=10.42 Hz, 1H), 1.50-1.80 (m, 3H), 0.99-1.19 (m, 1H).

Intermediate 10

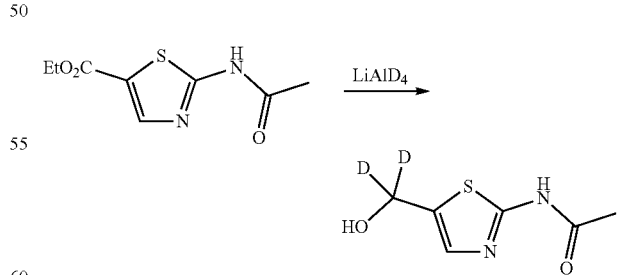

N-(5-(hydroxymethyl-d2)thiazol-2-yl)acetamide

To a suspension of ethyl 2-acetamidothiazole-5-carboxylate (214 mg, 1.00 mmol) in THF (5 mL) was added LiAD₄ (250 mg, 5.96 mmol) in THF (3 mL) at 0° C. The reaction mixture was stirred and slowly warmed to rt over. Ice was added to the mixture, followed by 1N aqueous HCl. The mixture was extracted with EtOAc (×5, add solid NaCl to saturate the aqueous layer). The combined organic phases were dried over MgSO₄, filtered and concentrated. The residue was purified by normal phase column eluted with EtOAc to get the title compound (6.5 mg, 3.7%) as a white solid. LCMS: [M+H] 175. ¹H NMR (400 MHz, METHANOL-d₄) δ 7.30 (s, 1H), 2.22 (s, 3H).

Intermediate 11

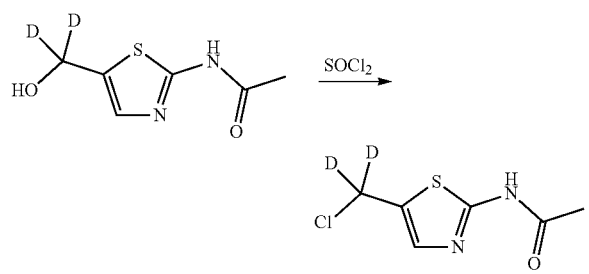

N-(5-(chloromethyl-d2)thiazol-2-yl)acetamide

To a solution of N-(5-(hydroxymethyl-d2)thiazol-2-yl) acetamide (6.50 mg, 37.31 umol) in DCM (1.00 mL) was added thionyl chloride (0.15 mL, 2.06 mmol). The mixture was stirred at 50° C. for 10 min. The reaction mixture was concentrated to provide the title compound (7.2 mg, 100%).

Example 3-15

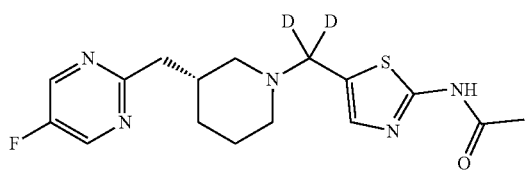 [SMILES: [2H]C([2H])(c1cnc(NC(C)=O)s1)N1CCC[C@H](Cc2ncc(F)cn2)C1]

N-(5-((3-((5-fluoropyrimidin-2-yl)methyl)piperidin-1-yl)methyl)-1,3,4-thiadiazol-2-yl)acetamide The title compound was prepared in an analogous manner of that in scheme 3 from 5-fluoro-2-(piperidin-3-ylmethyl) pyrimidine HCl and N-(5-(chloromethyl-d2)thiazol-2-yl)acetamide. LCMS: [M+H] 352. ¹H NMR (500 MHz, METHANOL-d4) δ 8.63 (s, 2H), 7.21 (s, 1H), 2.76-2.89 (m, 4H), 2.15-2.29 (m, 4H), 2.03-2.13 (m, 1H), 1.83-1.92 (m, 1H), 1.65-1.76 (m, 2H), 1.51-1.64 (m, 1H), 1.01-1.15 (m, 1H).

Intermediate 12

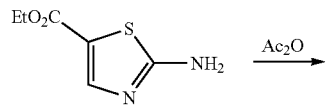

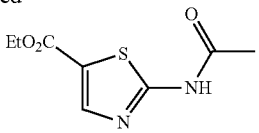

Ethyl 2-acetamidothiazole-5-carboxylate

To a stirred solution of ethyl 2-aminothiazole-5-carboxylate (10.00 g, 58.1 mmol), pyridine (9.47 mL, 117.3 mmol) and 4-dimethylaminopyridine (200.0 mg, 1.64 mmol) in dichloromethane (100. mL), was added acetic anhydride (8.23 mL, 87.1 mmol) at 0° C. The reaction was heated to reflux for 2 hours. The reaction mixture was concentrated under reduced pressure and then hydrochloric acid solution (1.5 N in water, 50 mL) was added. The mixture was stirred for 10 min. The resulting precipitate was filtered and washed with water (250 mL) and heptanes (50 mL) and then dried under high vacuum to give the title compound (11.82 g, 95.0% yield). LCMS: [M+H] 215.0. ¹H NMR: (400 MHz, DMSO-d6) δ 12.55 (s, 1H), 8.12 (s, 1H), 4.27 (q, J=7.11 Hz, 2H), 2.19 (s, 3H), 1.28 (t, J=7.15 Hz, 3H).

Intermediate 13

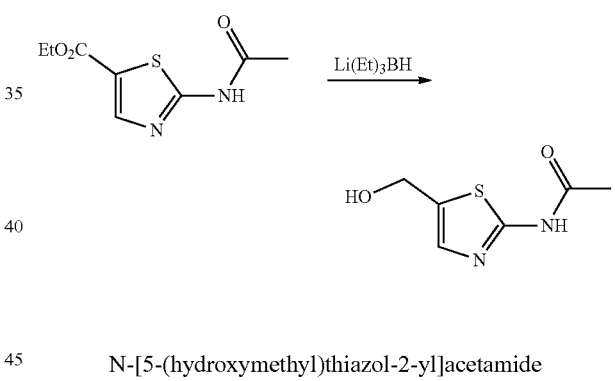

N-[5-(hydroxymethyl)thiazol-2-yl]acetamide

To a stirred solution of ethyl 2-acetamidothiazole-5-carboxylate (1.00 g, 4.67 mmol) in toluene (24 mL) was added lithium triethylborohydride (1 M in tetrahydrofuran, 9.39 mL, 9.39 mmol) slowly at 0° C. The reaction mixture was stirred at room temperature for 2.5 hours. The reaction was cooled to 0° C. and additional lithium triethylborohydride (1 M in tetrahydrofuran, 9.39 mL, 9.39 mmol) was added slowly. The reaction was stirred 2 hours at room temperature, then cooled to 0° C. Methanol (2 mL) was added very slowly added producing vigorous gas evolution. 5% citric acid solution was added and the mixture was stirred for 10 minutes at room temperature. The mixture was extracted with ethyl acetate, washed with saturated aqueous sodium chloride, dried over magnesium sulfate, filtered and evaporated. Purification was by silica gel chromatography using 0-10% methanol in dichloromethane as eluent to give the title compound (319.7 mg, 39.8% yield). LCMS: [M+H] 172.9. ¹H NMR: (400 MHz, DMSO-d6) δ 11.93 (s, 1H), 7.25 (s, 1H), 5.33 (t, J=5.65 Hz, 1H), 4.57 (dd, J=0.88, 5.65 Hz, 2H), 2.12 (s, 3H).

Intermediate 14

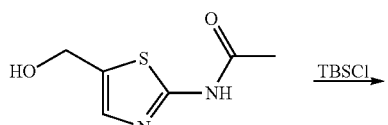

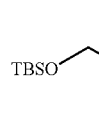

N-[5-[[tert-butyl(dimethyl)silyl]oxymethyl]thiazol-2-yl]acetamide

To a stirred mixture of N-[5-(hydroxymethyl)thiazol-2-yl]acetamide (319.7 mg, 1.86 mmol), 4-dimethylaminopyridine (22.7 mg, 186 umol), and triethylamine (515 uL, 3.71 mmol) in dichloromethane (9.45 mL) at 0° C. was added tert-butyl-chloro-dimethyl-silane (307.8 mg, 2.04 mmol). The reaction was stirred at room temperature overnight. The reaction was diluted with ethyl acetate, washed with 5% aqueous citric acid, washed with saturated aqueous sodium chloride, dried with magnesium sulfate, filtered, evaporated. Residue was purified by silica gel chromatography using 0-100% ethyl acetate in heptanes as eluent to give the title compound (451.6 mg, 84.8% yield). LCMS: [M+H] 286.9. $^1$H NMR: (400 MHz, DMSO-d6) δ 11.99 (s, 1H), 7.30 (s, 1H), 4.80 (d, J=0.75 Hz, 2H), 2.12 (s, 3H), 0.86 (s, 9H), 0.07 (s, 6H).

Intermediate 15

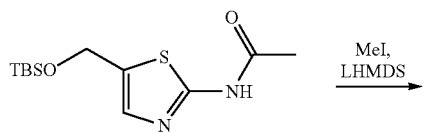

N-[5-[[tert-butyl(dimethyl)silyl]oxymethyl]thiazol-2-yl]-N-methyl-acetamide

To a solution of N-[5-[[tert-butyl(dimethyl)silyl]oxymethyl]thiazol-2-yl]acetamide (584.7 mg, 2.04 mmol) in tetrahydrofuran (7.5 mL) at 0° C. was added lithium bis(trimethylsilyl)amide (1.0 M in tetrahydrofuran, 2.43 mL, 2.43 mmol). The resulting suspension was stirred for 1 hour at 0° C. To the mixture was added iodomethane (421 uL, 3.06 mmol) and the mixture was allowed to warm to room temperature. After stirring for 4 hours, the mixture was diluted with ethyl acetate, then washed with saturated aqueous ammonium chloride. The organics were dried over magnesium sulfate, filtered and concentrated in vacuo. The material was purified over silica gel using 0-100% ethyl acetate in heptanes as eluent to provide the title compound (335.2, 54.7% yield). LCMS: [M+H] 300.9. 1H NMR: (400 MHz, METHANOL-d4) δ 7.31 (s, 1H), 4.86 (d, J=1.00 Hz, 2H), 3.68 (s, 3H), 2.41 (s, 3H), 0.92 (s, 9H), 0.11 (s, 6H).

Intermediate 16

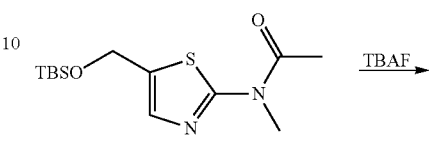

N-[5-(hydroxymethyl)thiazol-2-yl]-N-methyl-acetamide

N-[5-[[tert-butyl(dimethyl)silyl]oxymethyl]thiazol-2-yl]-N-methyl-acetamide (335.2 mg, 1.12 mmol) was dissolved in tetrahydrofuran (6.4 mL). To this was added tetrabutylammonium fluoride (1 M in tetrahydrofuran, 2.23 mL, 2.23 mmol) dropwise at 0° C. After 30 min, the mixture was diluted with ethyl acetate, washed with saturated aqueous ammonium chloride, washed with brine, dried over magnesium sulfate, filtered, and concentrated in vacuo. The residue was purified by silica gel chromatography using 0-10% methanol in methylene chloride as eluent to give the title compound (159.8 mg, 76.6% yield). LCMS: [M+H] 186.9. H NMR: (400 MHz, METHANOL-d4) δ 7.35 (s, 1H), 4.71 (d, J=0.75 Hz, 2H), 3.68 (s, 3H), 2.41 (s, 3H).

Intermediate 17

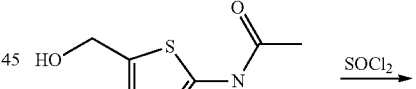

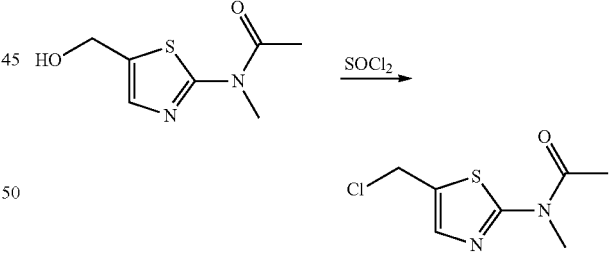

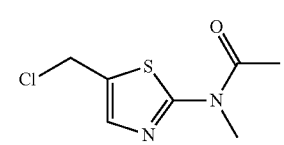

N-[5-(chloromethyl)thiazol-2-yl]-N-methyl-acetamide

To a stirred solution of N-[5-(hydroxymethyl)thiazol-2-yl]-N-methyl-acetamide (50.0 mg, 268 umol) in dichloromethane (5.0 mL), thionyl chloride (60.0 uL, 822 umol) was added slowly at 0° C. The reaction was heated to reflux for 1.5 hours. The reaction was concentrated under reduced pressure. The residue was dissolved in dichloromethane then evaporated (repeat) to provide the title compound. LCMS: [M+H] 201.1 for methyl ether (MeOH as solvent for analytical sample).

Example 3-16

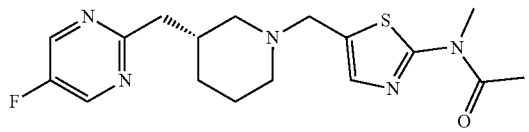 [SMILES: CC(=O)N(C)c1ncc(CN2CCC[C@H](Cc3ncc(F)cn3)C2)s1]

N-[5-[[(3R)-3-[(5-fluoropyrimidin-2-yl)methyl]-1-piperidyl]methyl]thiazol-2-yl]-N-methyl-acetamide The title compound was prepared in an analogous manner of that in scheme 3 from 5-fluoro-2-(piperidin-3-ylmethyl)pyrimidine HCl and N-[5-(chloromethyl)thiazol-2-yl]-N-methyl-acetamide. LCMS: [M+H] 364.2. $^1$H NMR (400 MHz, METHANOL-d4) δ 8.63 (d, J=0.75 Hz, 2H), 7.28 (s, 1H), 3.67 (s, 2H), 3.66 (s, 3H), 2.78-2.87 (m, 4H), 2.41 (s, 3H), 2.23 (m, 1H), 2.02-2.10 (m, 1H), 1.86 (t, J=10.67 Hz, 1H), 1.65-1.74 (m, 2H), 1.50-1.63 (m, 1H), 0.99-1.11 (m, 1H).

Example 3-17

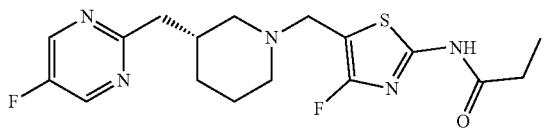 [SMILES: CCC(=O)Nc1nc(F)c(CN2CCC[C@H](Cc3ncc(F)cn3)C2)s1]

(R)-N-(4-fluoro-5-((3-((5-fluoropyrimidin-2-yl)methyl)piperidin-1-yl)methyl)thiazol-2-yl)propionamide The title compound was prepared according to the general procedure described in scheme 3 and using (R)-5-fluoro-2-(piperidin-3-ylmethyl)pyrimidine and N-(4-fluoro-5-formylthiazol-2-yl)propionamide. LCMS (ESI): [M+H] 382. $^1$HNMR: (400 MHz, Methanol-d$_4$) δ 8.64 (d, J=0.75 Hz, 2H), 3.64 (s, 2H), 2.73-3.00 (m, 4H), 2.46 (q, J=7.53 Hz, 2H), 2.08-2.31 (m, 2H), 1.91-2.04 (m, 1H), 1.49-1.79 (m, 3H), 1.19 (t, J=7.53 Hz, 3H), 0.98-1.13 (m, 1H).

Example 3-18

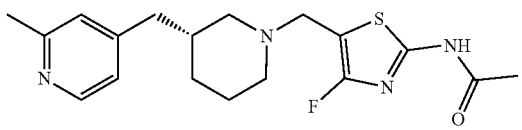 [SMILES: CC(=O)Nc1nc(F)c(CN2CCC[C@H](Cc3ccnc(C)c3)C2)s1]

(R)-N-(4-fluoro-5-((3-((2-methylpyridin-4-yl)methyl)piperidin-1-yl)methyl)thiazol-2-yl)acetamide The title compound was prepared according to the general procedure described in scheme 3 and using (R)-2-methyl-4-(piperidin-3-ylmethyl)pyridine and N-(4-fluoro-5-formylthiazol-2-yl)acetamide. LCMS (ESI): [M+H] 363. $^1$HNMR: (400 MHz, Methanol-d$_4$) δ 8.24 (d, J=5.27 Hz, 1H), 7.11 (s, 1H), 7.04 (dd, J=1.25, 5.27 Hz, 1H), 3.59 (s, 2H), 2.69-2.92 (m, 2H), 2.54 (d, J=7.03 Hz, 2H), 2.47 (s, 3H), 2.18 (s, 3H), 2.07-2.22 (m, 1H), 1.78-1.92 (m, 2H), 1.62-1.78 (m, 2H), 1.45-1.62 (m, 1H), 0.93-1.15 (m, 1H).

Example 3-19

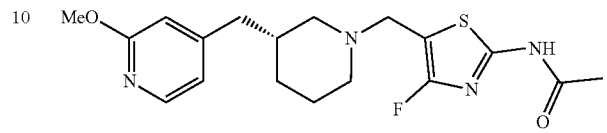

(R)-N-(4-fluoro-5-((3-((2-methoxypyridin-4-yl)methyl)piperidin-1-yl)methyl)thiazol-2-yl)acetamide The title compound was prepared according to the general procedure described in scheme 3 and using (R)-2-methoxy-4-(piperidin-3-ylmethyl)pyridine and N-(4-fluoro-5-formylthiazol-2-yl)acetamide. LCMS (ESI): [M+H] 379. $^1$HNMR: (400 MHz, Methanol-d$_4$) δ 7.97 (d, J=5.27 Hz, 1H), 6.78 (dd, J=1.38, 5.40 Hz, 1H), 6.60 (s, 1H), 3.87 (s, 3H), 3.56 (s, 2H), 2.68-2.88 (m, 2H), 2.43-2.57 (m, 2H), 2.18 (s, 3H), 2.01-2.12 (m, 1H), 1.76-1.96 (m, 2H), 1.63-1.73 (m, 2H), 1.46-1.61 (m, 1H), 0.89-1.11 (m, 1H).

Example 3-20

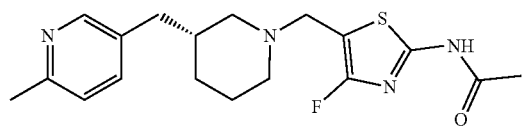 [SMILES: CC(=O)Nc1nc(F)c(CN2CCC[C@H](Cc3ccc(C)nc3)C2)s1]

(R)-N-(4-fluoro-5-((3-((6-methylpyridin-3-yl)methyl)piperidin-1-yl)methyl)thiazol-2-yl)acetamide The title compound was prepared according to the general procedure described in scheme 3 and using (R)-2-methyl-5-(piperidin-3-ylmethyl)pyridine and N-(4-fluoro-5-formylthiazol-2-yl)acetamide. LCMS (ESI): [M+H] 363. $^1$HNMR: (400 MHz, Methanol-d$_4$) δ 8.19 (d, J=1.76 Hz, 1H), 7.54 (dd, J=2.26, 7.78 Hz, 1H), 7.21 (d, J=7.78 Hz, 1H), 3.60 (s, 2H), 2.71-2.92 (m, 2H), 2.53 (br d, J=5.52 Hz, 2H), 2.48 (s, 3H), 2.18 (s, 3H), 2.04-2.13 (m, 1H), 1.77-1.91 (m, 2H), 1.60-1.74 (m, 2H), 1.43-1.57 (m, 1H), 0.85-1.10 (m, 1H).

Example 3-21

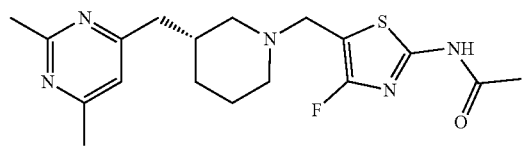 [SMILES: CC(=O)Nc1nc(F)c(CN2CCC[C@H](Cc3cc(C)nc(C)n3)C2)s1]

(R)-N-(5-((3-((2,6-dimethylpyrimidin-4-yl)methyl)piperidin-1-yl)methyl)-4-fluorothiazol-2-yl)acetamide The title compound was prepared according to the general procedure described in scheme 3 and using (R)-2,4-dimethyl-6-(piperidin-3-ylmethyl)pyrimidine and N-(4-fluoro-5-formylthiazol-2-yl)acetamide. LCMS (ESI): [M+H] 378. ¹HNMR: (400 MHz, Methanol-$d_4$) δ 7.05 (s, 1H), 3.48-3.67 (m, 2H), 2.68-2.88 (m, 2H), 2.52-2.65 (m, 2H), 2.58 (s, 3H), 2.43 (s, 3H), 2.18 (s, 3H), 1.97-2.16 (m, 2H), 1.78-1.90 (m, 1H), 1.63-1.74 (m, 2H), 1.47-1.61 (m, 1H), 0.96-1.16 (m, 1H).

Example 3-22

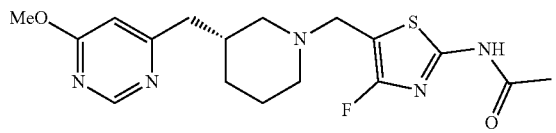 [SMILES: COc1cc(C[C@H]2CCCN(Cc3sc(NC(C)=O)nc3F)C2)ncn1]

(R)-N-(4-fluoro-5-((3-((6-methoxypyrimidin-4-yl)methyl)piperidin-1-yl)methyl)thiazol-2-yl)acetamide The title compound was prepared according to the general procedure described in scheme 3 and using (R)-4-methoxy-6-(piperidin-3-ylmethyl)pyrimidine and N-(4-fluoro-5-formylthiazol-2-yl)acetamide. LCMS (ESI): [M+H] 380. ¹HNMR: (400 MHz, Methanol-$d_4$) δ 8.61 (d, J=1.00 Hz, 1H), 6.71 (d, J=1.00 Hz, 1H), 3.97 (s, 3H), 3.52-3.66 (m, 2H), 2.75-2.88 (m, 2H), 2.48-2.66 (m, 2H), 2.18 (s, 3H), 1.99-2.12 (m, 2H), 1.81-1.95 (m, 1H), 1.47-1.78 (m, 3H), 0.95-1.17 (m, 1H).

Example 3-23

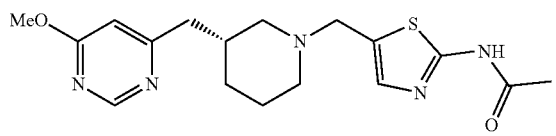 [SMILES: COc1cc(C[C@H]2CCCN(Cc3cnc(NC(C)=O)s3)C2)ncn1]

(R)-N-(5-((3-((6-methoxypyrimidin-4-yl)methyl)piperidin-1-yl)methyl)thiazol-2-yl)acetamide The title compound was prepared according to the general procedure described in scheme 3 and using (R)-4-methoxy-6-(piperidin-3-ylmethyl)pyrimidine. LCMS (ESI): [M+H] 362. ¹HNMR: (400 MHz, Methanol-$d_4$) δ 8.60 (d, J=1.00 Hz, 1H), 7.21 (s, 1H), 6.71 (d, J=1.00 Hz, 1H), 3.96 (s, 3H), 3.60-3.75 (m, 2H), 2.67-2.90 (m, 2H), 2.44-2.67 (m, 2H), 2.20 (s, 3H), 1.96-2.16 (m, 2H), 1.76-1.95 (m, 1H), 1.46-1.76 (m, 3H), 0.96-1.15 (m, 1H).

Example 3-24

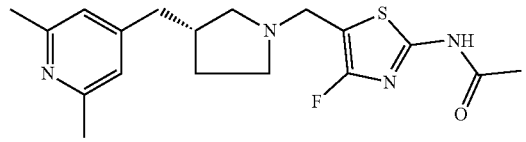 [SMILES: CC(=O)Nc1nc(F)c(CN2CC[C@H](Cc3cc(C)nc(C)c3)C2)s1]

(S)—N-(5-((3-((2,6-dimethylpyridin-4-yl)methyl)pyrrolidin-1-yl)methyl)-4-fluorothiazol-2-yl)acetamide The title compound was prepared in an analogous manner of that in scheme 3 from (S)-2,6-dimethyl-4-(pyrrolidin-3-ylmethyl)pyridine and N-(4-fluoro-5-formylthiazol-2-yl)acetamide. LCMS (ESI): [M+H] 363. ¹H NMR (400 MHz, Methanol-$d_4$) δ 6.93 (s, 2H), 3.62-3.77 (m, 2H), 2.60-2.77 (m, 5H), 2.48-2.58 (m, 1H), 2.44 (s, 6H), 2.27-2.36 (m, 1H), 2.18 (s, 3H), 1.94-2.07 (m, 1H), 1.47-1.58 (m, 1H).

Example 3-25

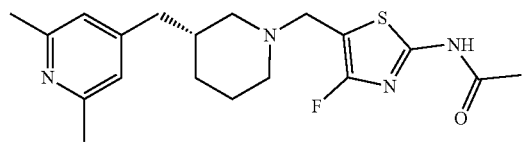 [SMILES: CC(=O)Nc1nc(F)c(CN2CCC[C@H](Cc3cc(C)nc(C)c3)C2)s1]

(R)-N-(5-((3-((2,6-dimethylpyridin-4-yl)methyl)piperidin-1-yl)methyl)-4-fluorothiazol-2-yl)acetamide The title compound was prepared in an analogous manner of that in scheme 3 from (R)-2,6-dimethyl-4-(piperidin-3-ylmethyl)pyridine and N-(4-fluoro-5-formylthiazol-2-yl)acetamide. LCMS (ESI): [M+H] 377. ¹H NMR (400 MHz, Methanol-$d_4$) δ 6.89 (s, 2H), 3.51-3.63 (m, 2H), 2.82 (br d, J=11.04 Hz, 1H), 2.73 (br d, J=9.79 Hz, 1H), 2.49 (d, J=7.03 Hz, 2H), 2.43 (s, 6H), 2.18 (s, 3H), 2.05-2.15 (m, 1H), 1.76-1.94 (m, 2H), 1.63-1.75 (m, 2H), 1.49-1.62 (m, 1H), 0.93-1.09 (m, 1H). LCMS (ESI): [M+H] 377.

Example 3-26

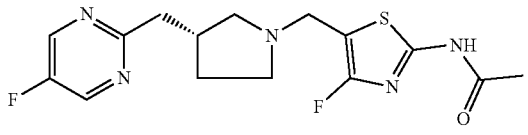 [SMILES: CC(=O)Nc1nc(F)c(CN2CC[C@H](Cc3ncc(F)cn3)C2)s1]

(R)-N-(4-fluoro-5-((3-((5-fluoropyrimidin-2-yl)methyl)pyrrolidin-1-yl)methyl)thiazol-2-yl)acetamide The title compound was prepared in an analogous manner of that in scheme 3 from (R)-5-fluoro-2-(pyrrolidin-3-ylmethyl)pyrimidine and N-(4-fluoro-5-formylthiazol-2-yl)acetamide. LCMS (ESI): [M+H] 354. ¹H NMR (400 MHz, Methanol-d₄) δ 8.64 (d, J=0.75 Hz, 2H), 3.65-3.79 (m, 2H), 3.02 (d, J=7.53 Hz, 2H), 2.56-2.92 (m, 4H), 2.40 (dd, J=6.78, 9.03 Hz, 1H), 2.18 (s, 3H), 1.96-2.10 (m, 1H), 1.61 (tdd, J=6.40, 8.28, 12.80 Hz, 1H).

Example 3-27

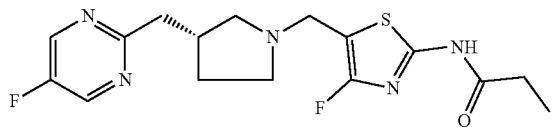 [SMILES: CCC(=O)Nc1nc(F)c(CN2CC[C@H](Cc3ncc(F)cn3)C2)s1]

(R)-N-(4-fluoro-5-((3-((5-fluoropyrimidin-2-yl)methyl)pyrrolidin-1-yl)methyl)thiazol-2-yl)propionamide The title compound was prepared in an analogous manner of that in scheme 3 from (R)-5-fluoro-2-(pyrrolidin-3-ylmethyl)pyrimidine and N-(4-fluoro-5-formylthiazol-2-yl)propionamide. LCMS (ESI): [M+H] 368. ¹H NMR (400 MHz, Methanol-d₄) δ 8.69 (s, 2H), 4.52 (s, 2H), 3.50-3.92 (m, 2H), 3.35-3.49 (m, 1H), 2.89-3.28 (m, 4H), 2.50 (q, J=7.53 Hz, 2H), 2.22-2.45 (m, 1H), 1.70-2.01 (m, 1H), 1.20 (t, J=7.53 Hz, 3H).

Example 3-28

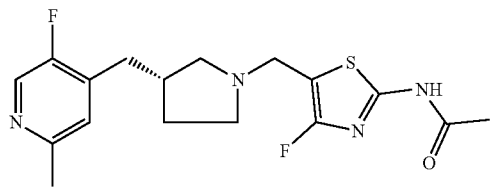 [SMILES: CC(=O)Nc1nc(F)c(CN2CC[C@H](Cc3cc(C)ncc3F)C2)s1]

(S)—N-(4-fluoro-5-((3-((5-fluoro-2-methylpyridin-4-yl)methyl)pyrrolidin-1-yl)methyl)thiazol-2-yl)acetamide The title compound was prepared in an analogous manner of that in scheme 3 from (S)-5-fluoro-2-methyl-4-(pyrrolidin-3-ylmethyl)pyridine and N-(4-fluoro-5-formylthiazol-2-yl)acetamide. LCMS (ESI): [M+H] 367. ¹H NMR (400 MHz, Methanol-d₄) δ 8.57 (d, J=2.76 Hz, 1H), 7.62 (d, J=6.27 Hz, 1H), 4.49-4.57 (m, 2H), 3.44-3.78 (m, 3H), 2.97-3.08 (m, 2H), 2.75-2.93 (m, 1H), 2.64 (s, 3H), 2.15-2.36 (m, 5H), 1.80-2.00 (m, 1H).

Example 3-29

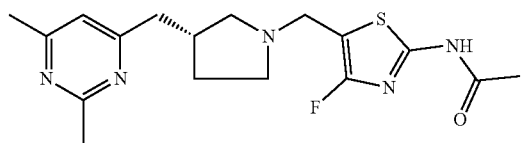 [SMILES: CC(=O)Nc1nc(F)c(CN2CC[C@H](Cc3cc(C)nc(C)n3)C2)s1]

(R)-N-(5-((3-((2,6-dimethylpyrimidin-4-yl)methyl)pyrrolidin-1-yl)methyl)-4-fluorothiazol-2-yl)acetamide The title compound was prepared in an analogous manner of that in scheme 3 from (R)-2,4-dimethyl-6-(pyrrolidin-3-ylmethyl)pyrimidine and N-(4-fluoro-5-formylthiazol-2-yl)acetamide. LCMS (ESI): [M+H] 364. ¹H NMR (400 MHz, Methanol-d₄) δ 7.42 (s, 1H), 4.52 (s, 2H), 3.36-3.85 (m, 4H), 2.94-3.08 (m, 3H), 2.74 (s, 3H), 2.60 (s, 3H), 2.24-2.39 (m, 1H), 2.21 (s, 3H), 1.80-1.99 (m, 1H).

Example 3-30

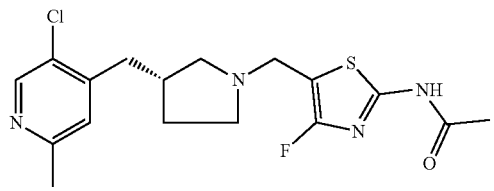 [SMILES: CC(=O)Nc1nc(F)c(CN2CC[C@H](Cc3cc(C)ncc3Cl)C2)s1]

(S)—N-(5-((3-((5-chloro-2-methylpyridin-4-yl)methyl)pyrrolidin-1-yl)methyl)-4-fluorothiazol-2-yl)acetamide The title compound was prepared in an analogous manner of that in scheme 3 from (S)-5-chloro-2-methyl-4-(pyrrolidin-3-ylmethyl)pyridine and N-(4-fluoro-5-formylthiazol-2-yl)acetamide. LCMS (ESI): [M+H] 383. ¹H NMR (400 MHz, Methanol-d₄) δ 8.61 (s, 1H), 7.55 (s, 1H), 4.52 (d, J=1.51 Hz, 2H), 3.38-3.84 (m, 3H), 3.22 (br d, J=8.03 Hz, 1H), 2.98-3.13 (m, 2H), 2.72-2.96 (m, 1H), 2.61 (s, 3H), 2.14-2.34 (m, 4H), 1.92 (br d, J=16.06 Hz, 1H).

Example 3-31

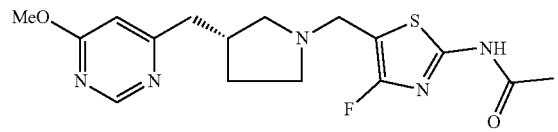 [SMILES: COc1cc(C[C@H]2CCN(Cc3sc(NC(C)=O)nc3F)C2)ncn1]

(R)-N-(4-fluoro-5-((3-((6-methoxypyrimidin-4-yl)methyl)pyrrolidin-1-yl)methyl)thiazol-2-yl)acetamide The title compound was prepared in an analogous manner of that in scheme 3 from (R)-4-methoxy-6-(pyrrolidin-3-ylmethyl)pyrimidine and N-(4-fluoro-5-formylthiazol-2-yl)acetamide. LCMS (ESI): [M+H] 366. ¹H NMR (400 MHz, Methanol-d₄) δ 8.63 (d, J=0.75 Hz, 1H), 6.75 (d, J=0.75 Hz, 1H), 3.97 (s, 3H), 3.82 (d, J=0.75 Hz, 2H), 2.91 (dd, J=7.53, 9.54 Hz, 1H), 2.75-2.85 (m, 4H), 2.65-2.73 (m, 1H), 2.47 (dd, J=7.15, 9.66 Hz, 1H), 2.19 (s, 3H), 2.00-2.07 (m, 1H), 1.55-1.66 (m, 1H).

Example 3-32

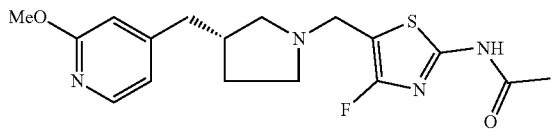 [SMILES: COc1cc(C[C@H]2CCN(Cc3sc(NC(C)=O)nc3F)C2)ccn1]

(S)—N-(4-fluoro-5-((3-((2-methoxypyridin-4-yl)methyl)pyrrolidin-1-yl)methyl)thiazol-2-yl)acetamide The title compound was prepared in an analogous manner of that in scheme 3 from (S)-2-methoxy-4-(pyrrolidin-3-ylmethyl)pyridine and N-(4-fluoro-5-formylthiazol-2-yl)acetamide. LCMS (ESI): [M+H] 365. $^1$H NMR (400 MHz, Methanol-$d_4$) δ 7.99 (d, J=5.27 Hz, 1H), 6.81 (dd, J=1.25, 5.27 Hz, 1H), 6.64 (s, 1H), 3.87 (s, 3H), 3.83 (d, J=2.51 Hz, 2H), 2.89 (dd, J=7.40, 9.66 Hz, 1H), 2.74-2.85 (m, 2H), 2.68 (dd, J=2.38, 7.65 Hz, 2H), 2.56 (td, J=7.87, 15.12 Hz, 1H), 2.44 (dd, J=7.28, 9.54 Hz, 1H), 2.18 (s, 3H), 1.96-2.03 (m, 1H), 1.51-1.66 (m, 1H).

Example 3-33

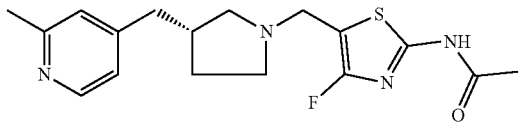 [SMILES: CC(=O)Nc1nc(F)c(CN2CC[C@H](Cc3ccnc(C)c3)C2)s1]

(S)—N-(4-fluoro-5-((3-((2-methylpyridin-4-yl)methyl)pyrrolidin-1-yl)methyl)thiazol-2-yl)acetamide The title compound was prepared in an analogous manner of that in scheme 3 from (S)-2-methoxy-4-(pyrrolidin-3-ylmethyl)pyridine and N-(4-fluoro-5-formylthiazol-2-yl)acetamide. LCMS (ESI): [M+H] 349. $^1$H NMR (400 MHz, Methanol-$d_4$) δ 8.26 (d, J=5.27 Hz, 1H), 7.15 (s, 1H), 7.08 (dd, J=1.00, 5.27 Hz, 1H), 3.62-3.78 (m, 2H), 2.62-2.79 (m, 5H), 2.50-2.60 (m, 1H), 2.48 (s, 3H), 2.31 (dd, J=6.90, 9.41 Hz, 1H), 2.16-2.20 (m, 3H), 1.94-2.05 (m, 1H), 1.46-1.61 (m, 1H).

Example 3-34

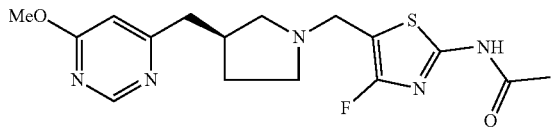 [SMILES: COc1cc(C[C@@H]2CCN(Cc3sc(NC(C)=O)nc3F)C2)ncn1]

(S)—N-(4-fluoro-5-((3-((6-methoxypyrimidin-4-yl)methyl)pyrrolidin-1-yl)methyl)thiazol-2-yl)acetamide The title compound was prepared in an analogous manner of that in scheme 3 from (S)-4-methoxy-6-(pyrrolidin-3-ylmethyl)pyrimidine and N-(4-fluoro-5-formylthiazol-2-yl)acetamide. LCMS (ESI): [M+H] 366. $^1$H NMR (400 MHz, Methanol-$d_4$) δ 8.62 (d, J=1.00 Hz, 1H), 6.75 (d, J=1.00 Hz, 1H), 3.97 (s, 3H), 3.76 (d, J=1.51 Hz, 2H), 2.85 (dd, J=7.53, 9.54 Hz, 1H), 2.65-2.80 (m, 5H), 2.40 (dd, J=6.90, 9.41 Hz, 1H), 2.18 (s, 3H), 1.96-2.08 (m, 1H), 1.58 (tdd, J=6.49, 8.16, 12.99 Hz, 1H).

Example 3-35

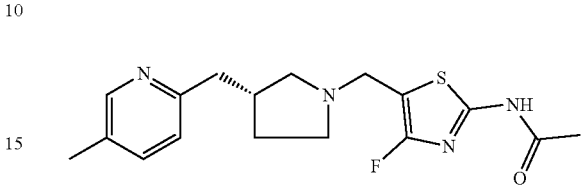

(S)—N-(4-fluoro-5-((3-((6-methylpyridin-3-yl)methyl)pyrrolidin-1-yl)methyl)thiazol-2-yl)acetamide The title compound was prepared in an analogous manner of that in scheme 3 from (S)-4-methoxy-6-(pyrrolidin-3-ylmethyl)pyrimidine and N-(4-fluoro-5-formylthiazol-2-yl)acetamide. LCMS (ESI): [M+H] 349. $^1$H NMR (400 MHz, Methanol-$d_4$) δ 8.23 (d, J=2.01 Hz, 1H), 7.58 (dd, J=2.38, 7.91 Hz, 1H), 7.21 (d, J=7.78 Hz, 1H), 3.64-3.76 (m, 2H), 2.61-2.80 (m, 5H), 2.43-2.55 (m, 4H), 2.31 (dd, J=6.78, 9.29 Hz, 1H), 2.18 (s, 3H), 1.94-2.00 (m, 1H), 1.54 (tdd, J=6.53, 8.22, 12.86 Hz, 1H).

Example 3-36

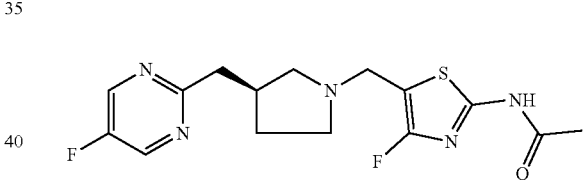

(S)—N-(4-fluoro-5-((3-((5-fluoropyrimidin-2-yl)methyl)pyrrolidin-1-yl)methyl)thiazol-2-yl)acetamide The title compound was prepared in an analogous manner of that in scheme 3 from (S)-5-fluoro-2-(pyrrolidin-3-ylmethyl)pyrimidine and N-(4-fluoro-5-formylthiazol-2-yl)acetamide. LCMS (ESI): [M+H] 354. $^1$H NMR (400 MHz, Methanol-$d_4$) δ 8.65 (d, J=0.75 Hz, 2H), 3.89 (s, 2H), 3.01-3.10 (m, 3H), 2.78-2.95 (m, 3H), 2.58 (dd, J=7.53, 10.04 Hz, 1H), 2.19 (s, 3H), 2.04-2.16 (m, 1H), 1.60-1.74 (m, 1H).

Example 3-37

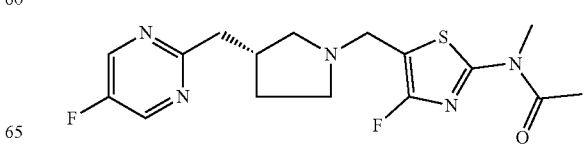

(R)-N-(4-fluoro-5-((3-((5-fluoropyrimidin-2-yl)methyl)pyrrolidin-1-yl)methyl)thiazol-2-yl)-N-methylacetamide To a mixture of N-[4-fluoro-5-[[(3R)-3-[(5-fluoropyrimidin-2-yl)methyl]pyrrolidin-1-yl]methyl]thiazol-2-yl]acetamide (25 mg, 71 umol) and methanol (34 mg, 1.06 mmol), triphenylphosphine (37 mg, 142 umol) in THF (0.5 mL) was added isopropyl (NE)-N-isopropoxycarbonyliminocarbamate (43 mg, 212 umol). The reaction mixture was then stirred at RT overnight. Remove all the solvent. The crude was purified by chromatography on silica gel (solvent A: EtOAc, solvent B: 0-60% EtOAc-EtOH 3:1 with 2% NH4OH) to give the title compound as a white powder. LCMS (ESI): [M+H] 368. $^1$H NMR (400 MHz, METHANOL-d$_4$) δ 8.64 (d, J=0.75 Hz, 2H), 3.66-3.76 (m, 2H), 3.59-3.64 (m, 3H), 3.02 (d, J=7.53 Hz, 2H), 2.68-2.89 (m, 3H), 2.64 (dt, J=6.02, 8.78 Hz, 1H), 2.35-2.44 (m, 4H), 1.96-2.08 (m, 1H), 1.61 (tdd, J=6.31, 8.28, 12.74 Hz, 1H).

Example 3-38

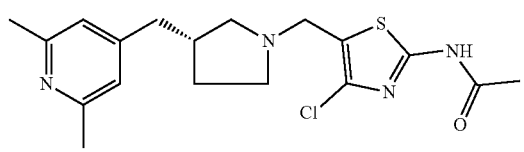 [SMILES: CC(=O)Nc1nc(Cl)c(CN2CC[C@H](Cc3cc(C)nc(C)c3)C2)s1]

(S)—N-(4-chloro-5-((3-((2,6-dimethylpyridin-4-yl)methyl)pyrrolidin-1-yl)methyl)thiazol-2-yl)acetamide The title compound was prepared in an analogous manner of that in scheme 3 from 4-methoxy-6-(1-(pyrrolidin-3-yl)ethyl)pyrimidine and N-(4-chloro-5-formylthiazol-2-yl)acetamide. LCMS (ESI): [M+H] 379. $^1$H NMR (400 MHz, Methanol-d$_4$) δ 6.94 (s, 2H), 3.73-3.87 (m, 2H), 2.70-2.78 (m, 3H), 2.62-2.67 (m, 2H), 2.49-2.57 (m, 1H), 2.44 (s, 6H), 2.36 (dd, J=6.65, 9.41 Hz, 1H), 2.19 (s, 3H), 1.95-2.00 (m, 1H), 1.47-1.60 (m, 1H).

Example 3-39

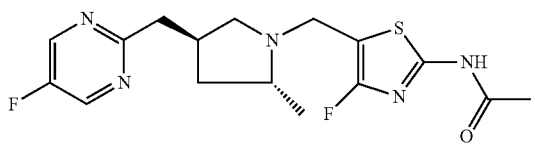 [SMILES: CC(=O)Nc1nc(F)c(CN2C[C@H](Cc3ncc(F)cn3)C[C@H]2C)s1]

N-(4-fluoro-5-(((2R,4S)-4-((5-fluoropyrimidin-2-yl)methyl)-2-methylpyrrolidin-1-yl)methyl)thiazol-2-yl)acetamide The title compound was isolated through chiral separation (CHIRALPAK IG 30×250 mm, 5um; Method: 30% MeOH w/ 0.1% DEA in CO$_2$ (flow rate: 100 mL/min, ABPR 120 bar, MBPR 40 psi, column temp 40 C) of a mixture which was prepared in an analogous manner of that in scheme 3 from 5-fluoro-2-((5-methylpyrrolidin-3-yl)methyl)pyrimidine and N-(4-fluoro-5-formylthiazol-2-yl)acetamide. LCMS (ESI): [M+H] 368. $^1$H NMR (400 MHz, Methanol-d$_4$) δ 8.63 (d, J=0.75 Hz, 2H), 3.86-3.96 (m, 1H), 3.55 (d, J=14.31 Hz, 1H), 3.12 (dd, J=7.28, 9.29 Hz, 1H), 2.95 (d, J=7.28 Hz, 2H), 2.53-2.83 (m, 2H), 2.11-2.24 (m, 4H), 1.73-1.85 (m, 1H), 1.64 (ddd, J=8.28, 9.79, 12.80 Hz, 1H), 1.15 (d, J=6.02 Hz, 3H).

Example 3-40

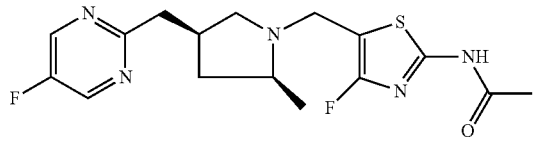 [SMILES: CC(=O)Nc1nc(F)c(CN2C[C@H](Cc3ncc(F)cn3)C[C@@H]2C)s1]

N-(4-fluoro-5-(((2S,4S)-4-((5-fluoropyrimidin-2-yl)methyl)-2-methylpyrrolidin-1-yl)methyl)thiazol-2-yl)acetamide The title compound was isolated through chiral separation (CHIRALPAK IG 30×250 mm, 5um; Method: 30% MeOH w/ 0.1% DEA in CO$_2$ (flow rate: 100 mL/min, ABPR 120 bar, MBPR 40 psi, column temp 40 C) of a mixture which was prepared in an analogous manner of that in scheme 3 from 5-fluoro-2-((5-methylpyrrolidin-3-yl)methyl)pyrimidine and N-(4-fluoro-5-formylthiazol-2-yl)acetamide. LCMS (ESI): [M+H] 368. $^1$H NMR (400 MHz, Methanol-d$_4$) δ 8.63 (d, J=0.75 Hz, 2H), 3.90 (dd, J=1.00, 14.56 Hz, 1H), 3.52 (d, J=14.56 Hz, 1H), 3.01 (dd, J=2.26, 7.28 Hz, 2H), 2.87 (dd, J=3.64, 9.41 Hz, 1H), 2.52-2.70 (m, 3H), 2.18 (s, 3H), 2.11 (ddd, J=6.27, 8.28, 12.55 Hz, 1H), 1.21-1.29 (m, 1H), 1.16 (d, J=6.02 Hz, 3H).

Example 3-41

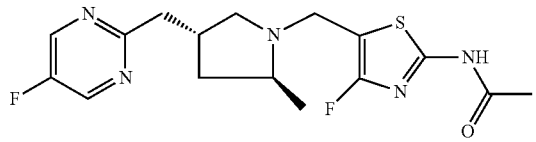 [SMILES: CC(=O)Nc1nc(F)c(CN2C[C@@H](Cc3ncc(F)cn3)C[C@@H]2C)s1]

N-(4-fluoro-5-(((2S,4R)-4-((5-fluoropyrimidin-2-yl)methyl)-2-methylpyrrolidin-1-yl)methyl)thiazol-2-yl)acetamide The title compound was isolated through chiral separation (CHIRALPAK IG 30×250 mm, 5um; Method: 30% MeOH w/ 0.1% DEA in CO$_2$ (flow rate: 100 mL/min, ABPR 120 bar, MBPR 40 psi, column temp 40 C) of a mixture which was prepared in an analogous manner of that in scheme 3 from 5-fluoro-2-((5-methylpyrrolidin-3-yl)methyl)pyrimidine and N-(4-fluoro-5-formylthiazol-2-yl)acetamide. LCMS (ESI): [M+H] 368. $^1$H NMR (400 MHz, Methanol-d$_4$) δ 8.63 (d, J=0.75 Hz, 2H), 3.91 (dd, J=0.75, 14.56 Hz, 1H), 3.55 (d, J=14.56 Hz, 1H), 3.12 (dd, J=7.03, 9.29 Hz, 1H), 2.95 (d, J=7.53 Hz, 2H), 2.67-2.80 (m, 1H), 2.57-2.67 (m, 1H), 2.12-2.22 (m, 4H), 1.79 (ddd, J=5.77, 7.65, 13.18 Hz, 1H),

Example 3-42

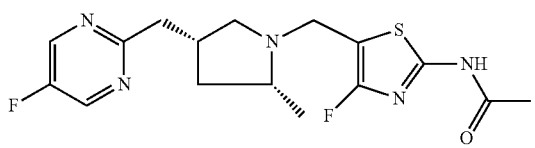 [SMILES: CC(=O)Nc1nc(F)c(CN2C[C@@H](Cc3ncc(F)cn3)C[C@H]2C)s1]

N-(4-fluoro-5-(((2R,4R)-4-((5-fluoropyrimidin-2-yl)methyl)-2-methylpyrrolidin-1-yl)methyl)thiazol-2-yl)acetamide The title compound was isolated through chiral separation (CHIRALPAK IG 30×250 mm, 5um; Method: 30% MeOH w/ 0.1% DEA in $CO_2$ (flow rate: 100 mL/min, ABPR 120 bar, MBPR 40 psi, column temp 40 C) of a mixture which was prepared in an analogous manner of that in scheme 3 from 5-fluoro-2-((5-methylpyrrolidin-3-yl)methyl)pyrimidine and N-(4-fluoro-5-formylthiazol-2-yl)acetamide. LCMS (ESI): [M+H] 368. $^1$H NMR (400 MHz, Methanol-$d_4$) δ 8.63 (d, J=0.75 Hz, 1H), 8.55-8.71 (m, 1H), 3.90 (dd, J=1.00, 14.56 Hz, 1H), 3.52 (d, J=14.31 Hz, 1H), 3.01 (dd, J=2.26, 7.28 Hz, 2H), 2.87 (dd, J=3.76, 9.54 Hz, 1H), 2.59-2.71 (m, 1H), 2.51-2.59 (m, 2H), 2.18 (s, 3H), 2.11 (ddd, J=6.40, 8.22, 12.49 Hz, 1H), 1.22-1.29 (m, 1H), 1.16 (d, J=6.02 Hz, 3H).

Example 3-43

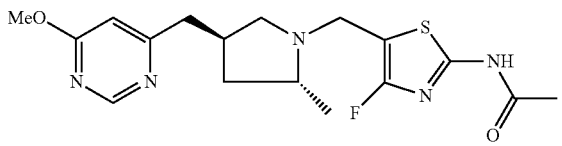 [SMILES: COc1cc(C[C@@H]2C[C@@H](C)N(Cc3sc(NC(C)=O)nc3F)C2)ncn1]

N-(4-fluoro-5-(((2R,4S)-4-((6-methoxypyrimidin-4-yl)methyl)-2-methylpyrrolidin-1-yl)methyl)thiazol-2-yl)acetamide The title compound was isolated through chiral separation (CHIRALPAK AD-H 30×250 mm, 5 um; Method: 45% MeOH w/ 0.1% DEA in $CO_2$ (flow rate: 100 mL/min, ABPR 120 bar, MBPR 40 psi, column temp 40 C) of a mixture which was prepared in an analogous manner of that in scheme 3 from 4-methoxy-6-((5-methylpyrrolidin-3-yl)methyl)pyrimidine and N-(4-fluoro-5-formylthiazol-2-yl)acetamide. LCMS (ESI): [M+H] 380. $^1$H NMR (400 MHz, Methanol-$d_4$) δ 8.61 (d, J=1.00 Hz, 1H), 6.73 (d, J=1.00 Hz, 1H), 3.97 (s, 3H), 3.88-3.94 (m, 1H), 3.55 (d, J=14.56 Hz, 1H), 3.07 (dd, J=6.90, 9.16 Hz, 1H), 2.53-2.73 (m, 4H), 2.18 (s, 3H), 2.12 (t, J=9.03 Hz, 1H), 1.68-1.79 (m, 1H), 1.55-1.66 (m, 1H), 1.14 (d, J=6.02 Hz, 3H).

Example 3-44

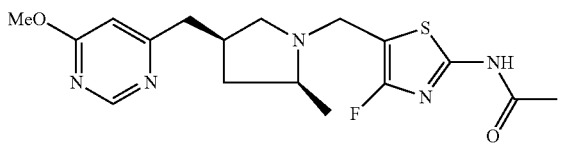 [SMILES: COc1cc(C[C@@H]2C[C@H](C)N(Cc3sc(NC(C)=O)nc3F)C2)ncn1]

N-(4-fluoro-5-(((2S,4S)-4-((6-methoxypyrimidin-4-yl)methyl)-2-methylpyrrolidin-1-yl)methyl)thiazol-2-yl)acetamide The title compound was isolated through chiral separation (CHIRALPAK AD-H 30×250 mm, 5um; Method: 45% MeOH w/ 0.1% DEA in $CO_2$ (flow rate: 100 mL/min, ABPR 120 bar, MBPR 40 psi, column temp 40 C) of a mixture which prepared in an analogous manner of that in scheme 3 from 4-methoxy-6-((5-methylpyrrolidin-3-yl)methyl)pyrimidine and N-(4-fluoro-5-formylthiazol-2-yl)acetamide. LCMS (ESI): [M+H] 380. $^1$H NMR (400 MHz, Methanol-$d_4$) δ 8.61 (d, J=1.00 Hz, 1H), 6.72 (d, J=1.00 Hz, 1H), 3.96 (s, 3H), 3.91 (dd, J=1.00, 14.56 Hz, 1H), 3.51 (d, J=14.31 Hz, 1H), 2.67-2.82 (m, 3H), 2.46-2.63 (m, 3H), 2.19 (s, 3H), 2.04-2.16 (m, 1H), 1.20-1.25 (m, 1H), 1.18 (d, J=6.02 Hz, 3H).

Example 3-45

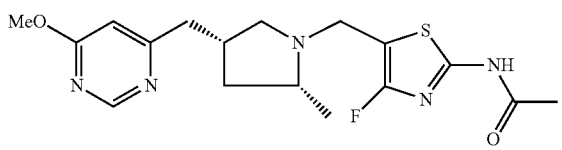 [SMILES: COc1cc(C[C@H]2C[C@@H](C)N(Cc3sc(NC(C)=O)nc3F)C2)ncn1]

N-(4-fluoro-5-(((2R,4R)-4-((6-methoxypyrimidin-4-yl)methyl)-2-methylpyrrolidin-1-yl)methyl)thiazol-2-yl)acetamide The title compound was isolated through chiral separation (CHIRALPAK AD-H 30×250 mm, 5 um; Method: 45% MeOH w/ 0.1% DEA in $CO_2$ (flow rate: 100 mL/min, ABPR 120 bar, MBPR 40 psi, column temp 40 C) of a mixture which prepared in an analogous manner of that in scheme 3 from 4-methoxy-6-((5-methylpyrrolidin-3-yl)methyl)pyrimidine and N-(4-fluoro-5-formylthiazol-2-yl)acetamide. LCMS (ESI): [M+H] 380. $^1$H NMR (400 MHz, Methanol-$d_4$) δ 8.61 (d, J=1.00 Hz, 1H), 6.72 (d, J=1.00 Hz, 1H), 3.96 (s, 3H), 3.91 (dd, J=1.13, 14.43 Hz, 1H), 3.51 (d, J=14.31 Hz, 1H), 2.68-2.81 (m, 3H), 2.46-2.61 (m, 3H), 2.19 (s, 3H), 2.05-2.15 (m, 1H), 1.19-1.24 (m, 1H), 1.17 (d, J=6.02 Hz, 3H).

Example 3-46

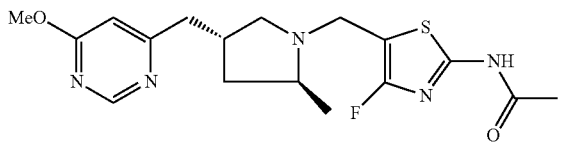 [SMILES: COc1cc(C[C@H]2C[C@H](C)N(Cc3sc(NC(C)=O)nc3F)C2)ncn1]

N-(4-fluoro-5-(((2S,4R)-4-((6-methoxypyrimidin-4-yl)methyl)-2-methylpyrrolidin-1-yl)methyl)thiazol-2-yl)acetamide The title compound was isolated through chiral separation (CHIRALPAK AD-H 30×250 mm, 5um; Method: 45% MeOH w/ 0.1% DEA in $CO_2$ (flow rate: 100 mL/min, ABPR 120 bar, MBPR 40 psi, column temp 40 C) of a mixture which prepared in an analogous manner of that in scheme 3 from 4-methoxy-6-((5-methylpyrrolidin-3-yl)methyl)pyrimidine and N-(4-fluoro-5-formylthiazol-2-yl)acetamide. LCMS (ESI): [M+H] 380. ¹H NMR (400 MHz, Methanol-d₄) δ 8.61 (d, J=1.00 Hz, 1H), 6.73 (d, J=1.00 Hz, 1H), 3.97 (s, 3H), 3.88-3.94 (m, 1H), 3.55 (d, J=14.56 Hz, 1H), 3.07 (dd, J=6.90, 9.16 Hz, 1H), 2.56-2.72 (m, 4H), 2.18 (s, 3H), 2.12 (t, J=9.16 Hz, 1H), 1.69-1.79 (m, 1H), 1.56-1.67 (m, 1H), 1.14 (d, J=6.02 Hz, 3H).

Example 3-47

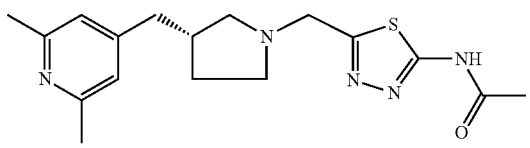 [SMILES: CC(=O)Nc1nnc(CN2CC[C@H](Cc3cc(C)nc(C)c3)C2)s1]

(S)—N-(5-((3-((2,6-dimethylpyridin-4-yl)methyl)pyrrolidin-1-yl)methyl)-1,3,4-thiadiazol-2-yl)acetamide To a mixture of 2,6-dimethyl-4-[[(3S)-pyrrolidin-3-yl]methyl]pyridine (200 mg, 0.31 mmol, trifluoroacetic acid) and 5-(chloromethyl)-1,3,4-thiadiazol-2-amine (91 mg, 0.37 mmol, methanesulfonic acid) in acetonitrile (2.00 mL) and DMF (1.0 mL) was added diisopropylethylamine (320 mg, 2.48 mmol). The reaction was stirred at room temperature for 2 h. The mixture was concentrated in vacuo, diluted with EtOAc, washed with brine, and the crude residue was purified by chromatography on silica gel (20-100% EtOAc-EtOH 3:1 with 2% NH₄OH in heptane) to give 5-[[(3S)-3-[(2,6-dimethyl-4-pyridyl)methyl]pyrrolidin-1-yl]methyl]-1,3,4-thiadiazol-2-amine (26 mg, LCMS (ESI): [M+H] 304) which was dissolved in dichloromethane (1.0 mL) stirred at room temperature, diisopropylethylamine (21 mg, 0.17 mmol) was then added, followed by acetic anhydride (10 mg, 0.99 mmol), and the mixture was stirred at room temperature overnight. The mixture was concentrated in vacuo and residue was purified by preparative TLC to afford the title compound (6 mg, 26% yield). LCMS (ESI): [M+H] 346. ¹H NMR (400 MHz, Methanol-d₄) δ 7.21 (br s, 2H), 4.09-4.25 (m, 2H), 3.72 (br d, J=4.77 Hz, 1H), 2.93 (br d, J=6.78 Hz, 2H), 2.80 (d, J=7.28 Hz, 2H), 2.57-2.71 (m, 2H), 2.55 (s, 6H), 2.25 (s, 2H), 2.24-2.26 (m, 1H), 2.03-2.11 (m, 1H), 1.60-1.68 (m, 1H).

Example 3-48

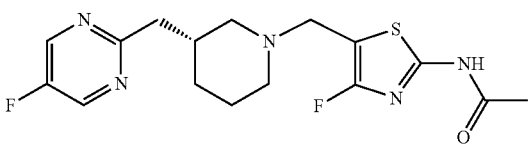 [SMILES: CC(=O)Nc1nc(F)c(CN2CCC[C@H](Cc3ncc(F)cn3)C2)s1]

(R)-N-(4-fluoro-5-((3-((5-fluoropyrimidin-2-yl)methyl)piperidin-1-yl)methyl)thiazol-2-yl)acetamide The title compound was prepared according to the general procedure described in scheme 3 and using (R)-5-fluoro-2-(piperidin-3-ylmethyl)pyrimidine and N-(4-fluoro-5-formylthiazol-2-yl)acetamide. LCMS (ESI): [M+H] 368. ¹HNMR: (400 MHz, Methanol-d₄) δ 8.63 (d, J=0.75 Hz, 2H), 3.56 (s, 2H), 2.70-2.95 (m, 4H), 2.14-2.29 (m, 1H), 2.18 (s, 3H), 2.02-2.12 (m, 1H), 1.82-1.94 (m, 1H), 1.64-1.78 (m, 2H), 1.46-1.62 (m, 1H), 0.92-1.15 (m, 1H).

Example 3-49

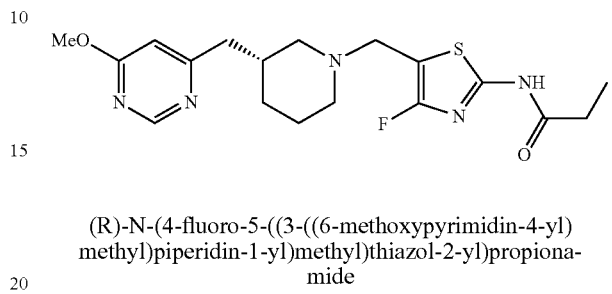

(R)-N-(4-fluoro-5-((3-((6-methoxypyrimidin-4-yl)methyl)piperidin-1-yl)methyl)thiazol-2-yl)propionamide The title compound was prepared according to the general procedure described in scheme 3 and using (R)-4-methoxy-6-(piperidin-3-ylmethyl)pyrimidine and N-(4-fluoro-5-formylthiazol-2-yl)propionamide. LCMS (ESI): [M+H] 394. ¹HNMR: (400 MHz, Methanol-d₄) δ 8.61 (d, J=1.00 Hz, 1H), 6.72 (d, J=1.00 Hz, 1H), 3.97 (s, 3H), 3.60 (s, 2H), 2.70-2.91 (m, 2H), 2.51-2.67 (m, 2H), 2.39-2.52 (m, 2H), 2.00-2.23 (m, 2H), 1.82-1.97 (m, 1H), 1.44-1.77 (m, 3H), 1.19 (t, J=7.53 Hz, 3H), 0.89-1.09 (m, 1H).

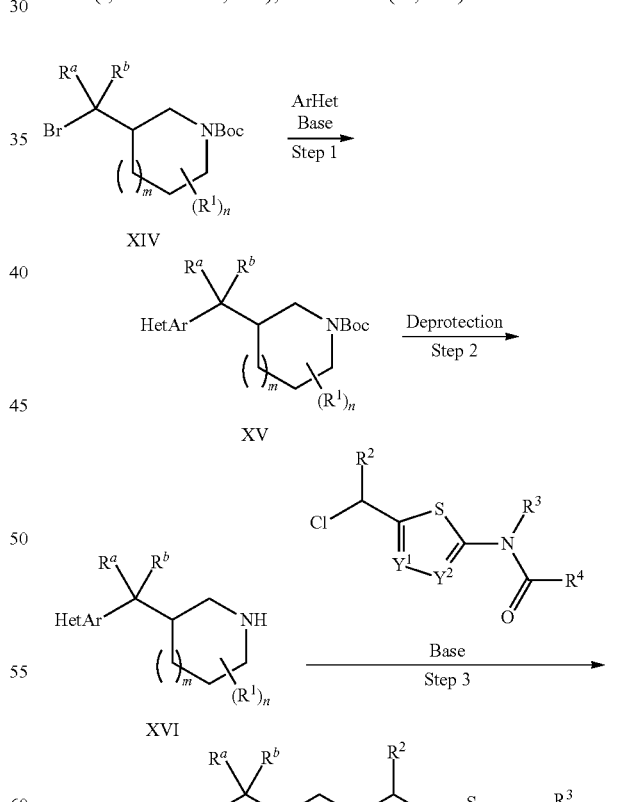

Intermediate 18

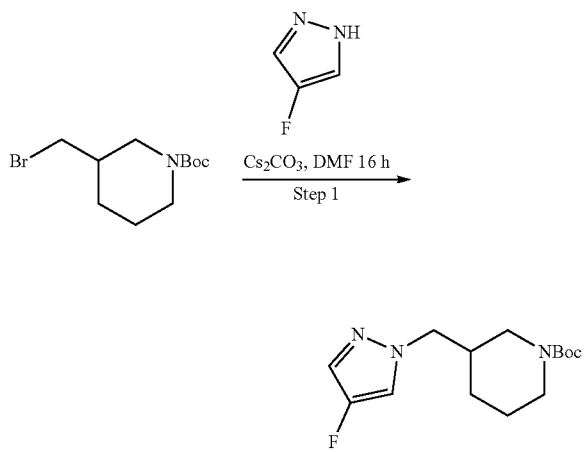

tert-butyl 3-((4-fluoro-1H-pyrazol-1-yl)methyl)piperidine-1-carboxylate

4-Fluoro-1H-pyrazole (0.10 g, 1.16 mmol), cesium carbonate (1.14 g, 3.50 mmol), and tert-butyl 3-(bromomethyl)piperidine-1-carboxylate (0.323 g, 1.16 mmol) were suspended in DMF (5.00 mL) and the mixture was heated to 100° C. for 16 h. The reaction mixture cooled to room temperature, filtered, and concentrated in vacuo to afford the title compound as a crude mixture. LCMS (ESI): [M+H] 284.

Intermediate 19

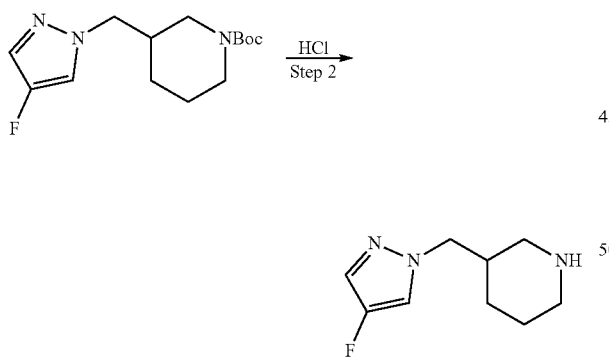

3-((4-fluoro-1H-pyrazol-1-yl)methyl)piperidine hydrochloride

A solution of HCl in dioxane (4.0 M, 4.76 mL, 27.0 mmol) was added to the crude mixture of tert-butyl 3-((4-fluoro-1H-pyrazol-1-yl)methyl)piperidine-1-carboxylate from the previous step and the mixture was stirred for 4 h at room temperature. The mixture was concentrated in vacuo to afford the title compound as a crude mixture. LCMS (ESI): [M+H] 184.

Example 4-1

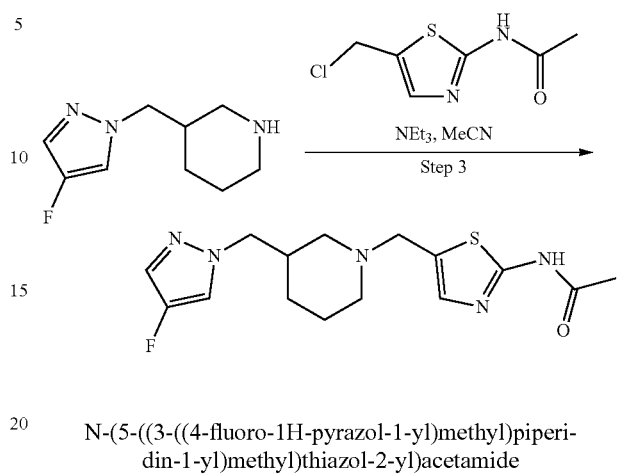

N-(5-((3-((4-fluoro-1H-pyrazol-1-yl)methyl)piperidin-1-yl)methyl)thiazol-2-yl)acetamide A crude mixture of 3-((4-fluoro-1H-pyrazol-1-yl)methyl)piperidine hydrochloride from the previous step was dissolved in MeCN (4.00 mL). To the mixture was added triethylamine (0.46 g, 4.56 mmol, 0.63 mL) and N-[5-(chloromethyl)thiazol-2-yl]acetamide (0.145 mg, 0.760 mmol). The mixture was stirred for 16 h at room temperature. The reaction mixture was filtered and concentrated in vacuo. The residue was purified by Prep-HPLC {(Column: Waters Sunfire OBD 50×100 mm, 5 um; conditions: 95% water/5% ACN 20 minutes in 0.1% TFA (flow rate: 80 mL/min))} to afford the title compound. LCMS (ESI): [M+H] 338. HNMR: (500 MHz, Methanol-d4) δ 7.58 (d, J=4.6 Hz, 1H), 7.32-7.34 (m, 1H), 7.21 (s, 1H), 3.96 (d, J=7.3 Hz, 2H), 3.68 (s, 2H), 2.78 (br d, J=11.0 Hz, 1H), 2.64 (br d, J=9.8 Hz, 1H), 2.12-2.21 (m, 5H), 1.90 (br t, J=10.4 Hz, 1H), 1.69-1.77 (m, 1H), 1.52-1.64 (m, 2H), 1.01-1.10 (m, 1H).

Example 4-2

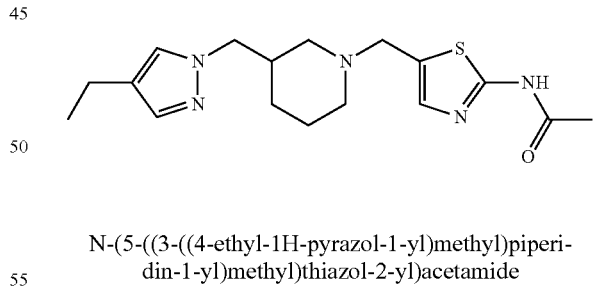

N-(5-((3-((4-ethyl-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-ethyl-1H-pyrazole, and N-[5-(chloromethyl)thiazol-2-yl]acetamide. LCMS (ESI): [M+H] 348. $^1$HNMR: (500 MHz, Methanol-d4) δ 7.55 (s, 1H), 7.41 (s, 1H), 7.32-7.36 (m, 1H), 4.52 (q, J=14.4 Hz, 2H), 4.13 (br dd, J=14.0, 5.5 Hz, 1H), 4.02 (br dd, J=14.0, 7.9 Hz, 1H), 3.53 (br d, J=12.2 Hz, 1H), 3.22 (br d, J=11.6 Hz, 1H), 2.82-2.95 (m, 1H), 2.73 (br t, J=12.2 Hz, 1H), 2.44-2.50 (m, 2H), 2.30 (br s, 1H), 2.22-2.24 (m, 3H), 1.92-2.10 (m, 1H), 1.68-1.87 (m, 2H), 1.14-1.19 (t, 3H).

Example 4-3

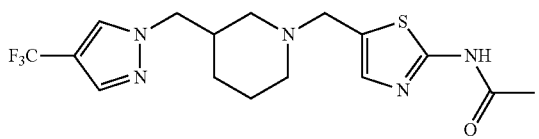 [SMILES: CC(=O)Nc1ncc(CN2CCCC(Cn3cc(C(F)(F)F)cn3)C2)s1]

N-(5-((3-((4-(trifluoromethyl)-1H-pyrazol-1-yl)
methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-(trifluoromethyl)-1H-pyrazole, and N-[5-(chloromethyl)thiazol-2-yl]acetamide. LCMS (ESI): [M+H] 388.

Example 4-4

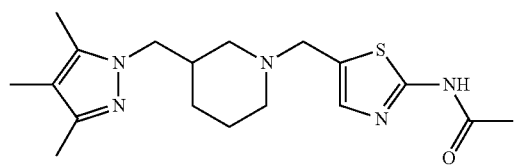 [SMILES: CC(=O)Nc1ncc(CN2CCCC(Cn3nc(C)c(C)c3C)C2)s1]

N-(5-((3-((3,4,5-trimethyl-1H-pyrazol-1-yl)methyl)
piperidin-1-yl)methyl)thiazol-2-yl)acetamide The title compound was prepared in an analogous manner of that in scheme 4 from tert-butyl 3-(bromomethyl)piperidine-1-carboxylate, 3,4,5-trimethyl-1H-pyrazole, and N-[5-(chloromethyl)thiazol-2-yl]acetamide. LCMS (ESI): [M+H] 363.

Example 4-5

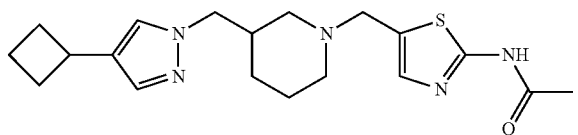 [SMILES: CC(=O)Nc1ncc(CN2CCCC(Cn3cc(C4CCC4)cn3)C2)s1]

N-(5-((3-((4-cyclobutyl-1H-pyrazol-1-yl)methyl)
piperidin-1-yl)methyl)thiazol-2-yl)acetamide The title compound was prepared in an analogous manner of that in scheme 4 from tert-butyl 3-(bromomethyl)piperidine-1-carboxylate, 4-cyclobutyl-1H-pyrazole, and N-[5-(chloromethyl)thiazol-2-yl]acetamide. LCMS (ESI): [M+H] 375. $^1$HNMR: (500 MHz, Methanol-d4) δ 7.38 (s, 1H), 7.29 (s, 1H), 7.19 (s, 1H), 3.94-4.02 (m, 2H), 3.60-3.68 (m, 2H), 3.32-3.39 (m, 1H), 2.76 (br d, J=10.4 Hz, 1H), 2.57 (br d, J=10.4 Hz, 1H), 2.23-2.34 (m, 2H), 2.19 (s, 3H), 2.12-2.16 (m, 2H), 1.91-2.02 (m, 3H), 1.81-1.90 (m, 2H), 1.73 (dt, J=12.8, 4.0 Hz, 1H), 1.52-1.65 (m, 2H), 1.06 (br d, J=11.0 Hz, 1H).

Example 4-6

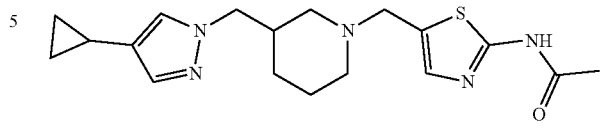

N-(5-((3-((4-cyclopropyl-1H-pyrazol-1-yl)methyl)
piperidin-1-yl)methyl)thiazol-2-yl)acetamide The title compound was prepared in an analogous manner of that in scheme 4 from tert-butyl 3-(bromomethyl)piperidine-1-carboxylate, 4-cyclopropyl-1H-pyrazole, and N-[5-(chloromethyl)thiazol-2-yl]acetamide. LCMS (ESI): [M+H] 360.

Example 4-7

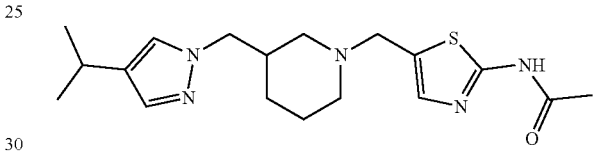

N-(5-((3-((4-isopropyl-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-isopropyl-1H-pyrazole, and N-[5-(chloromethyl)thiazol-2-yl]acetamide. LCMS (ESI): [M+H] 363. $^1$HNMR: (500 MHz, Methanol-d4) δ 7.30 (s, 1H), 7.22 (s, 1H), 7.19 (s, 1H), 3.91-4.00 (m, 2H), 3.61-3.67 (m, 2H), 2.75 (br d, J=10.4 Hz, 1H), 2.56 (br d, J=9.8 Hz, 1H), 2.20 (s, 3H), 2.10-2.12 (m, 2H), 1.84 (br t, J=10.1 Hz, 1H), 1.52-1.74 (m, 4H), 1.05 (br d, J=11.0 Hz, 1H), 0.78-0.83 (m, 2H), 0.41-0.46 (m, 2H).

Example 4-8

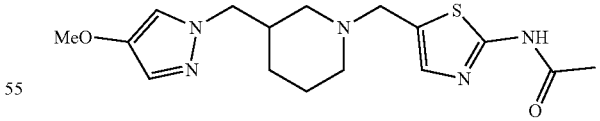

N-(5-((3-((4-methoxy-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-methoxy-1H-pyrazole, and N-[5-(chloromethyl)thiazol-2-yl]acetamide. LCMS (ESI): [M+H] 350.

Example 4-9

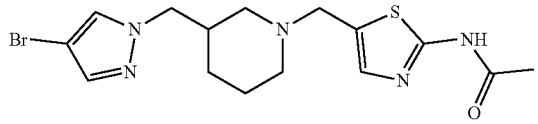 [SMILES: CC(=O)Nc1ncc(CN2CCCC(Cn3cc(Br)cn3)C2)s1]

N-(5-((3-((4-bromo-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-bromo-1H-pyrazole, and N-[5-(chloromethyl)thiazol-2-yl]acetamide. LCMS (ESI): [M+H] 399.

Example 4-10

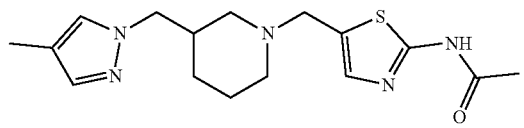 [SMILES: CC(=O)Nc1ncc(CN2CCCC(Cn3cc(C)cn3)C2)s1]

N-(5-((3-((4-methyl-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 4-methyl-1H-pyrazole, and N-[5-(chloromethyl)thiazol-2-yl]acetamide. LCMS (ESI): [M+H] 334.

Example 4-11

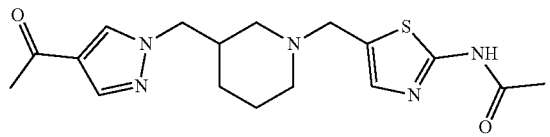 [SMILES: CC(=O)Nc1ncc(CN2CCCC(Cn3cc(C(C)=O)cn3)C2)s1]

N-(5-((3-((4-acetyl-1H-pyrazol-1-yl)methyl)piperidin-1-yl)methyl)thiazol-2-yl)acetamide The title compound was prepared in an analogous manner of that in scheme 4 from tert-butyl 3-(bromomethyl)piperidine-1-carboxylate, 1-(1H-pyrazol-4-yl)ethan-1-one, and N-[5-(chloromethyl)thiazol-2-yl]acetamide. LCMS (ESI): [M+H] 362.

Intermediate A

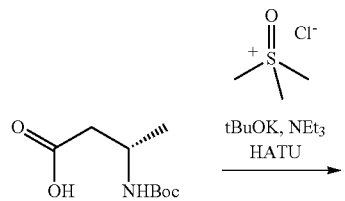

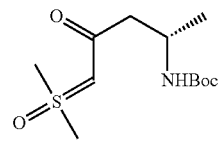

t-butyl (S)-(5-(dimethyl(oxo)-l6-sulfanylidene)-4-oxopentan-2-yl)carbamate

A suspension (S)-3-((tert-butoxycarbonyl)amino)butanoic acid (19 g, 93.5 mmol) and HATU (38.4 g, 101 mmol) in THF (370 mL) was treated with TEA (55 mL, 390 mmol) and the resulting solution was stirred at rt for 16 h. In another flask a suspension of potassium tert-butoxide (37.8 g, 337 mmol) and trimethylsulfoxonium chloride (43.3 g, 337 mmol) in THF (370 mL) was heated at 60° C. for 2 h, and then cooled in an ice-water bath during 15 min. The solution of activated ester was then added drop-wise at 0° C. over a period of 45 min. The reaction mixture was further stirred for 1 h, after which the reaction was concentrated under reduced pressure. The residue was partitioned between dichloromethane (1000 mL) and water (1000 mL). After separating the layers, the organic phase was washed with saturated aqueous NaCl (1000 mL), dried over $Na_2SO_4$, filtered, and concentrated under reduced pressure. The crude material was purified on silica gel column chromatography using a gradient of 0-5% MeOH in dichloromethane to afford the title compound (14 g, 56% yield).

Intermediate B

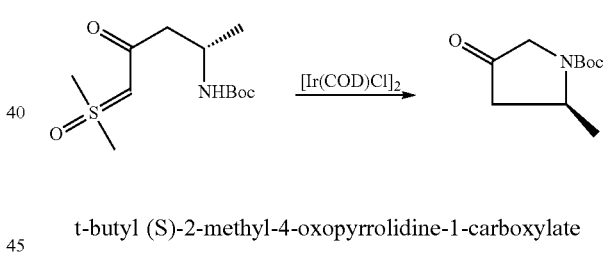

t-butyl (S)-2-methyl-4-oxopyrrolidine-1-carboxylate tert-Butyl (S)-(5-(dimethyl(oxo)-l6-sulfanylidene)-4-oxopentan-2-yl)carbamate (14 g, 50.5 mmol) was dissolved in 1,2-dichloroethane (500 mL). After deaeration, di-µ-chlorobis-[(f-cycloocta-1,5-diene)]diiridium (I) (1 g) was added under an argon atmosphere followed by raising the temperature and allowing to react at 70° C. for 2 h. The solvent of the reaction mixture was distilled off under reduced pressure, and the resulting residue was subjected to silica gel column chromatography (hexane:ethyl acetate=2:1) to afford the title compound (6.12 g, 62% yield).

Intermediate C

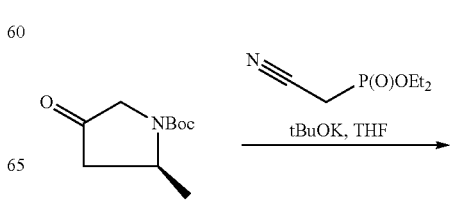

-continued

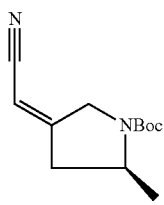

t-butyl (S)-4-(cyanomethylene)-2-methylpyrrolidine-1-carboxylate

A solution of diethyl cyanomethylphosphonate (5.5 g, 31 mmol) in anhydrous tetrahydrofuran (100 mL) was degassed with nitrogen. Subsequently, potassium tert-butoxide (3.5 g, 31 mmol) was added at room temperature, and the reaction mixture was degassed with nitrogen and stirred for 20 minutes. tert-butyl (S)-2-methyl-4-oxopyrrolidine-1-carboxylate (6.12 g, 31 mmol) in anhydrous tetrahydrofuran (20 mL) was added. After stirring for 20 hours, the reaction mixture was concentrated affording brown oil. The residue was suspended in chloroform (500 mL), washed with saturated NaHCO$_3$ (3×250 mL), dried over Na$_2$SO$_4$, and concentrated in vacuo to afford the title compound (5.16 g, 75% yield) as a brown oil.

Intermediate D

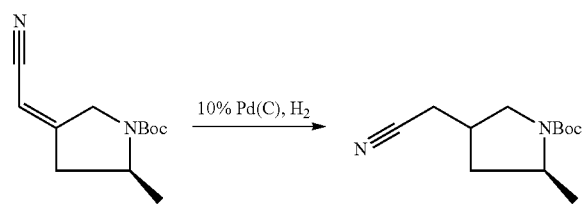 [SMILES: C[C@H]1C/C(=C/C#N)CN1C(=O)OC(C)(C)C ; C[C@H]1CC(CC#N)CN1C(=O)OC(C)(C)C]

t-butyl (2S)-4-(cyanomethyl)-2-methylpyrrolidine-1-carboxylate

A solution of the t-butyl (S)-4-(cyanomethylene)-2-methylpyrrolidine-1-carboxylate (5.16 g, 23 mmol) in methanol (500 mL) containing 10% Pd on carbon (2 g) was stirred under hydrogen at 60 psi for 24 h. The suspension was filtered through celite, concentrated in vacuo, and the residue was purified by silica gel chromatography, eluting with 15% EtOAc-hexane to provide the title compound (4.43 g, 86% yield).

Intermediate E

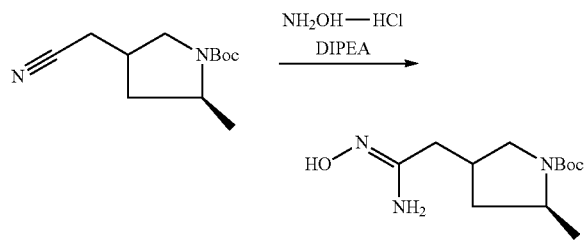

t-butyl (2S)-4-((Z)-2-amino-2-(hydroxyimino)ethyl)-2-methylpyrrolidine-1-carboxylate A mixture of t-butyl (2S)-4-(cyanomethyl)-2-methylpyrrolidine-1-carboxylate (4.43 g, 20 mmol) and hydroxylamine hydrochloride (2.76 g, 40 mmol) was dissolved in EtOH (100 mL) to give a colorless suspension. Then DIPEA (5 g, 47 mmol) was added and the resulting mixture was stirred at 100° C. for 6 h. The crude reaction mixture was concentrated in vacuo and washed with hexane (50 mL) to afford the title compound (3.96 g, 77% yield).

Intermediate F

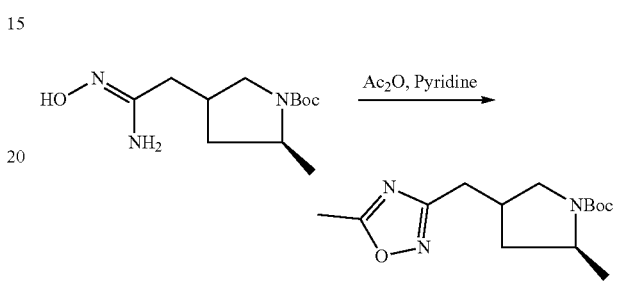

t-butyl (2S)-2-methyl-4-((5-methyl-1,2,4-oxadiazol-3-yl)methyl)pyrrolidine-1-carboxylate t-Butyl (2S)-4-((Z)-2-amino-2-(hydroxyimino)ethyl)-2-methylpyrrolidine-1-carboxylate (3.96 g, 15.4 mmol) was dissolved in pyridine (50 mL) was added acetic anhydride (1.5 g, 15 mmol) and then it was heated at 90° C. for 24 h. The residue was partitioned between dichloromethane (1000 mL) and water (1000 mL). After separating the layers, the organic phase was washed with saturated aqueous NaCl (1000 mL), dried over Na$_2$SO$_4$, filtered, concentrated under reduced pressure. The obtained residue was subjected to column chromatography on silica gel as eluent DCM:MeOH to give the title compound (0.65 g, 17% yield).

Intermediate G

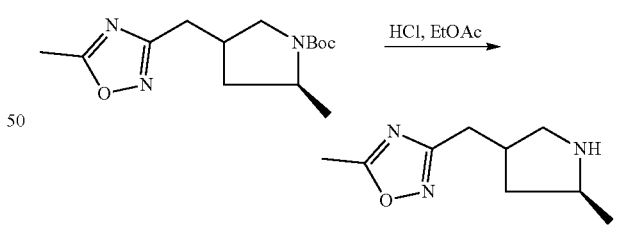

5-methyl-3-(((5S)-5-methylpyrrolidin-3-yl)methyl)-1,2,4-oxadiazole

To a solution of tert-butyl (2S)-2-methyl-4-((5-methyl-1,2,4-oxadiazol-3-yl)methyl)pyrrolidine-1-carboxylate (0.65 g, 2.3 mmol) in EtOAc (20 mL), 18M HCl in EtOAc (10 mL) was added dropwise. After stirring for 4 h at room temperature, the formed precipitate was collected by filtration, washed with EtOAc (20 mL), and dried in high vacuum to afford the title compound (0.305 g, 61% yield). LC-MS (ESI) m/z [M+H]$^+$ 182. $^1$H NMR (400 MHz, d$_2$o) δ 1.25 (dd, J=6.6, 3.2 Hz, 1.5H), 1.29* (dd, J=6.4, 3.1 Hz, 1.5H), 1.35 (m, 0.5H), 1.85 (m, 1H), 2.28* (m, 0.5H), 2.47 (s, 3H), 2.80 (m, 3H), 2.94 (m, 1H), 3.45 (m, 1H), 3.61 (m, 0.5H), 3.76* (m, 0.5H)

Example 4-12

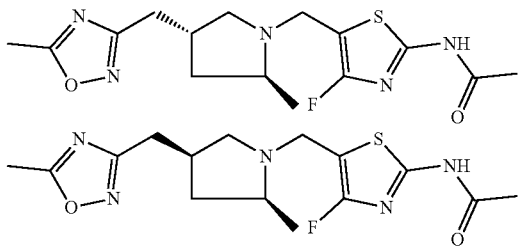

N-(4-fluoro-5-(((2S,4R)-2-methyl-4-((5-methyl-1,2,4-oxadiazol-3-yl)methyl)pyrrolidin-1-yl)methyl)thiazol-2-yl)acetamide and N-(4-fluoro-5-(((2S,4S)-2-methyl-4-((5-methyl-1,2,4-oxadiazol-3-yl)methyl)pyrrolidin-1-yl)methyl)thiazol-2-yl)acetamide The title compound was prepared according to the general procedure described in example 1-1 and using 5-methyl-3-(((5S)-5-methylpyrrolidin-3-yl)methyl)-1,2,4-oxadiazole and N-(4-fluoro-5-formylthiazol-2-yl)acetamide. The resulting isomers were purified over SiO$_2$ (ethyl acetate 100%) to afford two isomers (trans or cis), which were assigned arbitrarily as:
Peak 1: LCMS (ESI): [M+H] 354. $^1$HNMR: (400 MHz, Methanol-d$_4$) δ 3.91 (dd, J=1.13, 14.43 Hz, 1H), 3.52 (d, J=14.31 Hz, 1H), 2.83 (dd, J=3.26, 9.54 Hz, 1H), 2.70-2.78 (m, 2H), 2.54 (s, 3H), 2.43-2.59 (m, 3H), 2.18 (s, 3H), 2.09-2.24 (m, 1H), 1.19-1.27 (m, 1H), 1.17 (d, J=6.27 Hz, 3H)
Peak 2: LCMS (ESI): [M+H] 354. $^1$HNMR: (400 MHz, Methanol-d$_4$) δ 3.86-3.96 (m, 1H), 3.54 (d, J=14.56 Hz, 1H), 3.11-3.21 (m, 1H), 2.67-2.73 (m, 2H), 2.54-2.66 (m, 2H), 2.53 (s, 3H), 2.18 (s, 3H), 2.12 (t, J=9.16 Hz, 1H), 1.59-1.82 (m, 2H), 1.15 (d, J=6.27 Hz, 3H).

Examples 4-13 and 4-14

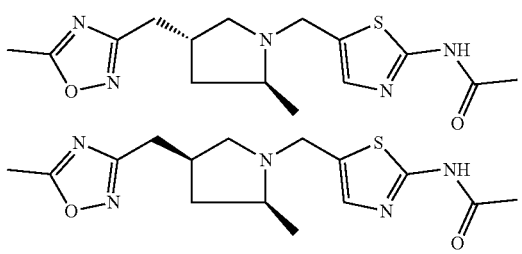

N-(5-(((2S,4R)-2-methyl-4-((5-methyl-1,2,4-oxadiazol-3-yl)methyl)pyrrolidin-1-yl)methyl)thiazol-2-yl)acetamide and N-(5-(((2S,4S)-2-methyl-4-((5-methyl-1,2,4-oxadiazol-3-yl)methyl)pyrrolidin-1-yl)methyl)thiazol-2-yl)acetamide The title compound was prepared according to the general procedure described in example 1-2 and using 5-Methyl-3-(((5S)-5-methylpyrrolidin-3-yl)methyl)-1,2,4-oxadiazole. The resulting isomers were purified over SiO$_2$ (EtOAc/EtOH 3/1) to afford two isomers (trans or cis): N-(5-(((2S,4R)-2-methyl-4-((5-methyl-1,2,4-oxadiazol-3-yl)methyl)pyrrolidin-1-yl)methyl)thiazol-2-yl)acetamide (early fractions): LCMS (ESI): [M+H] 336. $^1$HNMR: (400 MHz, Methanol-d$_4$) δ 7.23 (s, 1H), 4.07 (dd, J=0.88, 14.18 Hz, 1H), 3.47-3.57 (m, 1H), 2.72-2.84 (m, 3H), 2.41-2.61 (m, 3H), 2.53 (s, 3H), 2.10-2.24 (m, 1H), 2.19 (s, 3H), 1.20-1.32 (m, 1H), 1.17 (d, J=6.02 Hz, 3H).

N-(5-(((2S,4S)-2-methyl-4-((5-methyl-1,2,4-oxadiazol-3-yl)methyl)pyrrolidin-1-yl)methyl)thiazol-2-yl)acetamide (Later Fractions)

LCMS (ESI): [M+H] 336. $^1$HNMR: (400 MHz, Methanol-d$_4$) δ 7.24 (s, 1H), 4.07 (dd, J=0.88, 14.18 Hz, 1H), 3.56 (d, J=14.31 Hz, 1H), 3.13 (dd, J=7.03, 9.29 Hz, 1H), 2.53-2.72 (m, 4H), 2.53 (s, 3H), 2.19 (s, 3H), 2.08 (t, J=9.29 Hz, 1H), 1.63-1.83 (m, 2H), 1.15 (d, J=6.02 Hz, 3H).

Examples 4-15 and 4-16

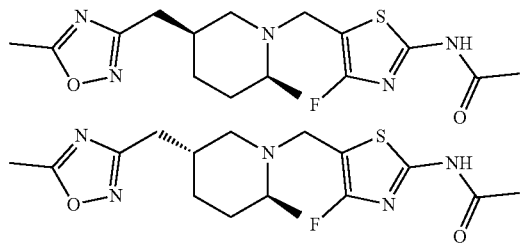

N-(4-fluoro-5-(((2S,5S)-2-methyl-5-((5-methyl-1,2,4-oxadiazol-3-yl)methyl)piperidin-1-yl)methyl)thiazol-2-yl)acetamide and N-(4-fluoro-5-(((2S,5R)-2-methyl-5-((5-methyl-1,2,4-oxadiazol-3-yl)methyl)piperidin-1-yl)methyl)thiazol-2-yl)acetamide The title compound was prepared according to the general procedure described in example 1-1 and using 5-methyl-3-(((6S)-6-methylpiperidin-3-yl)methyl)-1,2,4-oxadiazole and N-(4-fluoro-5-formylthiazol-2-yl)acetamide. The resulting isomers were purified over SiO$_2$ (EtOAc 100%) to afford two isomers (cis and trans):

N-(4-fluoro-5-(((2S,5S)-2-methyl-5-((5-methyl-1,2,4-oxadiazol-3-yl)methyl)piperidin-1-yl)methyl)thiazol-2-yl)acetamide (Early Fractions)

LCMS (ESI): [M+H] 368. $^1$HNMR: (400 MHz, Methanol-d$_4$) δ 3.59-3.81 (m, 2H), 2.68-2.76 (m, 3H), 2.43-2.60 (m, 2H), 2.53 (s, 3H), 2.18 (s, 3H), 2.04-2.13 (m, 1H), 1.60-1.75 (m, 1H), 1.49-1.58 (m, 2H), 1.35-1.47 (m, 1H), 1.11 (d, J=6.27 Hz, 3H).

N-(4-fluoro-5-(((2S,5R)-2-methyl-5-((5-methyl-1,2,4-oxadiazol-3-yl)methyl)piperidin-1-yl)methyl)thiazol-2-yl)acetamide (Later Fractions)

LCMS (ESI): [M+H] 368. $^1$HNMR: (400 MHz, Methanol-d$_4$) δ 3.73-3.96 (m, 2H), 2.90-2.95 (m, 1H), 2.51-2.60 (m, 2H), 2.54 (s, 3H), 2.23-2.34 (m, 1H), 2.19 (s, 3H), 1.96-2.07 (m, 2H), 1.64-1.80 (m, 2H), 1.26-1.42 (m, 1H), 1.20 (d, J=6.27 Hz, 3H), 0.95-1.14 (m, 1H).

Example 4-17

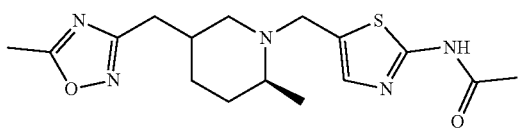 [SMILES: CC(=O)Nc1ncc(CN2CC(Cc3noc(C)n3)CC[C@@H]2C)s1]

N-(5-(((2S)-2-methyl-5-((5-methyl-1,2,4-oxadiazol-3-yl)methyl)piperidin-1-yl)methyl)thiazol-2-yl)acetamide The title compound was prepared according to the general procedure described in example 1-2 and using 5-methyl-3-(((6S)-6-methylpiperidin-3-yl)methyl)-1,2,4-oxadiazole. LCMS (ESI): [M+H] 350. $^1$H NMR (400 MHz, Methanol-d$_4$) δ 7.24 (s, 1H), 3.96-4.07 (m, 1H), 3.77-3.90 (m, 1H), 2.87-2.96 (m, 1H), 2.51-2.58 (m, 2H), 2.53 (s, 3H), 2.23-2.32 (m, 1H), 2.20 (s, 3H), 1.98-2.11 (m, 1H), 1.89-1.96 (m, 1H), 1.64-1.79 (m, 2H), 1.29-1.43 (m, 1H), 1.22 (d, J=6.02 Hz, 3H), 0.93-1.10 (m, 1H).

Example 4-18

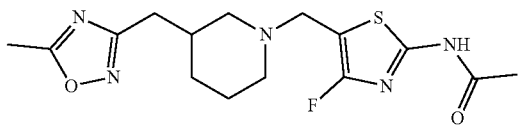

N-(4-fluoro-5-((3-((5-methyl-1,2,4-oxadiazol-3-yl)methyl)piperidin-1-yl)methyl)thiazol-2-yl)acetamide The title compound was prepared according to the general procedure described in example 1-1 and using 5-methyl-3-(piperidin-3-ylmethyl)-1,2,4-oxadiazole and N-(4-fluoro-5-formylthiazol-2-yl)acetamide. LCMS (ESI): [M+H] 354. $^1$HNMR: (400 MHz, METHANOL-d$_4$) δ 3.64 (s, 2H), 2.78-2.95 (m, 2H), 2.62 (d, J=7.28 Hz, 2H), 2.54 (s, 3H), 2.18 (s, 3H), 2.03-2.16 (m, 2H), 1.89-2.00 (m, 1H), 1.67-1.79 (m, 2H), 1.50-1.65 (m, 1H), 0.95-1.14 (m, 1H).

Example 4-19

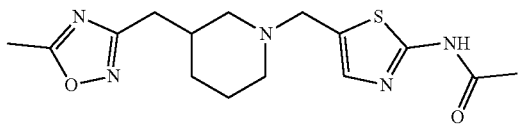

N-(5-((3-((5-methyl-1,2,4-oxadiazol-3-yl)methyl)piperidin-1-yl)methyl)thiazol-2-yl)acetamide The title compound was prepared according to the general procedure described in example 1-1 and using 5-methyl-3-(piperidin-3-ylmethyl)-1,2,4-oxadiazoleoxadiazole. LCMS (ESI): [M+H] 336. $^1$HNMR: (400 MHz, DMSO-d$_6$) δ 11.80 (s, 1H), 7.09 (s, 1H), 3.58 (q, J=13.9 Hz, 2H), 2.81-2.73 (m, 1H), 2.74-2.66 (m, 1H), 2.57-2.52 (m, 5H), 2.11 (s, 3H), 1.99 (s, 2H), 1.85 (t, J=10.2 Hz, 1H), 1.66 (t, J=14.0 Hz, 2H), 1.50 (d, J=12.1 Hz, 1H), 1.02 (t, J=11.7 Hz, 1H).

Example 4-20

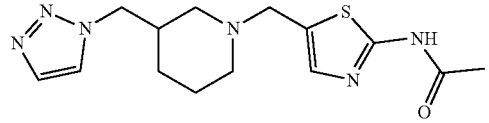 [SMILES: CC(=O)Nc1ncc(CN2CCCC(Cn3ccnn3)C2)s1]

N-(5-((3-((1H-1,2,3-triazol-1-yl)methyl)piperidin-1-yl)methyl)thiazol-2-yl)acetamide The title compound was prepared according to the general procedure described in example 1-1 and using 3-((1H-1,2,3-triazol-1-yl)methyl)piperidine. LCMS (ESI): [M+H] 321.

Example 4-21

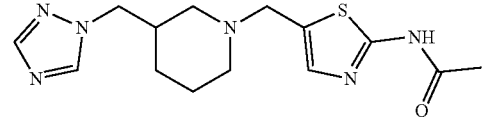 [SMILES: CC(=O)Nc1ncc(CN2CCCC(Cn3cncn3)C2)s1]

N-(5-((3-((1H-1,2,4-triazol-1-yl)methyl)piperidin-1-yl)methyl)thiazol-2-yl)acetamide The title compound was prepared according to the general procedure described in example 1-1 and using 3-((1H-1,2,4-triazol-1-yl)methyl)piperidine. LCMS (ESI): [M+H] 321. $^1$HNMR: (400 MHz, Chloroform-d) δ 12.25 (s, 1H), 8.01 (s, 1H), 7.91 (s, 1H), 7.15 (s, 1H), 4.18 (dd, J=13.7, 7.5 Hz, 1H), 4.09 (dd, J=13.7, 6.8 Hz, 1H), 3.69-3.53 (m, 2H), 2.66-2.48 (m, 2H), 2.35-2.16 (m, 4H), 2.03 (t, J=9.6 Hz, 1H), 1.73-1.64 (m, 1H), 1.64-1.49 (m, 2H), 1.22-1.07 (m, 2H).

Example 4-22

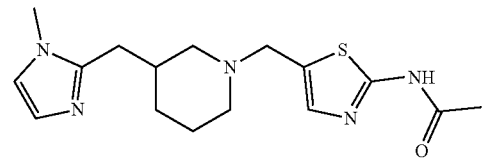 [SMILES: CC(=O)Nc1ncc(CN2CCCC(Cc3nccn3C)C2)s1]

N-(5-((3-((1-methyl-1H-imidazol-2-yl)methyl)piperidin-1-yl)methyl)thiazol-2-yl)acetamide The title compound was prepared according to the general procedure described in example 1-1 and using 3-((1-methyl-1H-imidazol-2-yl)methyl)piperidine. LCMS (ESI): [M+H]

334. ¹HNMR: (400 MHz, Chloroform-d) δ 12.48 (s, 1H), 7.15 (s, 1H), 6.94-6.85 (m, 1H), 6.81-6.72 (m, 1H), 3.71-3.58 (m, 2H), 3.57 (s, 3H), 2.83-2.50 (m, 4H), 2.29 (s, 3H), 2.14-2.00 (m, 2H), 1.94 (t, J=10.0 Hz, 1H), 1.76-1.58 (m, 2H), 1.59-1.43 (m, 1H), 1.12-1.00 (m, 1H).

Example 4-23

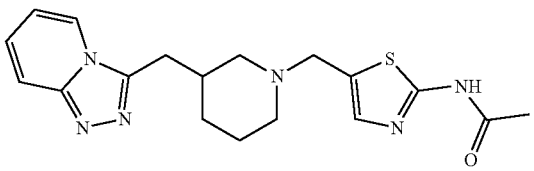 [SMILES: CC(=O)Nc1ncc(CN2CCCC(Cc3nnc4ccccn34)C2)s1]

N-(5-((3-([1,2,4]triazolo[4,3-a]pyridin-3-ylmethyl)piperidin-1-yl)methyl)thiazol-2-yl)acetamide The title compound was prepared according to the general procedure described in example 1-1 and using 3-(piperidin-3-ylmethyl)-[1,2,4]triazolo[4,3-a]pyridine. LCMS (ESI): [M+H] 371. ¹HNMR: (400 MHz, DMSO-d₆) δ 11.82 (s, 1H), 8.35 (d, J=7.0 Hz, 1H), 7.62 (d, J=9.3 Hz, 1H), 7.25 (dd, J=9.2, 6.5 Hz, 1H), 7.09 (s, 1H), 6.87 (t, J=6.7 Hz, 1H), 3.65-3.51 (m, 2H), 3.14-3.01 (m, 2H), 2.79 (d, J=10.7 Hz, 1H), 2.66 (d, J=10.6 Hz, 1H), 2.26-2.15 (m, 1H), 2.11 (s, 3H), 2.10-2.03 (m, 1H), 1.98 (t, J=10.0 Hz, 1H), 1.76-1.56 (m, 2H), 1.59-1.42 (m, 1H), 1.13 (d, J=10.5 Hz, 1H).

Example 4-24

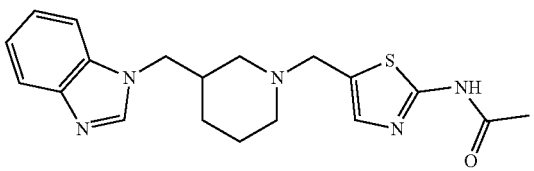 [SMILES: CC(=O)Nc1ncc(CN2CCCC(Cn3cnc4ccccc43)C2)s1]

N-(5-((3-((1H-benzo[d]imidazol-1-yl)methyl)piperidin-1-yl)methyl)thiazol-2-yl)acetamide The title compound was prepared according to the general procedure described in example 1-1 and using 1-(piperidin-3-ylmethyl)-1H-benzo[d]imidazole. LCMS (ESI): [M+H] 370. ¹HNMR: (400 MHz, Chloroform-d) δ 12.28 (s, 1H), 7.84 (s, 1H), 7.78 (d, J=7.1 Hz, 1H), 7.39 (d, J=7.8 Hz, 1H), 7.33-7.19 (m, 2H), 7.14 (s, 1H), 4.19 (dd, J=14.3, 7.7 Hz, 1H), 4.05 (dd, J=14.3, 7.0 Hz, 1H), 3.61 (s, 2H), 3.47 (s, 3H), 2.69-2.42 (m, 1H), 2.29 (s, 2H), 2.27-2.14 (m, 1H), 2.10-1.93 (m, 1H), 1.75-1.62 (m, 1H), 1.59 (s, 1H), 1.56-1.40 (m, 1H), 1.22-1.07 (m, 1H).

Example 4-25

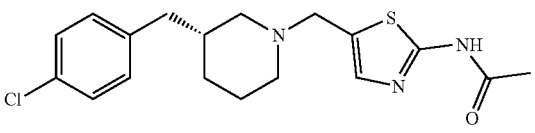 [SMILES: CC(=O)Nc1ncc(CN2CCC[C@H](Cc3ccc(Cl)cc3)C2)s1]

N-(5-((3-(4-chlorobenzyl)piperidin-1-yl)methyl)thiazol-2-yl)acetamide

The title compound was prepared according to the general procedure described in example 1-1 and using 3-(4-chlorobenzyl)piperidine. LCMS (ESI): [M+H] 364. ¹HNMR: (400 MHz, DMSO-d₆) δ 11.80 (s, 1H), 7.20 (d, J=8.0 Hz, 2H), 7.10 (d, J=8.2 Hz, 2H), 7.07 (s, 1H), 3.54 (q, J=13.8 Hz, 2H), 2.76-2.61 (m, 2H), 2.59-2.46 (m, 1H), 2.42 (dd, J=13.6, 6.4 Hz, 1H), 2.12 (s, 3H), 2.03-1.88 (m, 1H), 1.87-1.69 (m, 2H), 1.69-1.53 (m, 2H), 1.44 (dd, J=23.5, 11.1 Hz, 1H), 0.93 (dd, J=20.1, 8.6 Hz, 1H).

Example 4-26

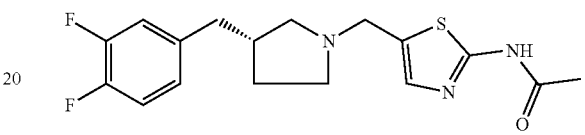

N-(5-((3-(3,4-difluorobenzyl)pyrrolidin-1-yl)methyl)thiazol-2-yl)acetamide

The title compound was prepared according to the general procedure described in example 1-1 and using 3-(3,4-difluorobenzyl)pyrrolidine. LCMS (ESI): [M+H] 352.

Biological Data

OGA Enzyme Inhibition Biochemical Assay

Recombinant full length human OGA enzyme was purchased from Origene. 4-MUGlCNAc substrate was purchased from Sigma. All other reagents were purchased from Sigma or Fisher. Assay buffer consists of the McIlvaine buffer system, pH 6.4 (0.2M $Na_2HPO_4$ mixed with 0.1M citric acid) and 0.01% BSA. Reactions consist of 1 nM OGA, 100 μM 4-MUGlcNAc ($K_m$), and compound in a final volume of 10 μl. Reactions were incubated for 90 minutes at room temperature and quenched with 40 μl of 3M glycine, pH 10 and read on a Perkin Elmer Envision plate reader (Ex: 355 nm/Em: 460 nm). Compounds were tested with a 10-point dose-response starting from 20 μM with a 4-fold dilution. Data was fit using GraphPad Prism using a 4-parameter fit with variable slope.

The following Table 1 shows the activity data for some of the compounds of the present invention.

|  | OGA $IC_{50}$ (nm) |
| --- | --- |
| Example 1-1 | 60 |
| Example 1-2 | 4 |
| Example 1-3 | 33 |
| Example 1-4 | 8 |
| Example 1-5 | 62 |
| Example 1-6 | 2 |
| Example 1-7 | 3 |
| Example 1-8 | 29 |
| Example 1-9 | 12 |
| Example 1-10 | 20 |
| Example 1-11 | 4 |
| Example 1-12 | 7 |
| Example 1-13 | 142 |
| Example 1-14 | 22 |
| Example 1-15 | 46 |
| Example 1-16 | 270 |
| Example 1-17 | 180 |
| Example 1-18 | 17 |

| | OGA IC$_{50}$ (nm) |
|---|---|
| Example 1-19 | 10 |
| Example 1-20 | 69 |
| Example 1-21 | 13 |
| Example 1-22 | 100 |
| Example 1-23 | 17 |
| Example 1-24 | 31 |
| Example 1-25 | 220 |
| Example 1-26 | 30 |
| Example 1-27 | 11 |
| Example 1-28 | 52 |
| Example 1-29 | 2 |
| Example 1-30 | 30 |
| Example 1-31 | 5 |
| Example 1-32 | 2 |
| Example 1-33 | 4 |
| Example 1-34 | 5 |
| Example 1-35 | 5 |
| Example 1-36 | 30 |
| Example 1-37 | 4 |
| Example 1-38 | 31 |
| Example 1-39 | 11 |
| Example 1-40 | 4 |
| Example 1-41 | 1 |
| Example 1-42 | 2 |
| Example 1-43 | 3 |
| Example 1-44 | 2 |
| Example 1-45 | 24 |
| Example 1-46 | 25 |
| Example 1-47 | 16 |
| Example 2-1 | 7 |
| Example 2-2 | 114 |
| Example 2-3 | 2 |
| Example 2-4 | 2 |
| Example 2-5 | 23 |
| Example 2-6 | 8 |
| Example 2-7 | 3 |
| Example 2-8 | 18 |
| Example 2-9 | 30 |
| Example 2-10 | 29 |
| Example 2-11 | 1 |
| Example 2-12 | 240 |
| Example 2-13 | 450 |
| Example 2-14 | 12 |
| Example 2-15 | 84 |
| Example 2-16 | 880 |
| Example 2-17 | 2 |
| Example 2-18 | 358 |
| Example 2-19 | 1 |
| Example 2-20 | 1 |
| Example 2-21 | 108 |
| Example 2-22 | 36 |
| Example 2-24 | 1100 |
| Example 2-25 | 5 |
| Example 2-26 | 990 |
| Example 2-27 | <1 |
| Example 2-29 | 1 |
| Example 2-30 | 32 |
| Example 2-31 | 4 |
| Example 2-32 | 330 |
| Example 2-33 | 122 |
| Example 2-34 | 450 |
| Example 2-35 | 1600 |
| Example 2-36 | 1 |
| Example 2-37 | 2 |
| Example 2-38 | 27 |
| Example 2-39 | 1 |
| Example 2-40 | 27 |
| Example 2-41 | 510 |
| Example 2-42 | 250 |
| Example 2-44 | >20000 |
| Example 2-45 | 130 |
| Example 2-46 | 3900 |
| Example 2-47 | 1200 |
| Example 2-49 | >20000 |
| Example 2-50 | 270 |
| Example 2-51 | 1 |
| Example 2-52 | 1.7 |
| Example 2-53 | 9.2 |
| Example 3-1 | 1 |
| Example 3-2 | 11 |
| Example 3-3 | 920 |
| Example 3-4 | <1 |
| Example 3-5 | 2 |
| Example 3-6 | 2 |
| Example 3-7 | 2 |
| Example 3-8 | 1 |
| Example 3-9 | <1 |
| Example 3-10 | 14 |
| Example 3-11 | 11 |
| Example 3-12 | 9 |
| Example 3-13 | 14 |
| Example 3-14 | 12 |
| Example 3-15 | 4 |
| Example 3-16 | 19 |
| Example 3-17 | 1.2 |
| Example 3-18 | <1 |
| Example 3-19 | <1 |
| Example 3-20 | <1 |
| Example 3-21 | <1 |
| Example 3-22 | <1 |
| Example 3-23 | 1.3 |
| Example 3-24 | <1 |
| Example 3-25 | <1 |
| Example 3-26 | 6.2 |
| Example 3-27 | 34 |
| Example 3-28 | 8.3 |
| Example 3-29 | 10 |
| Example 3-30 | 5.1 |
| Example 3-31 | 14 |
| Example 3-32 | 8.9 |
| Example 3-33 | 4.8 |
| Example 3-34 | 8 |
| Example 3-35 | 11 |
| Example 3-36 | 77 |
| Example 3-37 | 79 |
| Example 3-38 | 150 |
| Example 3-39 | 310 |
| Example 3-40 | 150 |
| Example 3-41 | <1 |
| Example 3-42 | <1 |
| Example 3-43 | 87 |
| Example 3-44 | <1 |
| Example 3-45 | 4.4 |
| Example 3-46 | <1 |
| Example 3-47 | 130 |
| Example 3-48 | <1 |
| Example 3-49 | 2.2 |
| Example 4-1 | 500 |
| Example 4-2 | 970 |
| Example 4-3 | 960 |
| Example 4-4 | 680 |
| Example 4-5 | 660 |
| Example 4-6 | 540 |
| Example 4-7 | 380 |
| Example 4-8 | 360 |
| Example 4-9 | 310 |
| Example 4-10 | 230 |
| Example 4-11 | 15 |
| Example 4-12 Peak 1 | <1 |
| Example 4-12 Peak 2 | <1 |
| Example 4-13 | 1.9 |
| Example 4-14 | 3.8 |
| Example 4-15 | 1.6 |
| Example 4-16 | <1 |
| Example 4-17 | <1 |
| Example 4-18 | 6.6 |
| Example 4-19 | 9.3 |
| Example 4-20 | 55 |
| Example 4-21 | 38 |
| Example 4-22 | 43 |
| Example 4-23 | 27 |
| Example 4-24 | 58 |

| | OGA IC$_{50}$ (nm) |
|---|---|
| Example 4-25 | 8.9 |
| Example 4-26 | 56 |

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A compound represented by the following structural formula:

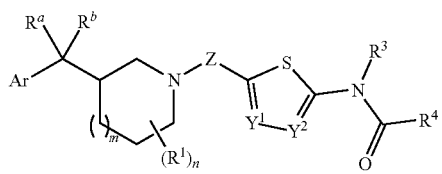
(I")

or a pharmaceutically acceptable salt thereof, wherein:
Ar is an optionally substituted 5- to 10-membered heteroaryl, an optionally substituted phenyl or an optionally substituted phenyl fused to an optionally substituted non-aromatic 5- to 6-membered heterocycle;
$Y^1$ and $Y^2$ are each $CR^c$ or N, wherein at least one of $Y^1$ or $Y^2$ is N;
Z is $CR^2R^2$, C(=O), $(CR^2R^2)_2$, $CH_2C$(=O), or C(=O)$CH_2$;
$R^a$, $R^b$ and $R^c$ are each independently —H, halo, $C_1$-$C_4$ alkyl, $C_1$-$C_4$ haloalkyl, or $C_1$-$C_4$ alkoxy, or $R^a$ and $R^b$ taken together with their intervening carbon atom form a $C_3$-$C_6$ cycloalkyl;
m is 0 or 1;
n is 0 or an integer from 1 to 7;
when n is other than 0, $R^1$, for each occurrence, is independently halo, $C_1$-$C_4$ alkyl, $C_1$-$C_4$ haloalkyl, $C_1$-$C_4$ alkoxy or $C_1$-$C_4$ haloalkoxy;
$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl;
or alternatively two $R^2$ together with the carbon atom to which they are attached form a $C_3$-$C_{10}$ cycloalkyl;
$R^3$ is —H or $C_1$-$C_4$ alkyl; and
$R^4$ is —H, $C_1$-$C_4$ alkyl, $C_1$-$C_4$ haloalkyl, or $C_3$-$C_6$ cycloalkyl;
or alternatively $R^3$ and $R^4$ taken together with their intervening atoms form an optionally substituted 5- to 7-membered heterocyclyl.

2. The compound according to claim 1, wherein the compound is represented by the following structural formula:

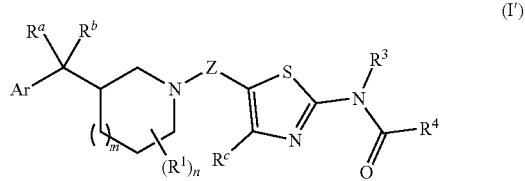
(I')

or a pharmaceutically acceptable salt thereof.

3. The compound according to claim 1, wherein the compound is represented by the following structural formula:
(i)

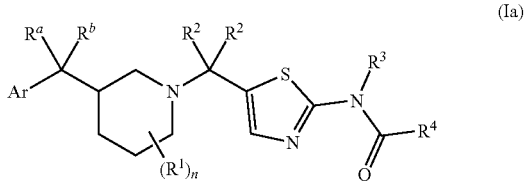
(Ia)

or a pharmaceutically acceptable salt thereof; wherein
$R^a$ and $R^b$ are each independently —H or $C_1$-$C_4$ alkyl; and
$R^2$, for each occurrence, is independently —H, halo, $C_1$-$C_4$ alkyl;
(ii)

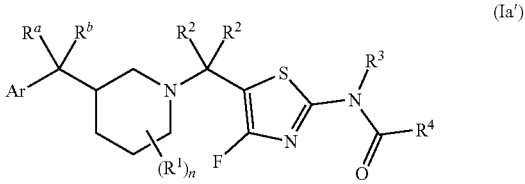
(Ia')

or a pharmaceutically acceptable salt thereof; wherein
$R^a$ and $R^b$ are each independently —H or $C_1$-$C_4$ alkyl; and
$R^2$, for each occurrence, is independently —H, halo, $C_1$-$C_4$ alkyl;
(iii)

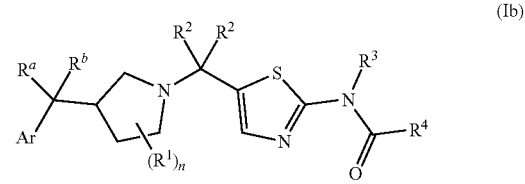
(Ib)

or a pharmaceutically acceptable salt thereof; wherein $R^2$, for each occurrence, is independently —H, halo, $C_1$-$C_4$ alkyl;

(iv)

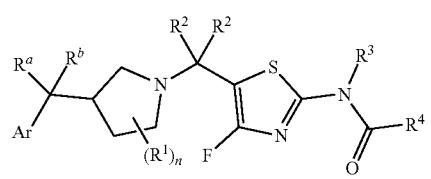
(Ib')

or a pharmaceutically acceptable salt thereof; wherein $R^2$, for each occurrence, is independently —H, halo, $C_1$-$C_4$ alkyl;

(v)

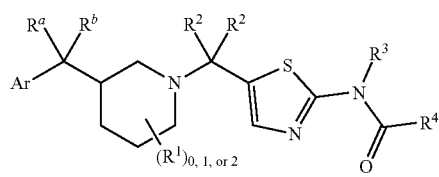
(Ia1)

or a pharmaceutically acceptable salt thereof; wherein
  $R^a$ and $R^b$ are each independently —H or methyl;
  $R^1$ is halo, $C_1$-$C_4$ alkyl or $C_1$-$C_4$ haloalkyl; and
  $R^2$, for each occurrence, is independently —H or $C_1$-$C_4$ alkyl;

(vi)

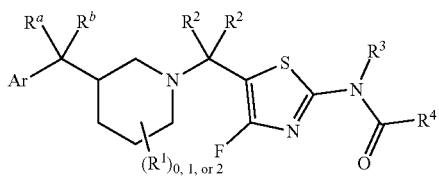
(Ia1')

or a pharmaceutically acceptable salt thereof; wherein
  $R^a$ and $R^b$ are each independently —H or methyl;
  $R^1$ is halo, $C_1$-$C_4$ alkyl or $C_1$-$C_4$ haloalkyl; and
  $R^2$, for each occurrence, is independently —H or $C_1$-$C_4$ alkyl;

(vii)

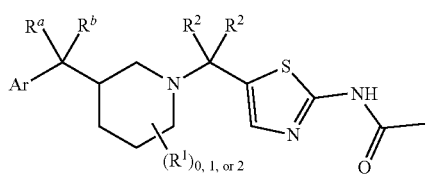
(Ia2)

or a pharmaceutically acceptable salt thereof; wherein
  $R^a$ and $R^b$ are each independently —H or methyl;
  $R^2$, for each occurrence, is independently —H or methyl; and
  $R^1$ is —F or methyl;

(viii)

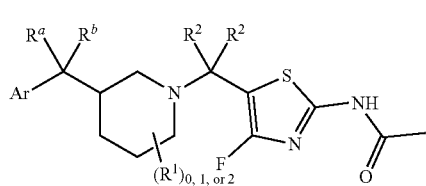
(Ia2')

or a pharmaceutically acceptable salt thereof; wherein
  $R^a$ and $R^b$ are each independently —H or methyl;
  $R^2$, for each occurrence, is independently —H or methyl; and
  $R^1$ is —F or methyl;

(ix)

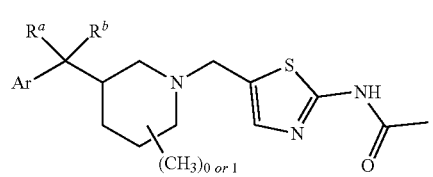
(Ia3)

or a pharmaceutically acceptable salt thereof;

(x)

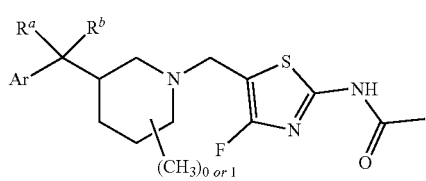
(Ia3')

or a pharmaceutically acceptable salt thereof;

(xi)

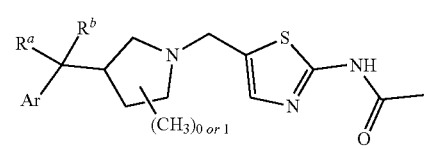
(Ib1)

or a pharmaceutically acceptable salt thereof; or (xii)

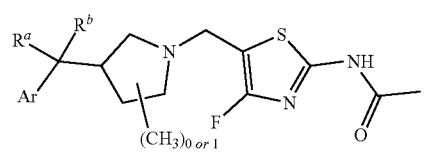
(Ib1')

or a pharmaceutically acceptable salt thereof.

4. The compound according to claim 1, wherein the compound is represented by the following structural formula:

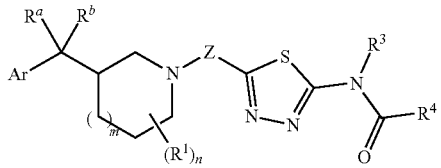

(II')

or a pharmaceutically acceptable salt thereof.

5. The compound according to claim 1, wherein the compound is represented by the following structural formula:

(i)

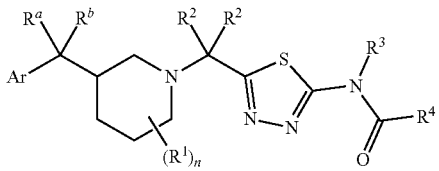

(IIa)

or a pharmaceutically acceptable salt thereof; wherein
R$^a$ and R$^b$ are each independently —H or C$_1$-C$_4$ alkyl; and
R$^2$, for each occurrence, is independently —H, halo, C$_1$-C$_4$ alkyl;

(ii)

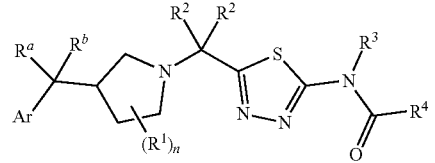

(IIb)

or a pharmaceutically acceptable salt thereof; wherein R$^2$, for each occurrence, is independently —H, halo, C$_1$-C$_4$ alkyl;

(iii)

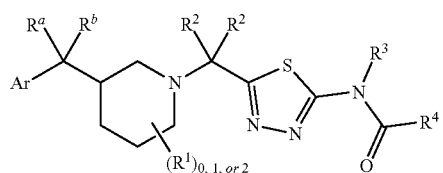

(IIa1)

or a pharmaceutically acceptable salt thereof; wherein
R$^a$ and R$^b$ are each independently —H or methyl;
R$^1$ is halo, C$_1$-C$_4$ alkyl or C$_1$-C$_4$ haloalkyl; and
R$^2$, for each occurrence, is independently —H or C$_1$-C$_4$ alkyl;

(iv)

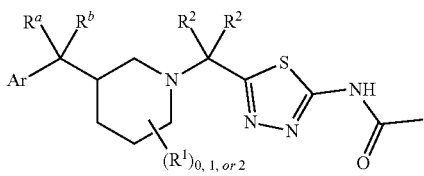

(IIa2)

or a pharmaceutically acceptable salt thereof; wherein
R$^a$ and R$^b$ are each independently —H or methyl;
R$^2$, for each occurrence, is independently —H or methyl; and
R$^1$ is —F or methyl;

(v)

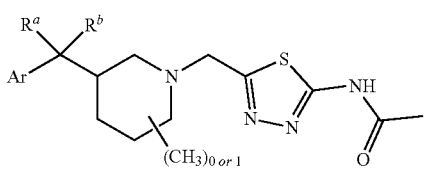

(IIa3)

or a pharmaceutically acceptable salt thereof; or (vi)

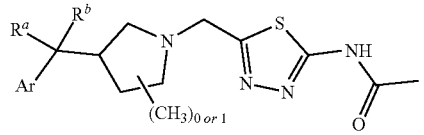

(IIb1)

or a pharmaceutically acceptable salt thereof.

6. The compound according to claim 1 or a pharmaceutically acceptable salt thereof, wherein Ar is optionally substituted pyrazolyl, optionally substituted imidazolyl, optionally substituted thiazolyl, optionally substituted phenyl, optionally substituted pyridinyl, optionally substituted pyrimidinyl, optionally substituted pyrazinyl, optionally substituted imidazo[1,2-a]pyridinyl, optionally substituted thieno[2,3-d]pyrimidinyl, or optionally substituted thieno[3,2-d]pyrimidinyl.

7. The compound according to claim 1 or a pharmaceutically acceptable salt thereof, wherein Ar is optionally substituted

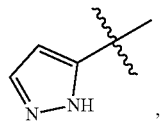, optionally substituted

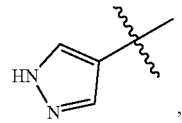, optionally substituted
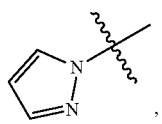
optionally substituted
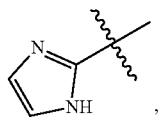 [SMILES: *c1ncc[nH]1]
optionally substituted
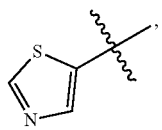 [SMILES: *c1cncs1]
optionally substituted
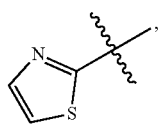
optionally substituted
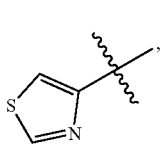 [SMILES: *c1cscn1]
optionally substituted
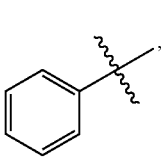
optionally substituted
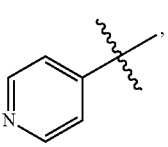 [SMILES: *c1ccncc1]
optionally substituted
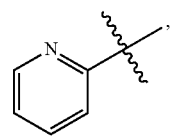 [SMILES: *c1ccccn1]
optionally substituted
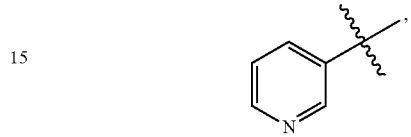
optionally substituted
optionally substituted
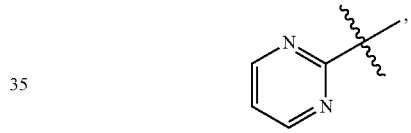
optionally substituted
optionally substituted
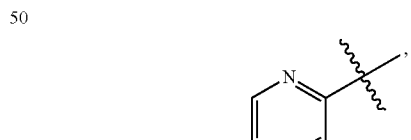
optionally substituted
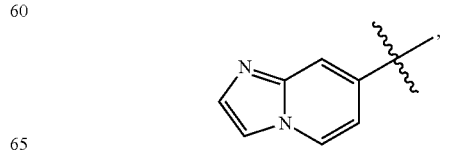

or optionally substituted

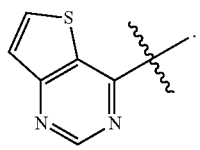 [SMILES: *c1ncnc2ccsc12]

8. The compound according to claim 1 or a pharmaceutically acceptable salt thereof, wherein:

Ar is optionally substituted with one or more groups selected from $C_1$-$C_4$ alkyl, $C_1$-$C_4$ haloalkyl, $C_3$-$C_6$ cycloalkyl, halo, —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, —C(=O)$R^x$, phenyl and monocyclic heteroaryl;

wherein the $C_1$-$C_4$ alkyl group substituent on Ar is optionally substituted with —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —NR(C=S)$NR^xR^y$, —C(=S)$R^x$, and —C(=O)$R^y$, $C_3$-$C_6$ cycloalkyl (optionally substituted with one or more groups selected from —$CH_3$, halomethyl, halo, methoxy and halomethoxy), monocyclic heteroaryl (optionally substituted with one or more groups selected from —$CH_3$, halomethyl, halo, methoxy or halomethoxy) and phenyl (optionally substituted with one or more groups selected from —$CH_3$, halomethyl, halo, methoxy and halomethoxy);

the $C_3$-$C_6$ cycloalkyl, phenyl and monocyclic heteroaryl group substituent on Ar are optionally and independently substituted with $C_1$-$C_4$ alkyl, $C_1$-$C_4$ haloalkyl, halo, —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —NR(C=O)$OR^y$, —O(C=O)$NR^xR^y$, —$NR^x$(C=S)$OR^y$, —O(C=S)$NR^xR^y$, —NR(C=O)$NR^xR^y$, —$NR^x$(C=S)$NR^xR^y$, —C(=S)$R^x$, and —C(=O)$R^x$;

each $R^x$ and each $R^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by $R^x$ or $R^y$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy or halomethoxy);

$R^z$ is —H, $C_1$-$C_4$ alkyl, or $C_3$-$C_8$ cycloalkyl; wherein the $C_1$-$C_4$ alkyl or $C_3$-$C_8$ cycloalkyl group represented by $R^z$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy and halomethoxy); and i is 0, 1, or 2.

9. The compound according to claim 1 or a pharmaceutically acceptable salt thereof, wherein Ar is optionally substituted with one or more groups selected from —$CH_3$, —$CH_2CH_3$, —$CHF_2$, —$CF_3$, cyclopentyl, cyclobutyl, —F, —Cl, —Br, —$OCH_3$, —C(=O)$CH_3$, and a thiazolyl.

10. The compound according to claim 1, wherein the compound is represented by the following structural formula:

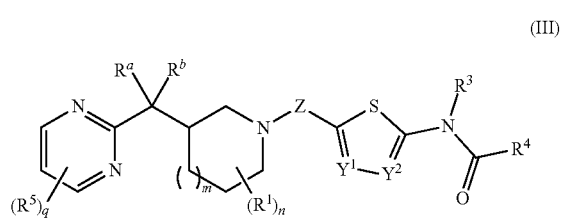

(III)

or a pharmaceutically acceptable salt thereof; wherein:

$Y^1$ and $Y^2$ are each $CR^c$ or N, wherein at least one of $Y^1$ or $Y^2$ is N;

Z is $CR^2R^2$, C(=O), $(CR^2R^2)_2$, $CH_2C$(=O), or C(=O)$CH_2$;

$R^a$, $R^b$ and $R^c$ are each independently —H, halo, $C_1$-$C_4$ alkyl, $C_1$-$C_4$ haloalkyl, or $C_1$-$C_4$ alkoxy, or $R^a$ and $R^b$ taken together with their intervening carbon atom form a $C_3$-$C_6$ cycloalkyl;

m is 0 or 1;

n is 0 or an integer from 1 to 7;

when n is other than 0, $R^1$, for each occurrence, is independently halo, $C_1$-$C_4$ alkyl, $C_1$-$C_4$ haloalkyl, $C_1$-$C_4$ alkoxy or $C_1$-$C_4$ haloalkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl;

or alternatively two $R^2$ together with the carbon atom to which they are attached form a $C_3$-$C_{10}$ cycloalkyl;

$R^3$ is —H or $C_1$-$C_4$ alkyl; and $R^4$ is —H, $C_1$-$C_4$ alkyl, $C_1$-$C_4$ haloalkyl, or $C_3$-$C_6$ cycloalkyl;

or alternatively $R^3$ and $R^4$ taken together with their intervening atoms form an optionally substituted 5- to 7-membered heterocyclyl;

$R^5$, for each occurrence, is selected from $C_1$-$C_4$ alkyl, $C_1$-$C_4$ haloalkyl, $C_3$-$C_6$ cycloalkyl, halo, —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, —C(=O)$R^x$, phenyl and monocyclic heteroaryl;

wherein when $R^5$ is a $C_1$-$C_4$ alkyl group, the $C_1$-$C_4$ alkyl group is optionally and independently substituted with —CN, —$NO_2$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, and —C(=O)$R^y$, $C_3$-$C_6$ cycloalkyl (optionally substituted with one or more groups selected from —$CH_3$, halomethyl, halo, methoxy and halomethoxy), monocyclic heteroaryl (optionally substituted with one or more groups selected from —$CH_3$, halomethyl, halo, methoxy or halomethoxy) and phenyl (optionally substituted with one or more groups selected from —$CH_3$, halomethyl, halo, methoxy and halomethoxy);

when $R^5$ is a $C_3$-$C_6$ cycloalkyl, phenyl or a monocyclic heteroaryl, the cycloalkyl, phenyl or a monocyclic heteroaryl is optionally and independently substituted with $C_1$-$C_4$ alkyl, $C_1$-$C_4$ haloalkyl, halo, —CN, —$NO_2$, —$OR^z$, —$NR^xR^y$, —$S(O)_iR^x$, —$NR^xS(O)_iR^y$, —$S(O)_iNR^xR^y$, —C(=O)$OR^x$, —OC(=O)$OR^x$, —C(=S)$OR^x$, —O(C=S)$R^y$, —C(=O)$NR^xR^y$, —$NR^x$(=O)$R^y$, —C(=S)$NR^xR^y$, —$NR^x$C(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, and —C(=O)$R^x$;

each $R^x$ and each $R^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by $R^x$ or $R^y$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy or halomethoxy);

$R^z$ is —H, $C_1$-$C_4$ alkyl, or $C_3$-$C_8$ cycloalkyl; wherein the $C_1$-$C_4$ alkyl or $C_3$-$C_8$ cycloalkyl group represented by $R^z$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy and halomethoxy); and i is 0, 1, or 2; and q 0, 1, 2, or 3.

11. The compound according to claim 10, wherein the compound is represented by the following structural formula:

(i)

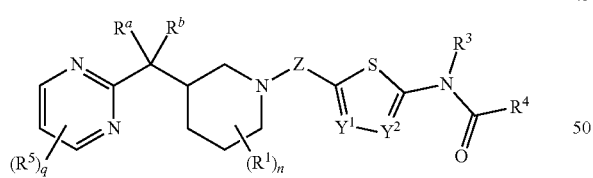

(IIIa)

or a pharmaceutically acceptable salt thereof;

(ii)

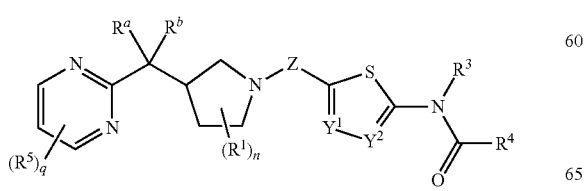

(IIIb)

or a pharmaceutically acceptable salt thereof; wherein q is 0, 1, 2, or 3;

(iii)

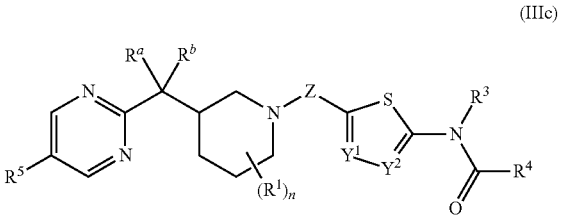

(IIIc)

or a pharmaceutically acceptable salt thereof;

(iv)

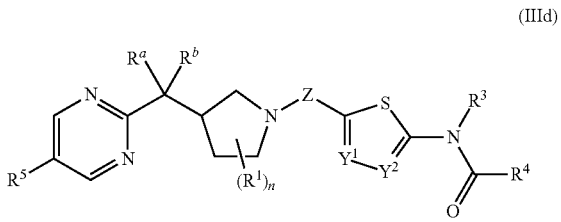

(IIId)

or a pharmaceutically acceptable salt thereof;

(v)

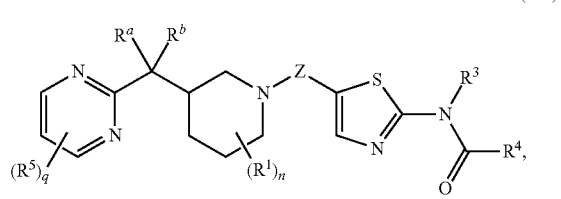

(IIIe)

or a pharmaceutically acceptable salt thereof;

(vi)

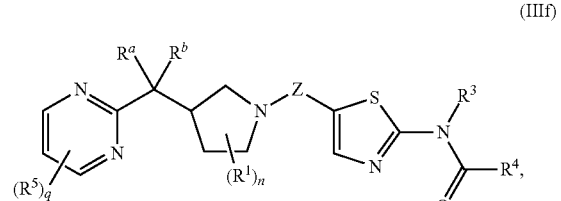

(IIIf)

or a pharmaceutically acceptable salt thereof; wherein q is 0, 1, 2, or 3;

(vii)

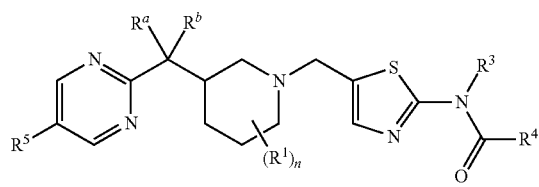
(IIIg)

or a pharmaceutically acceptable salt thereof;
(viii)

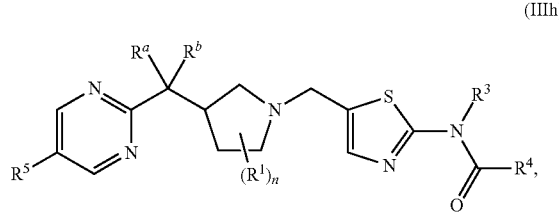
(IIIh)

or a pharmaceutically acceptable salt thereof;
(ix)

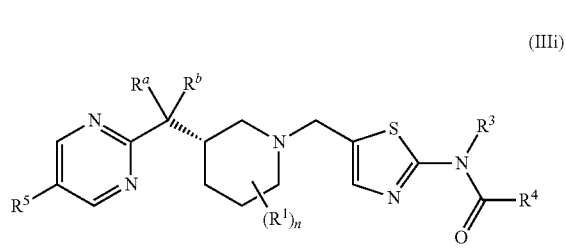
(IIIi)

or a pharmaceutically acceptable salt thereof;
(x)

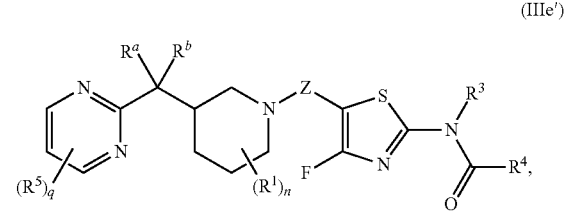
(IIIe')

or a pharmaceutically acceptable salt thereof; wherein q is 0, 1, 2, or 3;

(xi)

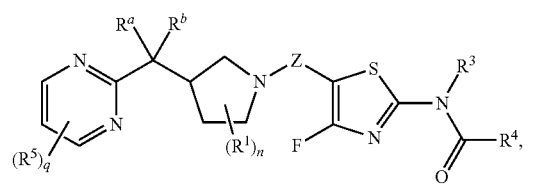
(IIIf')

or a pharmaceutically acceptable salt thereof;
(xii)

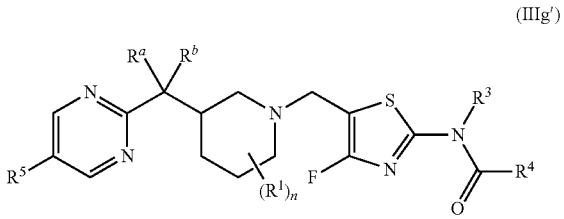
(IIIg')

or a pharmaceutically acceptable salt thereof;
(xiii)

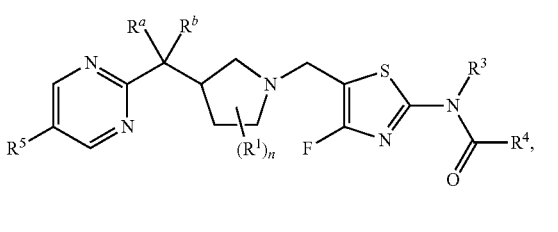
(IIIh')

or a pharmaceutically acceptable salt thereof;
(xiv)

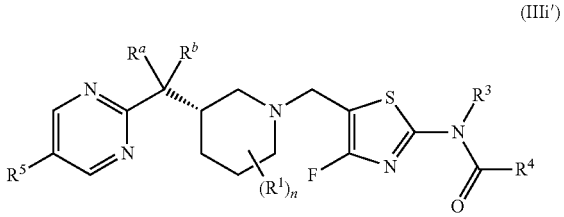
(IIIi')

or a pharmaceutically acceptable salt thereof;
(xv)

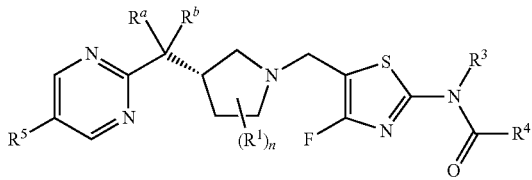
(IIIj')

or a pharmaceutically acceptable salt thereof; or
(xvi)

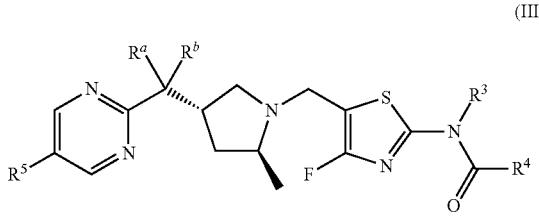
(IIIk')

or a pharmaceutically acceptable salt thereof.

12. The compound according to claim 1 or a pharmaceutically acceptable salt thereof, wherein $R^3$ is —H.

13. The compound according to claim 1 or a pharmaceutically acceptable salt thereof, wherein $R^4$ is —$CH_3$.

14. The compound according claim 1 or a pharmaceutically acceptable salt thereof, wherein $R^5$ is selected from $C_1$-$C_4$ alkyl, $C_1$-$C_4$ haloalkyl, $C_3$-$C_6$ cycloalkyl, halo, —CN, —$OR^z$, —$NR^xR^y$, —C(=O)$NR^xR^y$, —C(=S)$NR^xR^y$, —O(C=O)$NR^xR^y$, —O(C=S)$NR^xR^y$, —C(=O)$OR^x$, —$NR^xC(=O)R^y$ phenyl, —C(=O)$R^x$, and optionally substituted monocyclic heteroaryl.

15. The compound according to claim 1 or a pharmaceutically acceptable salt thereof, wherein $R^5$ is selected from —$CH_3$, —$CH_2CH_3$, —$CHF_2$, —$CF_3$, cyclopentyl, cyclobutyl, —F, —Br, Cl, —$OCH_3$, —C(=O)$CH_3$, and a thiazolyl.

16. The compound according to claim 1 or a pharmaceutically acceptable salt thereof, wherein one of $R^a$ and $R^b$ is —H and the other is selected from —$CH_3$, —$CF_3$, and —$OCH_3$.

17. The compound according to claim 1 or a pharmaceutically acceptable salt thereof, wherein n is 0 or 1.

18. A pharmaceutical composition comprising the compound according to claim or a pharmaceutically acceptable salt thereof and a pharmaceutically acceptable carrier or diluent.

19. A method of treating a subject with a disease or condition selected from a neurodegenerative disease, a tauopathy, diabetes, cancer and stress, comprising administering to the subject an effective amount of the compound according to claim 1.

20. A method of inhibiting O-GlcNAcase in a subject in need thereof, comprising administering to the subject an effective amount of the compound according to claim 1.

21. A method of treating a disease or condition characterized by hyperphosphorylation of tau in the brain, comprising administering to the subject an effective amount of the compound according to claim 1.

* * * * *